United States Patent [19]

Florkiewicz et al.

[11] Patent Number: 6,083,706
[45] Date of Patent: Jul. 4, 2000

[54] INHIBITORS OF LEADERLESS PROTEIN EXPORT

[75] Inventors: Robert Z. Florkiewicz, Ramona; Andrew Baird, San Diego, both of Calif.

[73] Assignee: Ciblex Corporation, San Diego, Calif.

[21] Appl. No.: 09/030,613

[22] Filed: Feb. 25, 1998

Related U.S. Application Data

[63] Continuation-in-part of application No. 08/807,014, Feb. 26, 1997.
[51] Int. Cl.$^7$ .......................... G01N 33/53; A01N 43/04; A01N 45/00; C12N 9/99; C07K 1/00
[52] U.S. Cl. .............................. 435/7.1; 514/443; 514/25; 514/26; 514/27; 514/28; 514/29; 514/30; 514/31; 435/184; 435/7.2; 435/7.1; 530/351; 530/396; 530/399
[58] Field of Search ................................ 514/443, 26, 25, 514/27, 28, 29, 30, 31; 435/184; 530/351, 396, 399

[56] References Cited

U.S. PATENT DOCUMENTS

| | | | |
|---|---|---|---|
| 4,975,467 | 12/1990 | Ku et al. | 514/712 |
| 5,545,623 | 8/1996 | Matsumori | 514/26 |
| 5,891,855 | 4/1999 | Florkiewicz | 514/26 |

FOREIGN PATENT DOCUMENTS

| | | |
|---|---|---|
| WO 92/16226 | 10/1992 | WIPO . |
| WO 93/09135 | 5/1993 | WIPO . |
| WO 96/04921 | 2/1996 | WIPO . |
| WO 97/28808 | 8/1997 | WIPO . |

OTHER PUBLICATIONS

Barinaga, "A Shared Strategy for Virulence," *Science* 272: 1261–1263, 1996.
Bost and Berlin, "A new genetic selection identifies essential residues in SecG, a component of the *Escherichia coli* protein export machinery," *The EMBO Journal* 14(18): 4412–4421, 1995.
DeTomaso et al., "The α and β Subunits of the Na, K-ATPase Can Assemble at the Plasma Membrane into Functional Enzyme," *The Journal of Cell Biology* 127: 55–69, 1994.
Florkiewicz et al., "Cardenolides inhibit FGF-2 protein export: A novel regulatory function for Na+, K+-ATPase," *FASEB Journal* 11(9): No. 1222, p. A1066, 1997.
Florkiewicz et al., "Quantitative Export of FGF-2 Occurs Through and Alternative, Energy–Dependent, Non-ER/Golgi Pathway," *Journal of Cellular Physiology* 162:388–399, 1995.
Florkiewicz et al., "Regulation Of FGF–2 Export By Cardenolides," *Molecular Biology Of The Cell* 7(Suppl.):No. 1080, p. 186a, 1996.
Florkiewicz et al., "The Inhibition of Fibroblast Growth Factor–2 Export by Cardenolides Implies a Novel Function for the Catalytic Subunit of Na$^+$, K$^+$–ATPase," *The Journal of Biological Chemistry* 273(1):544–551, 1998.

Goldstein, "HIV 1 Tat protein as a potential AIDS vaccine," *Nature Medicine* 1(9):960–964, 1996.
Hamon et al., "Interleukin–1β Secretion Is Impaired by Inhibitors of the Atp Binding Cassette Transporter, ABC1," *Blood* 90(8):2911–2915, 1997.
Jackson et al., "The Release of Fibroblast Growth Factor–1 from NIH 3T3 Cells in Response to Temperature Involves the Function of Cysteine Residues," *The Journal of Biological Chemistry* 270(1):33–36, 1995.
Jarvis et al., "Enteropathogenic *Escherichia coli* contains a putative type III secretion system necessary for the export of proteins involved in attaching and effacing lesion formation," *Proc. Natl. Acad. Sci. USA* 92: 7996–8000, 1995.
Jerse et al., "A genetic locus of enteropathogenic *Escherichia coli* necessary for the production of attaching and effacing lesions on tissue culture cells," *Proc. Natl. Acad. Sci. USA* 87: 7839–7843, 1990.
Kaelin Jr. et al., "Identification of Cellular Proteins That Can Interact Specifically with the T/E1A–Binding Region of the Retinoblastoma Gene Product," *Cell* 64:521–532, 1991.
Kenny and Finlay, "Protein secretion by enteropathogenic *Escerichia coli* is essential for transducing signals to epthelial cells," *Proc. Natl. Acad. Sci. USA* 92: 7991–7995, 1995.
Kent et al., "Ouabain Resistance Conferred by Expression of the cDNA for a Murine Na$^+$, K$^+$–ATPase α Subunit," *Science* 237:901–903, 1987.
Levenson, "Isoforms of the Na, K–ATPase: Family Members in Search of Foundation," *Rev. Physiol. Biochem. Pharmacol.* 123: 1–45, 1994.
Lewis, "Multidrug resistance pumps in bacteria: variations on a theme," *TIBS* 19: 119–124, 1994.
McDaniel et al., "A genetic locus of enterocyte effacement conserved among diverse enterobacterial pathogens," *Proc. Natl. Acad. Sci. USA* 92: 1664–1668, 1995.
Mignatti et al., "Basic Fibroblast Growth Factor, a Protein Devoid of Secretory Signal Sequence, Is Released by Cells via a Pathway Independent of the Endoplasmic Reticulum–Golgi Complex," *Journal Of Cellular Physiology* 151: 81–93, 1992.
Neyfakh et al., "Efflux–mediated multidrug resistance in *Bacillus subtilis*: Similarities and dissimilarities with the mammalian system," *Proc. Natl. Acad. Sci. USA* 88: 4781–4785, 1991.
Rubartelli et al., "A novel secretory pathway for interleukin–1β, a protein lacking a signal sequence," *The EMBO Journal* 9(5): 1503–1510, 1990.

(List continued on next page.)

*Primary Examiner*—Nita Minnifield
*Assistant Examiner*—Padma Baskar
*Attorney, Agent, or Firm*—Seed Intelolectual Property Law Group PLLC

[57] ABSTRACT

Methods of inhibiting the export of a leaderless protein from a cell by contacting the cell with a compound that inhibits the binding of the leaderless protein and a transport molecule are provided. Leaderless proteins include FGF-1, FGF-2, IL-1α, IL-1β, CNTF and HIV-tat. These methods are useful in treatment of various conditions, including tumors and diabetes.

6 Claims, 31 Drawing Sheets

OTHER PUBLICATIONS

Rubartelli et al., "Secretion of Thioredoxin by Normal and Neoplastic Cells through a Leaderless Secretory Pathway," *The Journal Of Biological Chemistry* 267(34):24161–24164, 1992.

Russel, "Phage Assembly: A Paradigm for Bacterial Virulence Factor Export," *Science* 265: 612–614, 1994.

Salmond and Reeves, "Membrane traffic wardens and protein secretion in Gram–negative bacteria," *TIBS* 18: pp. 7–12, 1993.

Harlow etal, Antibodies, A laboratory manual 421–466 and 511–551, 1988.

Nilsson et al, Fusion proteins in biotechnology and structural biology, Current opinion in structural biology, vol. 2, pp. 569–575, 1992.

CO-TRANSFECTION: 18-kDa FGF-2 PLUS Na$^+$, K$^+$-ATPase$\alpha$1

| cat# | molstructure | molename | µM | % Inhibition FGF2 | nM | % Inhibition FGF2 | % Inhibition hCG 50 µM | % Inhibition hCG 50 nM |
|---|---|---|---|---|---|---|---|---|
| 501428 | | N-PHENACYL-N-PHENYLTRIFLUOROMETHYLSULFONAMIDE | 14.6 | 74 | 145.6 | | 0 | 0 |
| 01800050 | | ATEBRINE | 13.97 | 64 | 139.7 | 22 | 35 | 0 |
| 01800123 | | ECHINOCYSTIC ACID | 10.6 | 63 | 105.8 | | 36 | 16 |
| 01901031 | | N,N¹-DI-(2,4-DIAMINOPHENYL)S OPHTHALAMIDE | 13.3 | 62 | 132.8 | 58 | 9 | 0 |
| 00924321 | | 2-BENZAMIDO-3-CARBOXY-4,5,6,7-TETRAHYDRO BENZ[b]THIOPHENE | 16.6 | 60 | 165.9 | 11 | 27 | 14 |

Fig. 29A

| cat# | molstructure | molename | μM | % Inhibition FGF2 | nM | % Inhibition FGF2 | % Inhibition hCG 50 μM | % Inhibition hCG 50 nM |
|---|---|---|---|---|---|---|---|---|
| 00926838 | | N,N¹-DI-(4-DIMETHYLAMINOBENZYLIDENE)HYDRAZINE | 17.0 | 60 | 169.8 | 63 | 0 | 7 |
| 922645 | | 6-PENTYLIDENEAMINOPURINE | 24.6 | 59 | 246 | | 0 | 0 |
| 00927210 | | DI-(4-CYCLOHEXYLOXYETHOXYCARBONYL AMINOPHENYL)METHANE | 9.3 | 58 | 92.8 | | 0 | 6 |
| 01100596 | | 2-(t-BUTYLAMINOSULFONYL)-3-PHENYLACRYLIC ACID, ETHYL ESTER | 16.06 | 55 | 160.6 | 0 | ND | ND |

Fig. 29B

| 01100194 |  2-BENZYLOXYCARBONYL-5-[(2,2-DIETHOXYCARBONYL)ETHYLIDENYL]PYRROLE | 13.46 | 69 | 134.6 | 0 | ND | ND |

INHIBITORS OF LEADERLESS PROTEIN EXPORT

CROSS-REFERENCE TO RELATED APPLICATION

The application is a continuation-in-part of U.S. patent application Ser. No. 08/807,014, filed Feb. 26, 1997.

TECHNICAL FIELD

The present invention relates generally to inhibitors of leaderless protein export, and more specifically, to methods of identifying compounds that inhibit export of leaderless proteins into extracellular spaces.

BACKGROUND OF THE INVENTION

Many proteins exert an effect on cell growth, differentiation, and inflammation through signal transduction, mediated by binding to a cell surface receptor. Yet other proteins, such as factors that initiate or are necessary for blood clot formation, act enzymatically in blood. While these actions are generally part of normal processes, under certain circumstances, it may be desirable to limit or inhibit the action of certain proteins and the effects of subsequent signaling. For example, tumor growth that is promoted by a growth factor, such as bFGF acting on melanoma cells, is deleterious and often leads to fatalities.

Approaches to inhibit specific proteins have concentrated primarily on interfering with protein-substrate or protein-receptor interactions. Typically, this involves using an antibody or other molecule that competitively binds the protein, by administration of competitors for receptor binding, or by protease digestion of the protein. An alternative approach, not generally pursued, is to reduce the level of the protein by inhibiting its expression at a transcriptional or translational level. Methods of reducing protein levels by inhibiting the transcription or translation of the protein have been difficult to achieve because of inherent problems of inhibiting the specific expression of one or a few proteins.

The discovery that certain proteins, such as growth factors, mediators of inflammation, and mediators of blood clotting, are exported through a nonclassical secretory pathway allows the development of specific inhibitors for these proteins. These proteins are identified by their lack of a hydrophobic leader sequence that mediates secretion by the classical Golgi/ER pathway.

This invention provides inhibitors of the export of these leaderless proteins, allowing control of undesired proliferation and inflammation, as well as other related advantages.

SUMMARY OF THE INVENTION

The present invention generally provides methods of inhibiting the export of a leaderless protein from a cell expressing the protein. In one aspect, methods are provided for inhibiting export of a leaderless protein from a cell, comprising contacting a cell exporting a leaderless protein with an effective amount of an inhibitor of the binding between the leaderless protein and a transport molecule. In certain embodiments, the leaderless protein is FGF-1, FGF-2, IL-1α, IL-1β, CNTF or HIV-tat. In other preferred embodiments the transport molecule is $Na^+/K^+$ ATPase, an α subunit of $Na^+/K^+$ ATPase or a complex containing an α subunit of $Na^+/K^+$ ATPase. In other preferred embodiments, the transport molecule is selected from the group of ion channels consisting of $Ca^+$ ATPase, $H^+/K^+$ ATPase, $Na^+$ channel, $Cl^-$ channel and $K^+$ channel.

In another aspect, methods are provided for inhibiting export of FGF-2 from a cell, comprising contacting a cell exporting FGF-2 with an effective amount of an inhibitor of the binding between FGF-2 and a transport molecule, thereby inhibiting export of FGF-2. In preferred embodiments, the transport molecule is $Na^+/K^+$ ATPase, an α subunit of $Na^+/K^+$ ATPase, or a complex containing an α subunit of $Na^+/K^+$ ATPase.

In yet another aspect, inhibitors of export of a leaderless protein from a cell are provided. The inhibitor should (a) inhibit export of a leaderless protein; (b) not inhibit secretion of a leader sequence-containing protein; and (c) inhibit the binding between the leaderless protein and a transport molecule.

In related aspects, methods of treating angiogenesis or restenosis are provided. In these methods, endothelial cells or smooth muscle cells are contacted with therapeutically effective amount of an inhibitor of leaderless protein export.

In addition, methods for detecting leaderless proteins are provided,. comprising (a) transfecting or transforming an expression cDNA library that expresses cDNA fusion proteins at low multiplicity into a host cell; (b) detecting a cDNA fusion protein in cell supernatant; and (c) determining that the cDNA is a leaderless protein. In a preferred embodiment, the cDNA fusion protein is fused to a reporter or tag sequence.

Methods are also provided for detecting a transport molecule for a leaderless protein, comprising: (a) contacting cell extracts or cell membranes containing a transport molecule with a fusion protein of a leaderless protein and a tag to form a complex of the fusion protein bound to the transport molecule; (b) isolating the complex; and (c) detecting the transport molecule in the complex. In a preferred embodiment, the tag is glutathione-S-transferase or fragment thereof that binds glutathione.

These and other aspects of the present invention will become evident upon reference to the following detailed description and attached drawings. Various references are set forth below which describe in more detail certain procedures or compositions (e.g., plasmids). All of these references are incorporated by reference in their entirety.

BRIEF DESCRIPTION OF THE DRAWINGS AND SEQUENCE LISTING

FIG. 1 is a drawing indicating four models for inhibition of FGF-2 export by cardioglycosides. A, $Na^+/K^+$ ATPase is a component of a plasma membrane translocation apparatus (PMTA/exporter) for FGF-2; B, the transmembrane electrochemical gradient established by $Na^+/K^+$ ATPase is functionally necessary or some other protein required for FGF-2 export; C, cardioglycosides interact with an unidentified protein required for FGF-2 export; D, cardioglycosides interact with $Na^+/K^+$ ATPase which interacts with another component of plasma membrane translocation apparatus.

FIG. 2 is an autoradiogram of an immunoprecipitation electrophoresed, on an SDS-polyacrylamide gel. Panel A, immunoprecipitation of cell (C) and media (M) fractions with anti-FGF-2 antibodies at various times following co-transfection of plasmids expressing FGF-2 and $Na^+/K^+$ ATPase. (S) contains molecular weight standards. The double arrow points to a 110 kDa protein, which is the size of rat $Na^+/K^+$ ATPase α1 subunit. Panel B, immunoprecipitation following transfection of FGF-2 plasmid alone.

FIG. 3 is an autoradiogram of an immunoprecipitation electrophoresed on an SDS-PAGE. Panel A, immunoprecipitation of cell (C) and media (M) fractions with anti- FGF-2 antibodies at various times following co-transfection of plasmids expressing FGF-2 and Na$^+$/K$^+$ ATPase; 1 mM ouabain was included during cell culture. The arrow points to a 110 kDa protein, which is the size of rat Na$^+$/K$^+$ ATPase α1 subunit. Panel B, immunoprecipitation following co-transfection and culture with or without ouabain.

Figure 7:
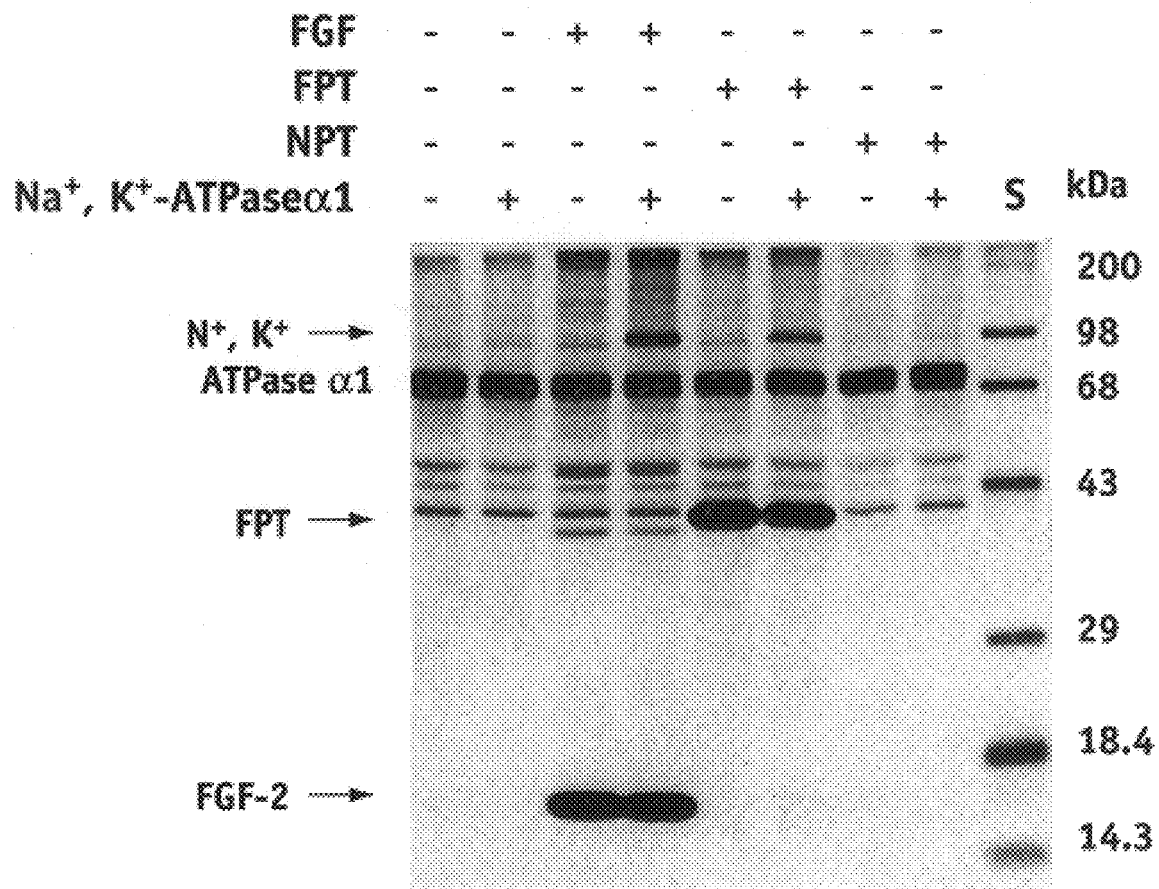

FIG. 7 is an autoradiogram of an immunoprecipitation with anti-FGF-2 immune serum following transfection of COS cells. The table at the top indicates table transfected genes. The lane marked "S" contains molecular weight standards. FPT is a chimera between FGF-2 and neomycin phosphotransferase.

Figure 8:
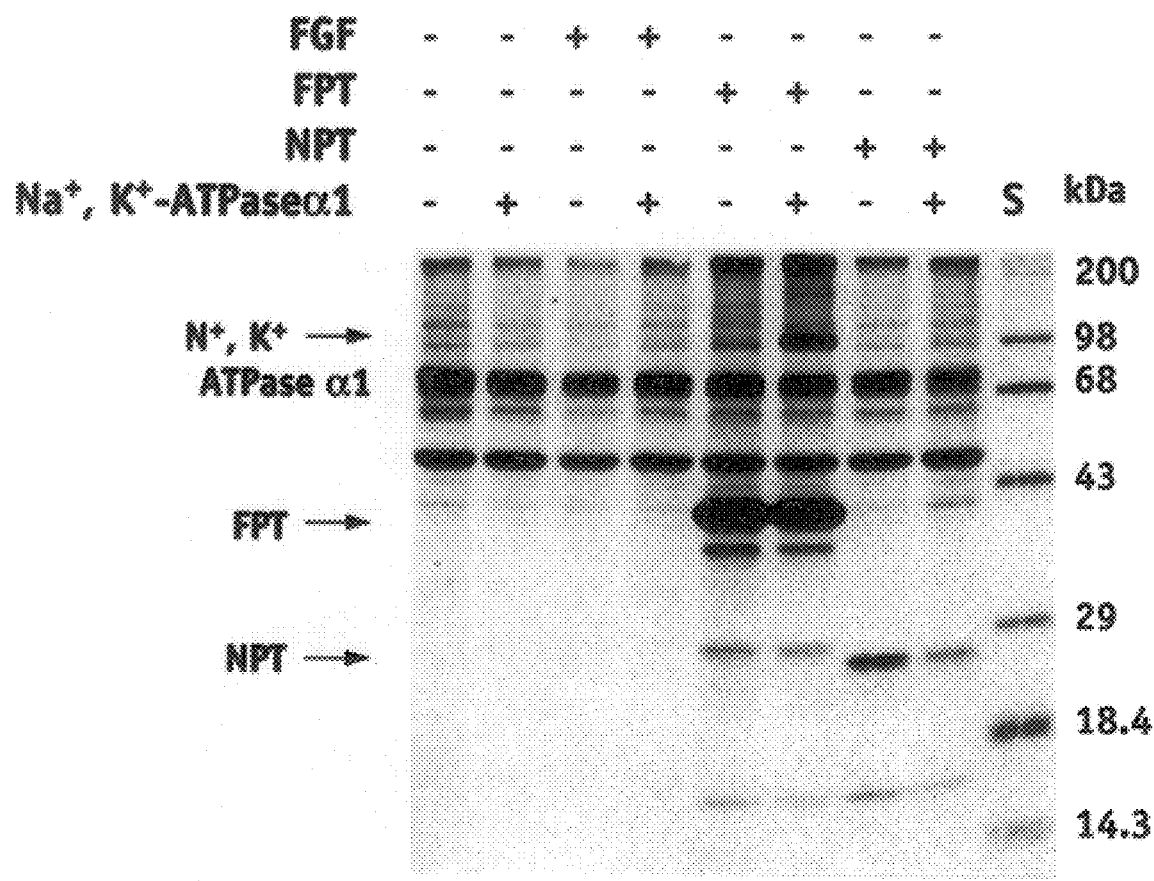

FIG. 8 is an autoradiogram of an immunoprecipitation with anti-neomycin phosphotransferase antibody following transfection of COS cells. The table at the top indicates the transfected genes. The lane marked "S" contains molecular weight standards. FPT is a chimera between FGF-2 and neomycin phosphotransferase.

Figure 9:
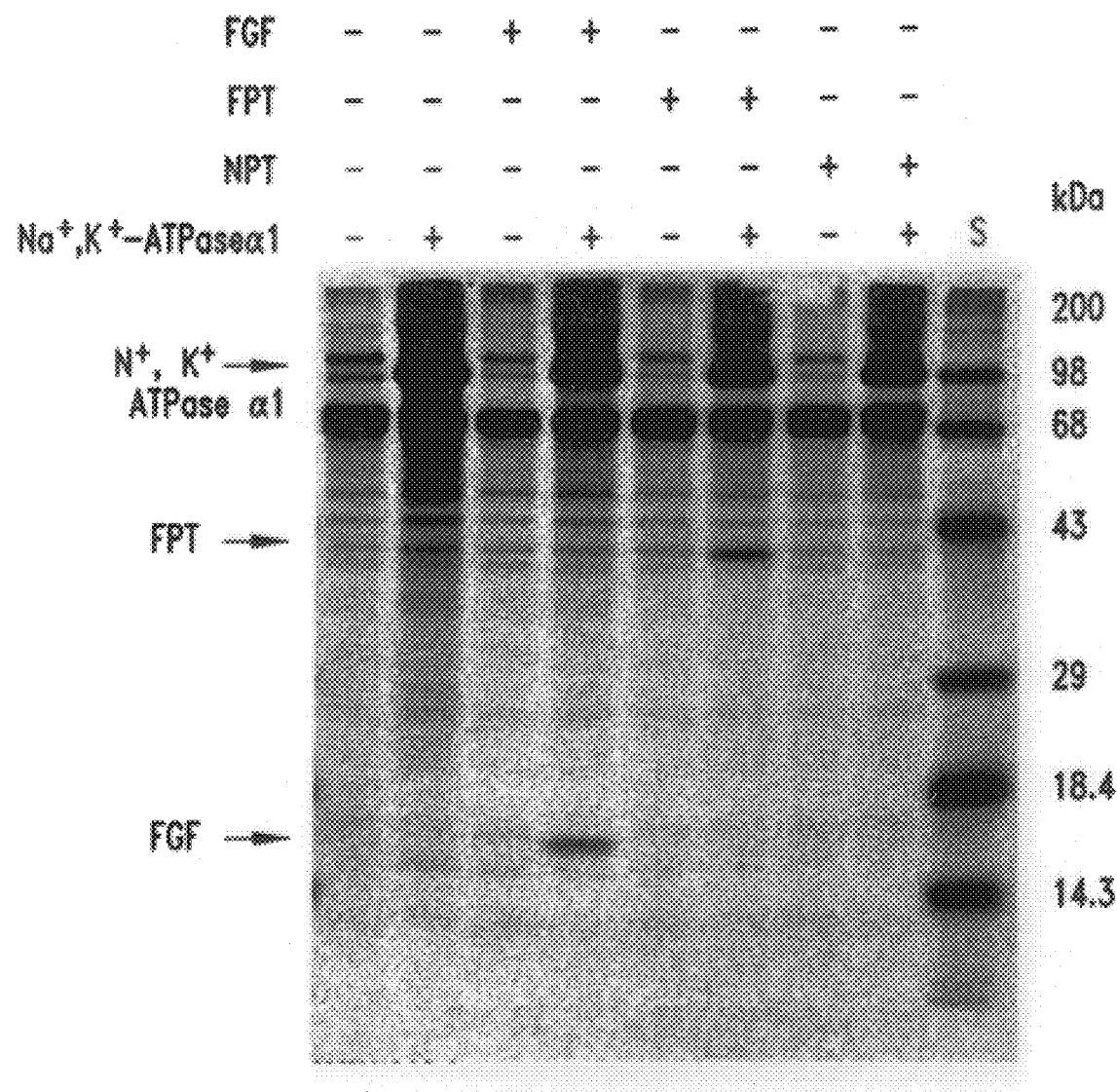

FIG. 9 is an autoradiogram of an immunoprecipitation with anti-Na$^{30}$/K$^{30}$ ATPase antibody following transfection of COS cells. The table at the top indicates the transfected genes. The lane marked "S" contains molecular weight standards. FPT is a chimera between FGF-2 and neomycin phosphotransferase.

Figure 10:
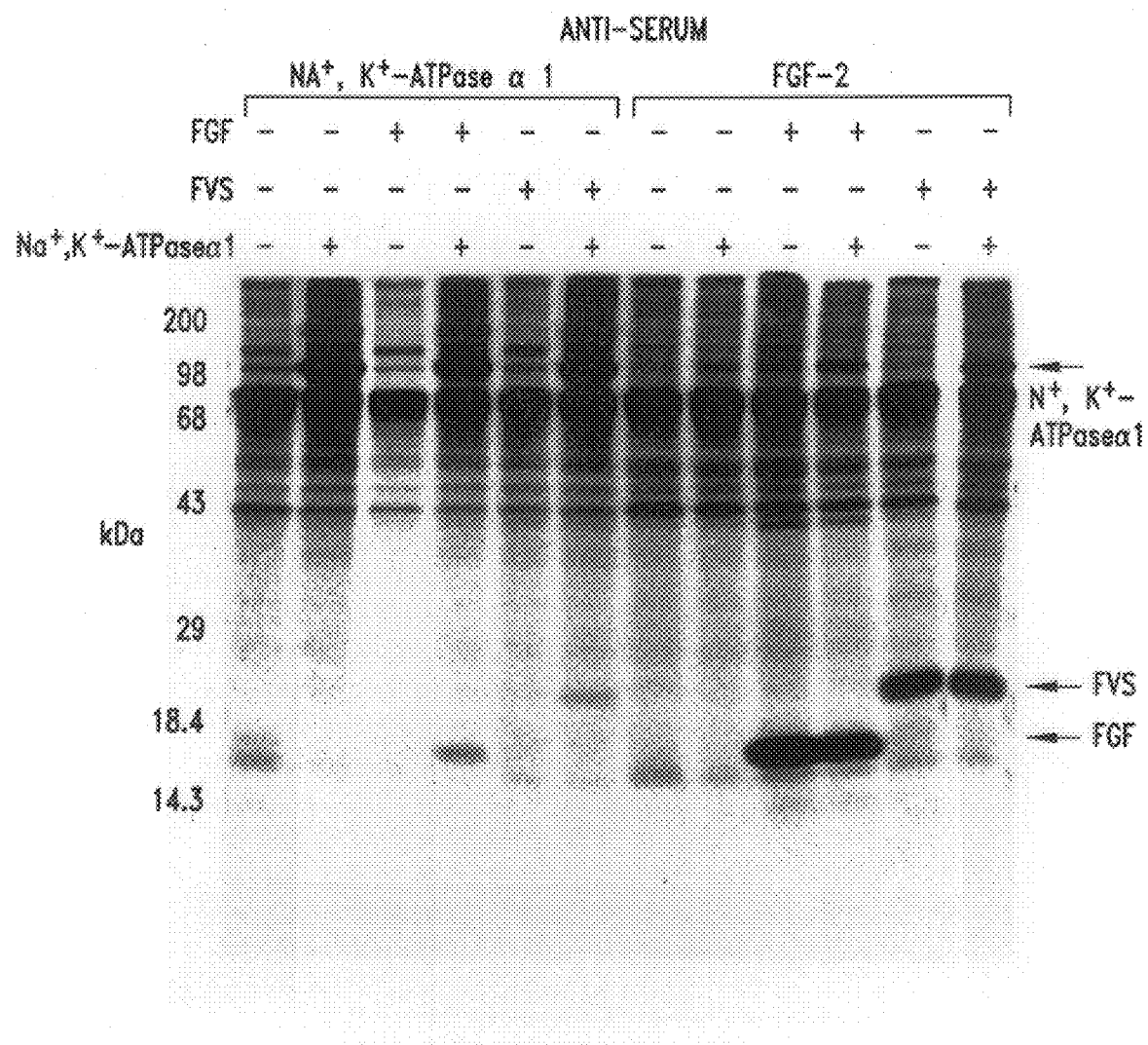

FIG. 10 is an autoradiogram of an immunoprecipitation with either anti-Na$^+$/K$^+$ ATPase antibody or anti-FGF-2 antibody following transfection of COS cells. The table at the top indicates the transfected genes. FVS is a chimeria between vesicular stomatitis virus transmembrane domain and FGF-2.

Figure 11:
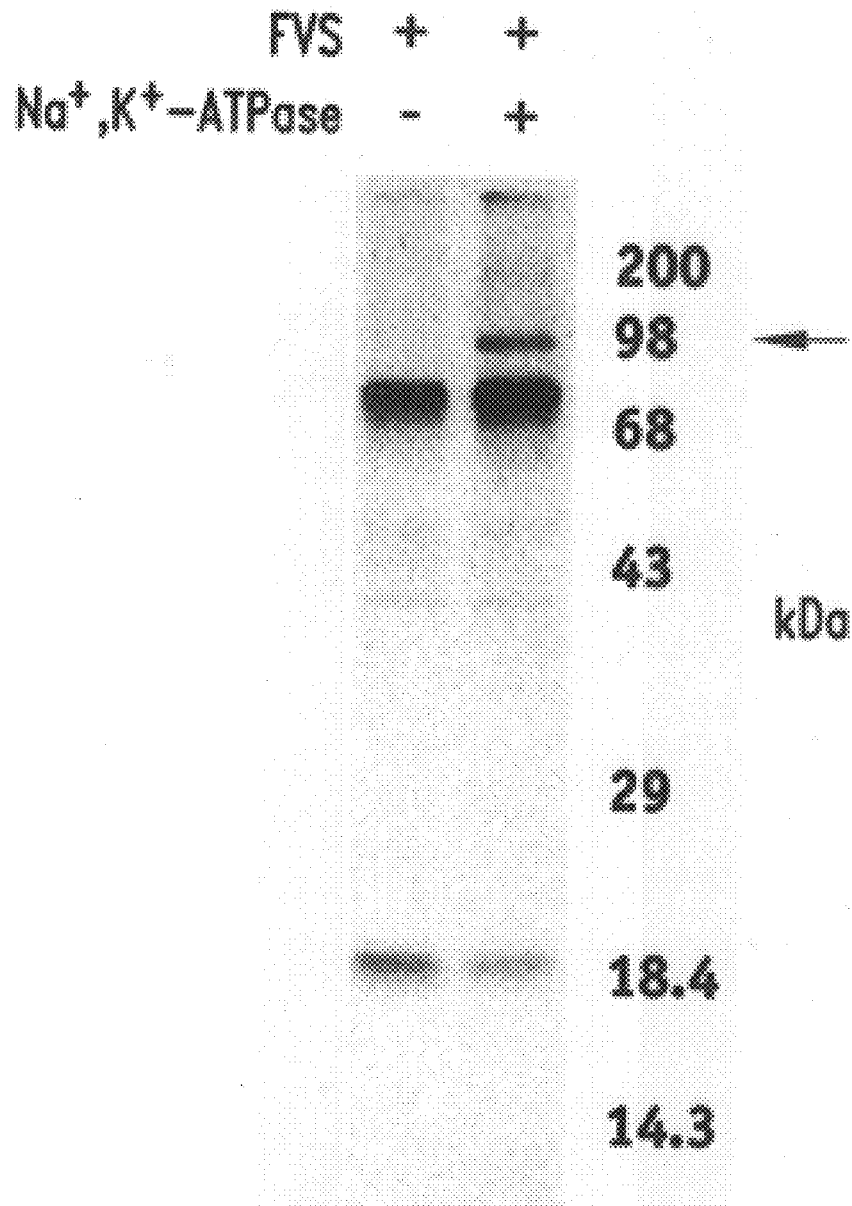

FIG. 11 is an autoradiogram of an immunoprecipitation with anti-FGF-2 antibody following transfection of COS cells. The table at the top indicates the transfected genes. FVS is a chimeria between vesicular stomatitis virus transmembrane domain and FGF-2.

Figure 12A:
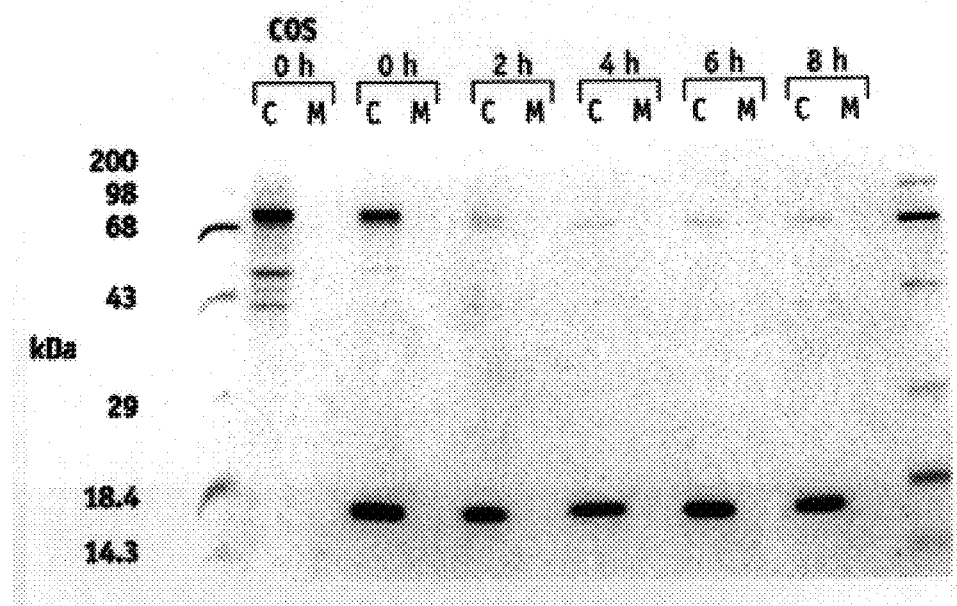
Figure 12B:
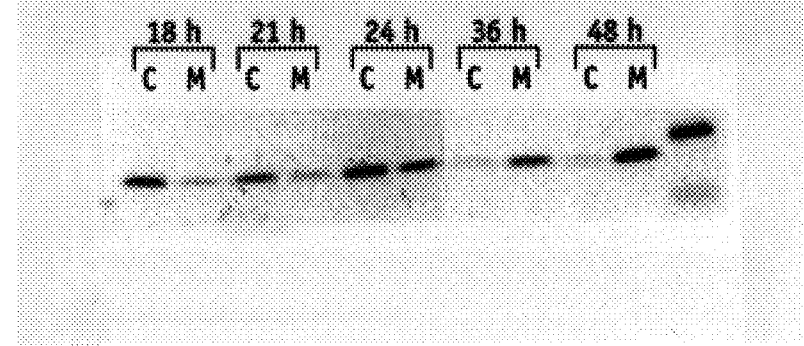

FIGS. 12A and 12B present an autoradiogram of an immunoprecipitation with anti-IL-1 antibody following transfection of COS cells with a plasmid encoding IL-1.

Figure 13:
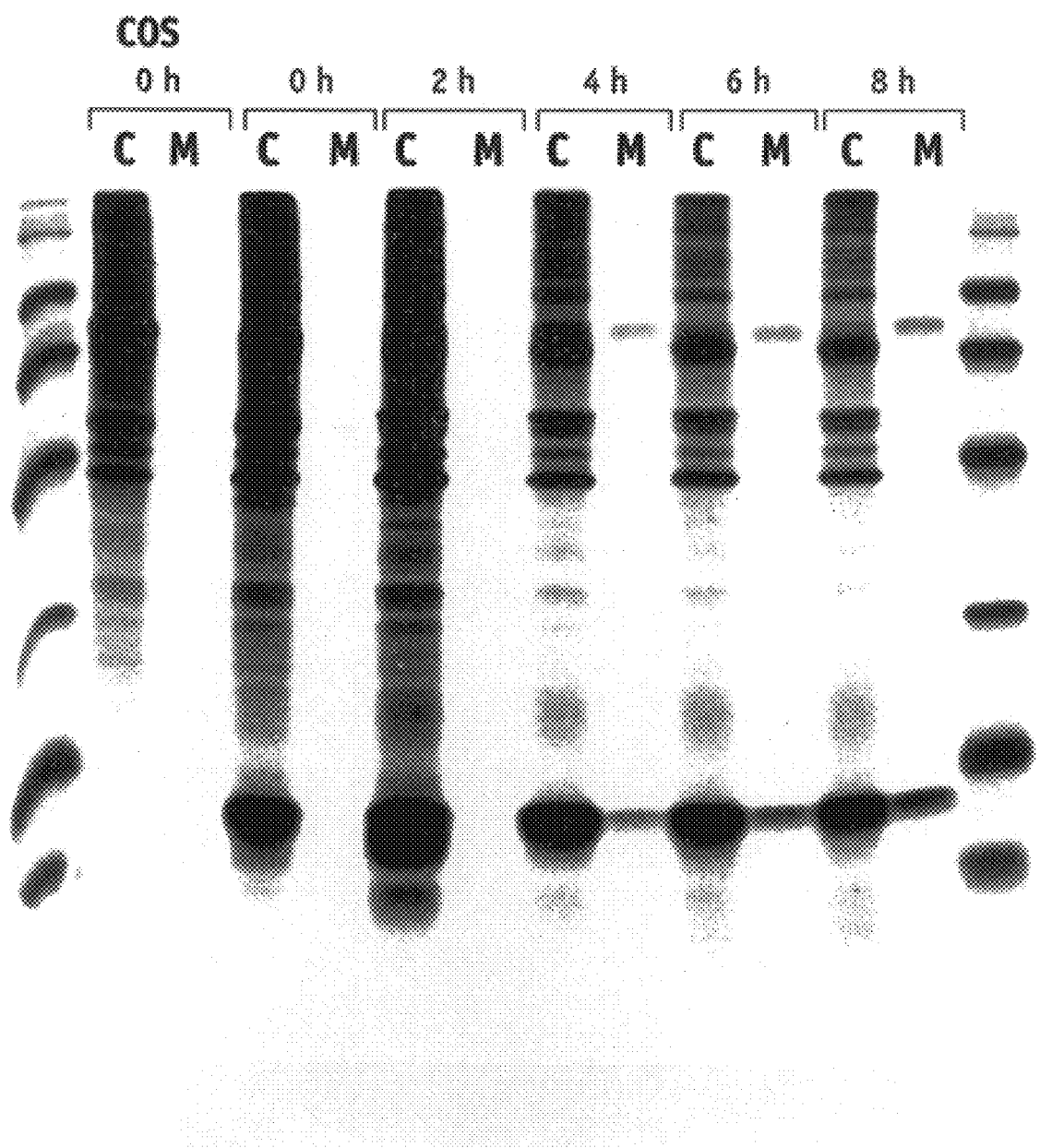

FIG. 13 is an autoradiogram of an immunoprecipitation with anti-FGF2 antibody following transfection of COS cells with plasmids expressing FGF2 and rat α2 subunit of Na$^+$/K$^+$ ATPase.

Figure 14:
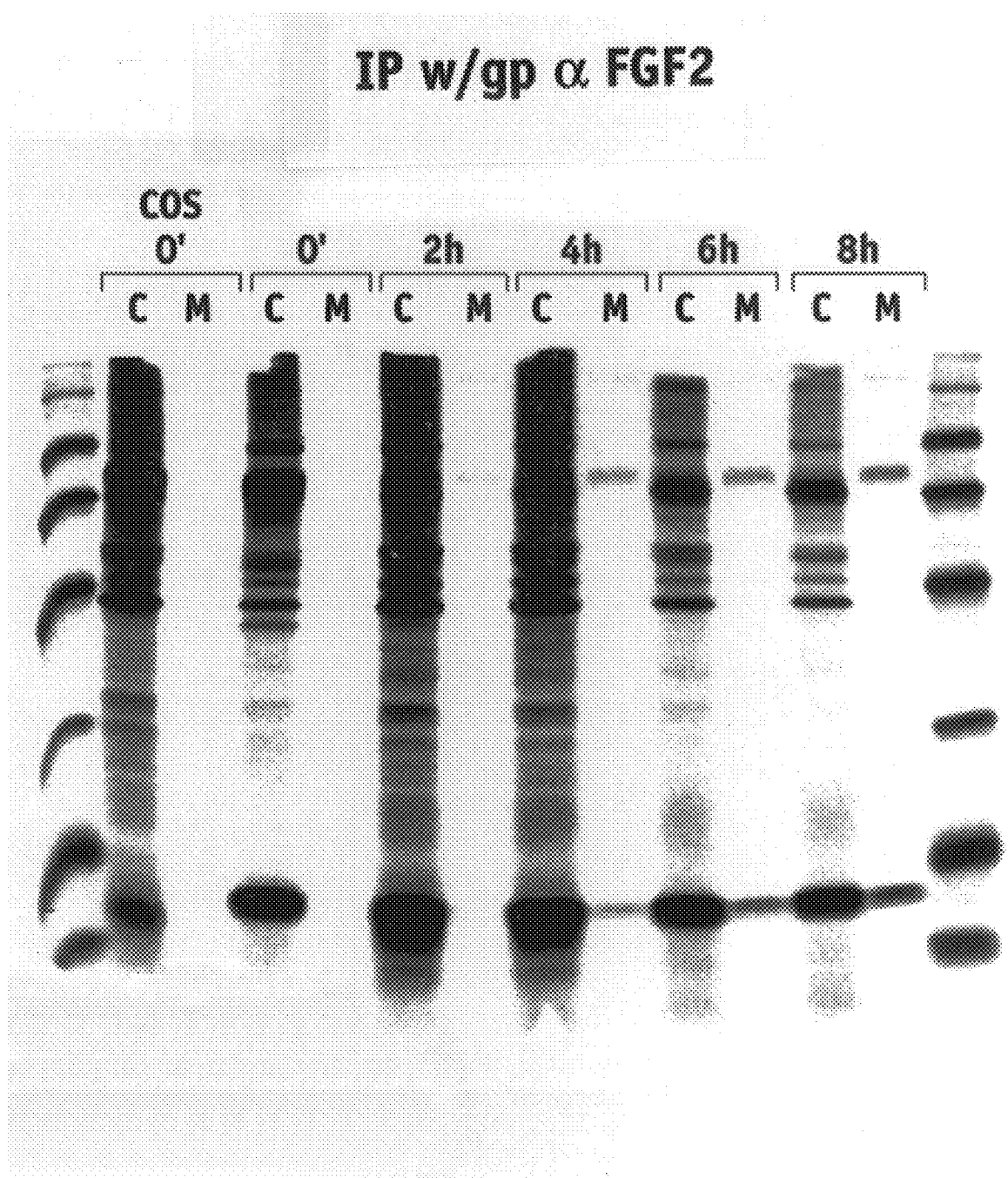

FIG. 14 is an autoradiogram of an immunoprecipitation with anti-FGF2 antibody following transfection of COS cells with plasmids expressing FGF2 and rat α3 subunit of Na$^+$/K$^+$ ATPase.

Figure 15:
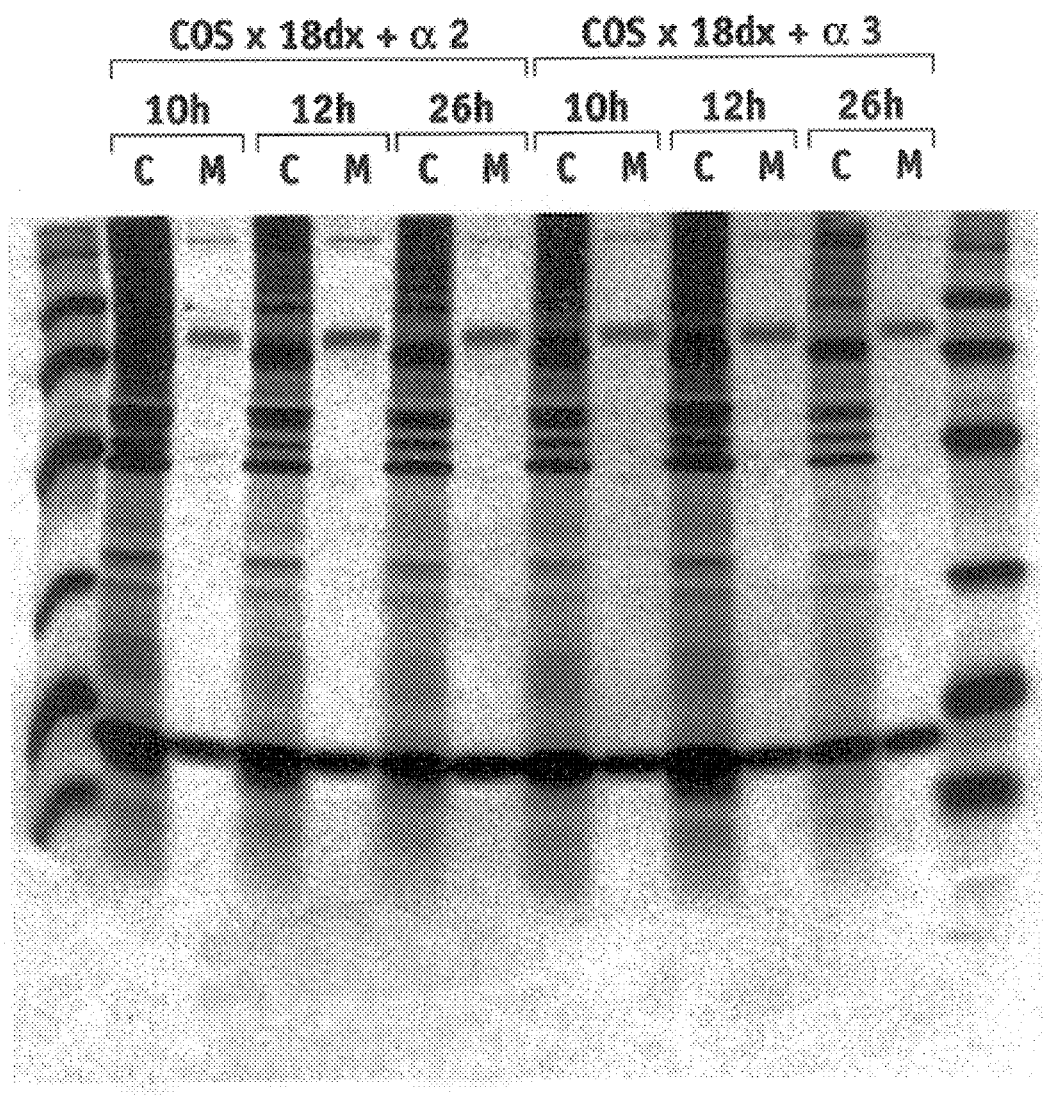

FIG. 15 is an autoradiogram of an immunoprecipitation with anti-FGF2 antibody following transfection of COS cells with plasmids expressing FGF2 and rat α2 subunit or FGF2 and rat α3 subunit.

Figure 16:
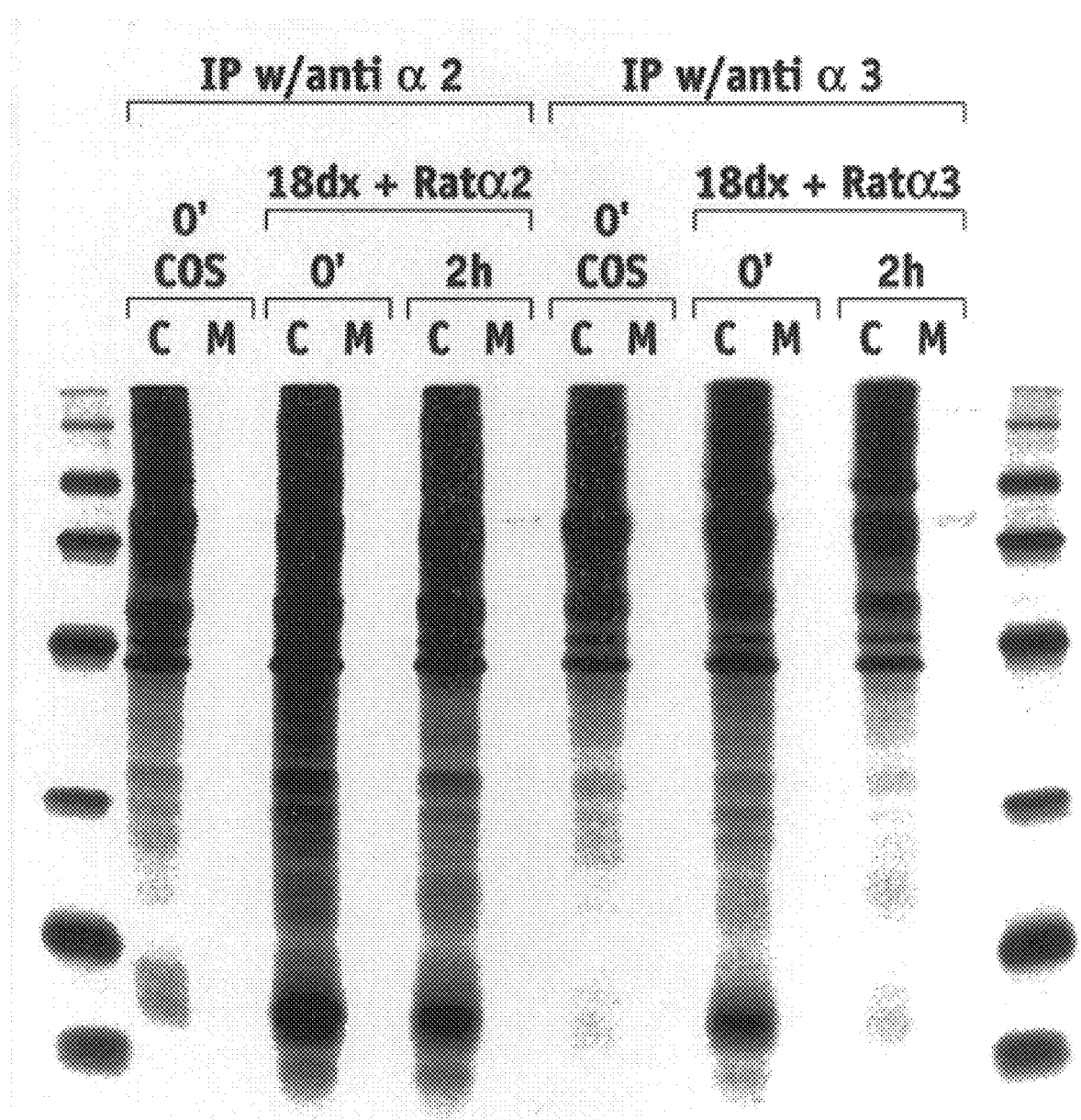

FIG. 16 is an autoradiogram of an immunoprecipitation with anti-α2 or anti-α3 subunit antibody following transfection of COS cells with plasmids expressing FGF2 and rat α2 subunit or FGF2 and rat α3 subunit.

Figure 17:
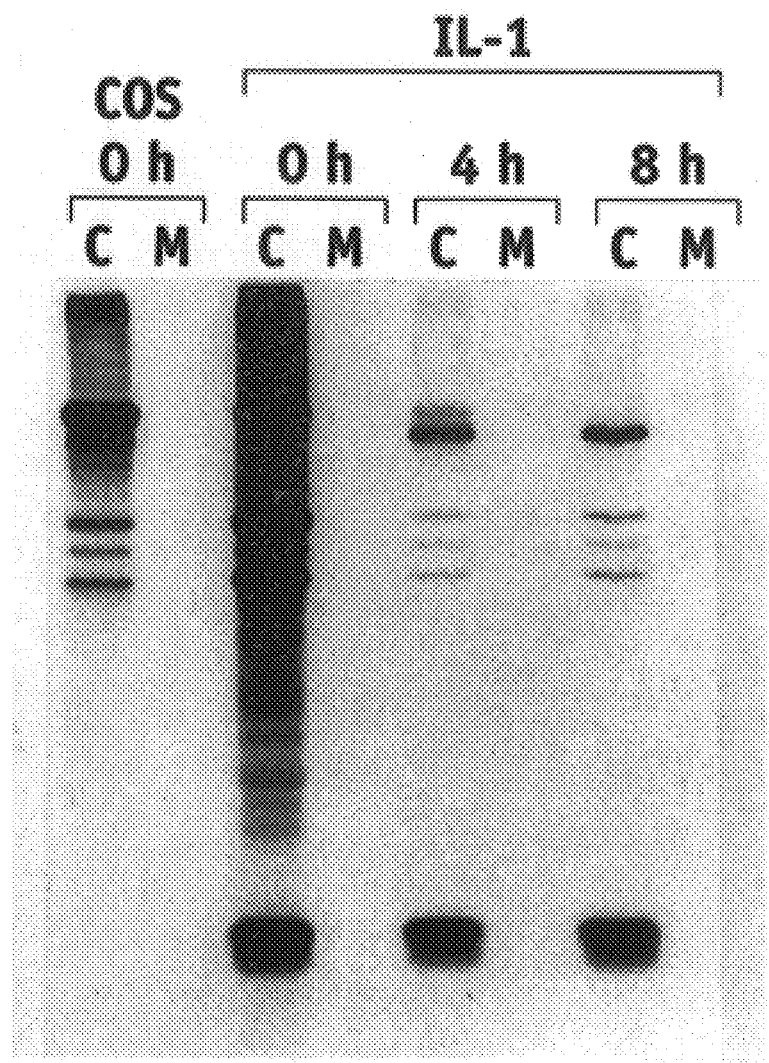
Figure 18:
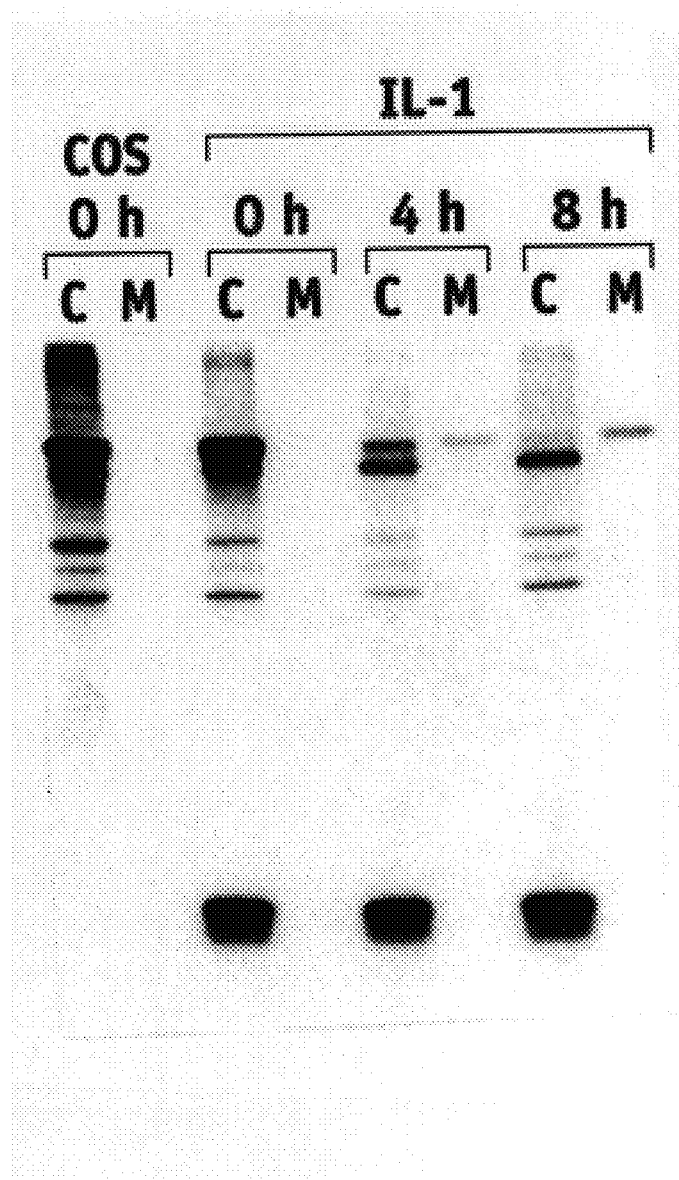

FIGS. 17 and 18 are autoradiogram of an immunoprecipitation with anti-IL-1 antibody following transfection of COS cells with a plasmid expressing IL-1 and treated without and with ouabain respectively.

Figure 19:
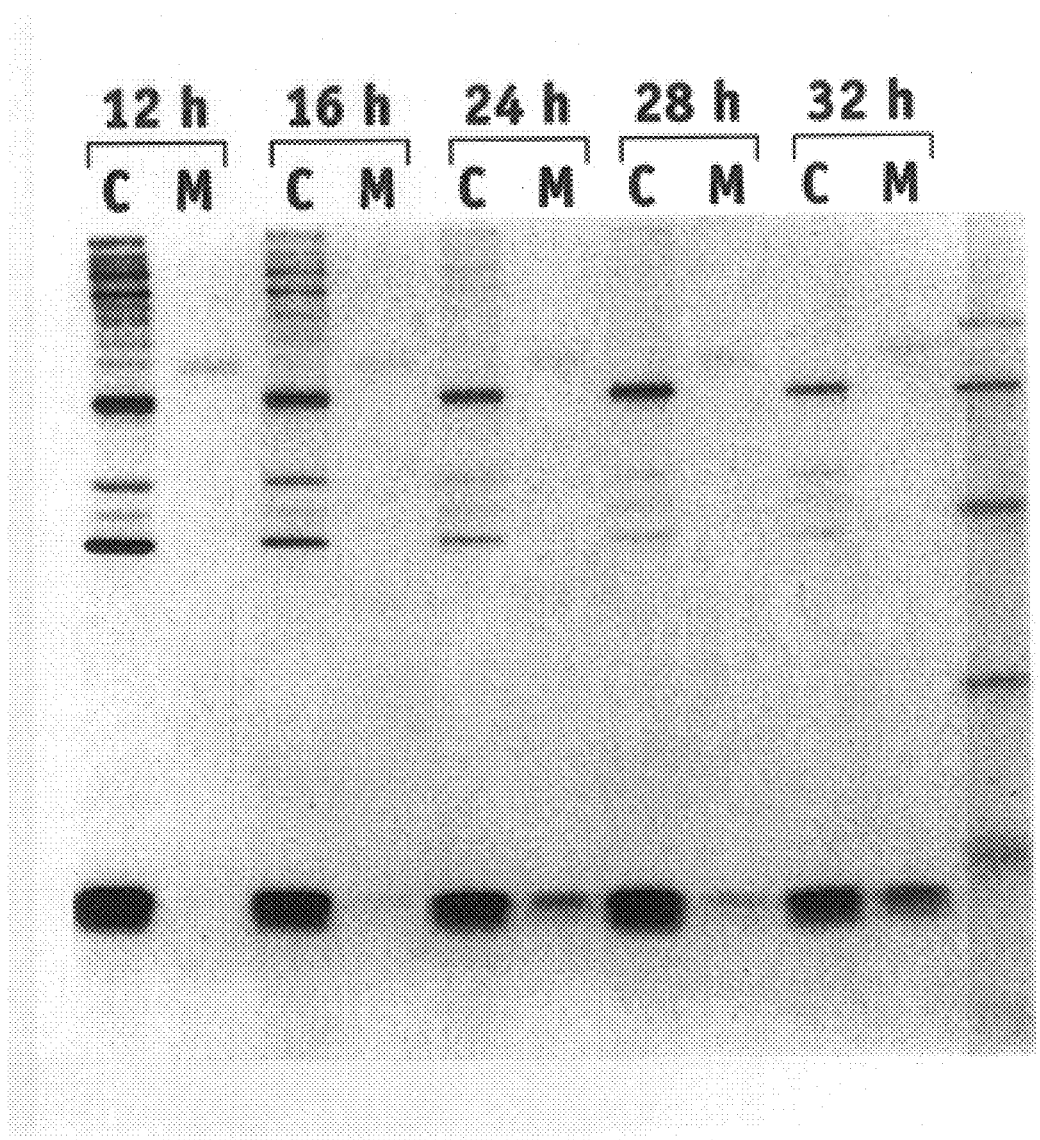

FIG. 19 is an autoradiogram of an immunoprecipitation with anti-IL-1 antibody following transfection of COS cells with a plasmid expressing IL-1.

Figure 20:
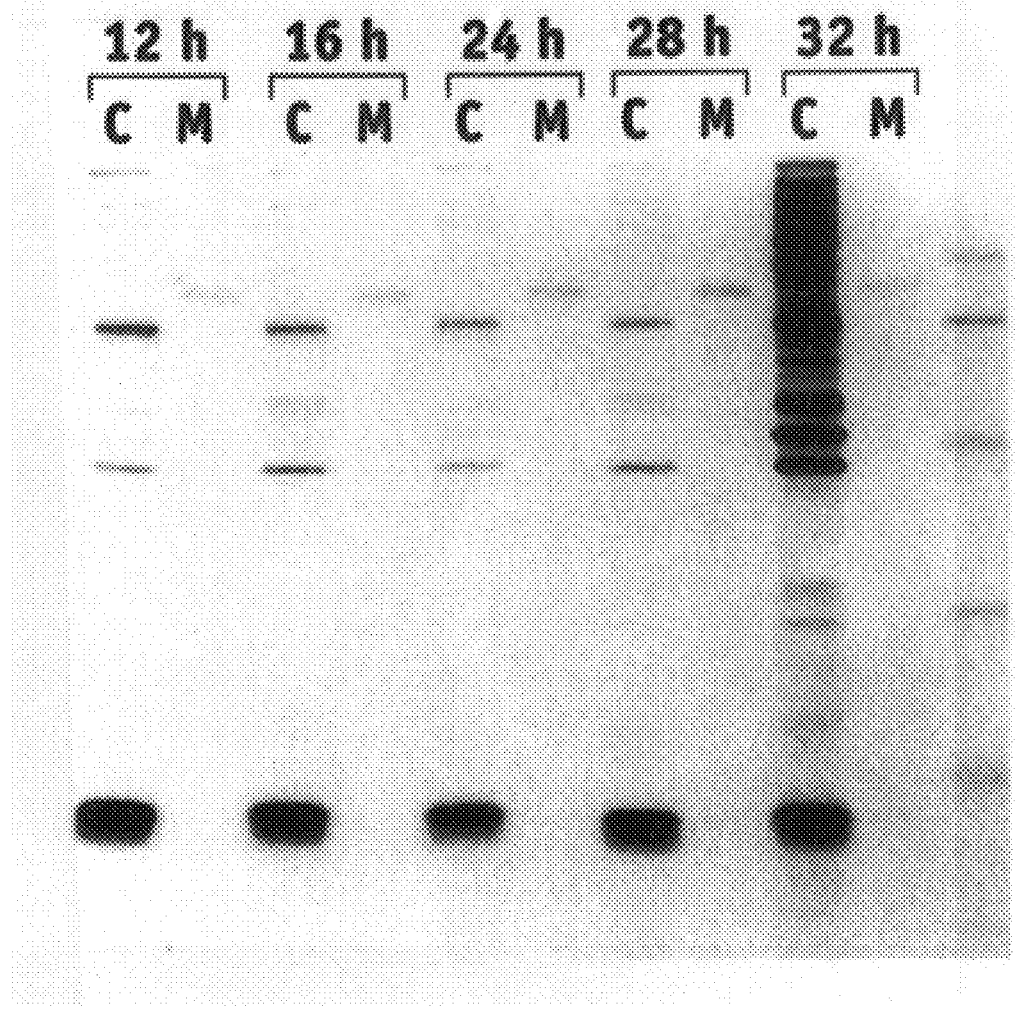

FIG. 20 is an autoradiogram of an immunoprecipitation with anti-IL-1 antibody following transfection of COS cells with a plasmid expressing IL-1 and treated with ouabain.

Figure 21:
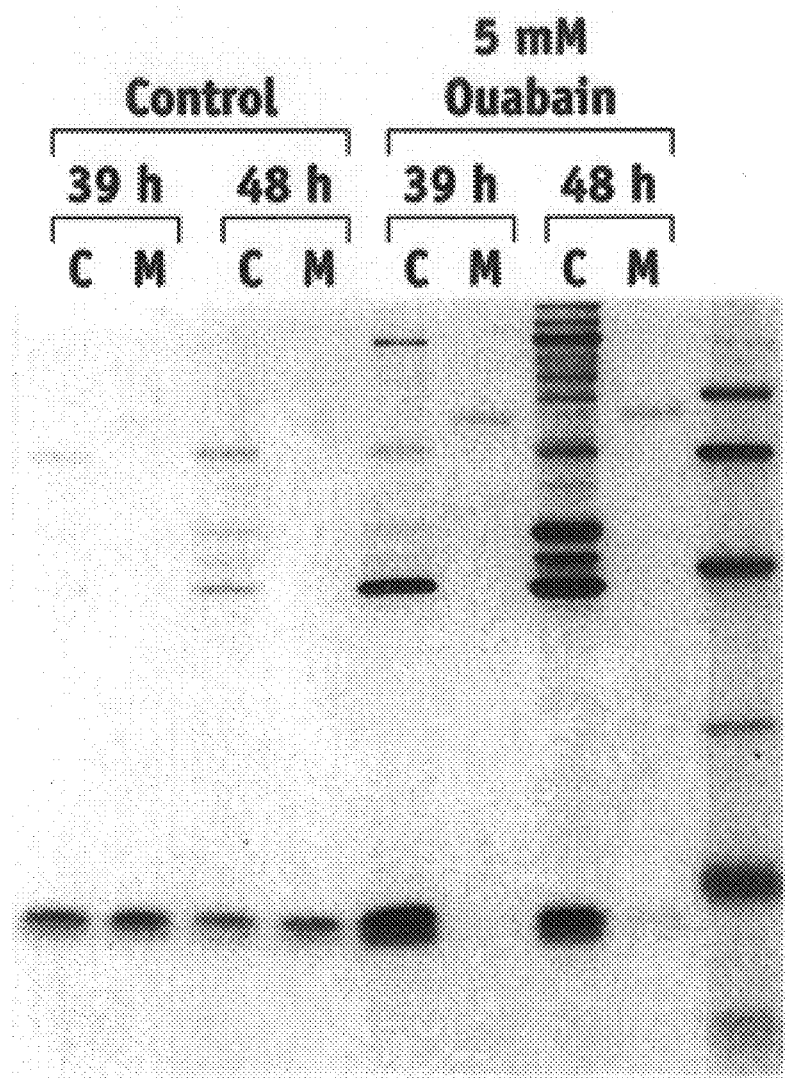

FIG. 21 is an autoradiogram of an immunoprecipitation with anti-IL-1 antibody following transfection of COS cells with a plasmid expressing IL-1 and either treated with ouabain or receiving no treatment.

Figure 22:
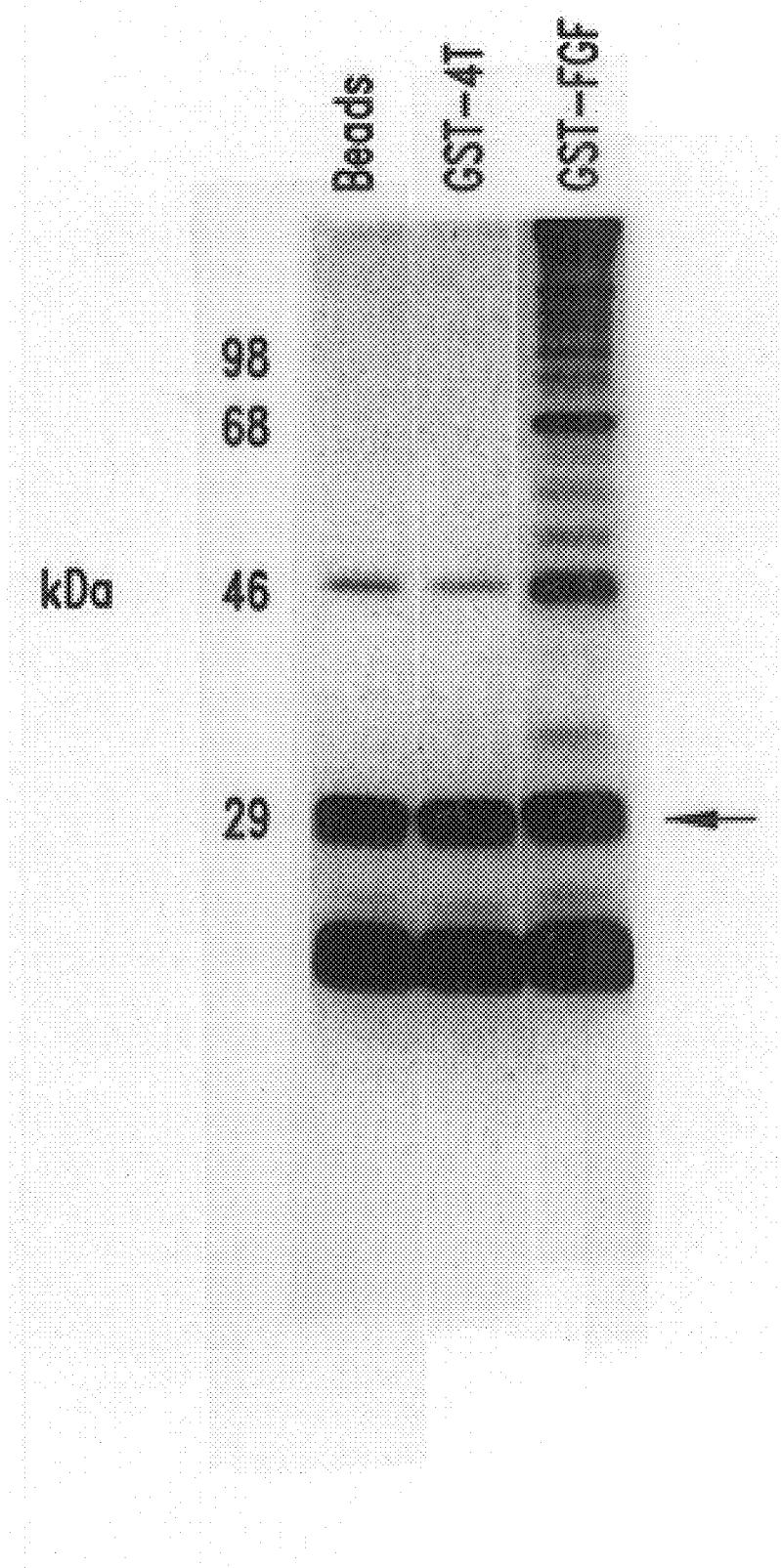

FIG. 22 is an autoradiogram of metabolically-labeled COS cell proteins that bind to an FGF-2/GST chimeric protein (GST-FGF). GST-4T is glutathione, beads are without any GST-based protein.

Figure 23:
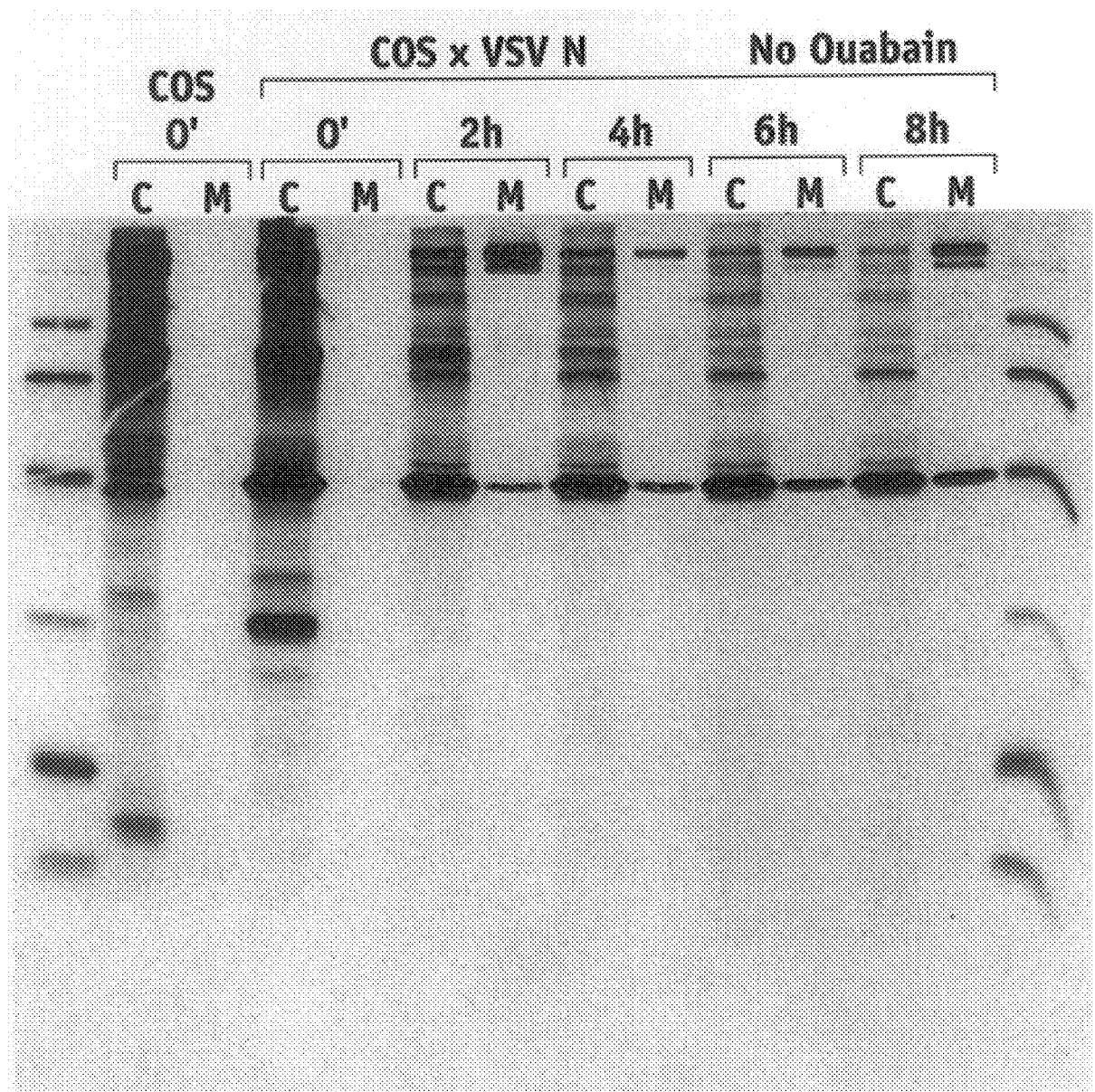

FIG. 23 is an autoradiogram of an immunoprecipitation with anti-VSV antibody following transfection of COS cells with a plasmid expressing VSV N protein.

Figure 24:
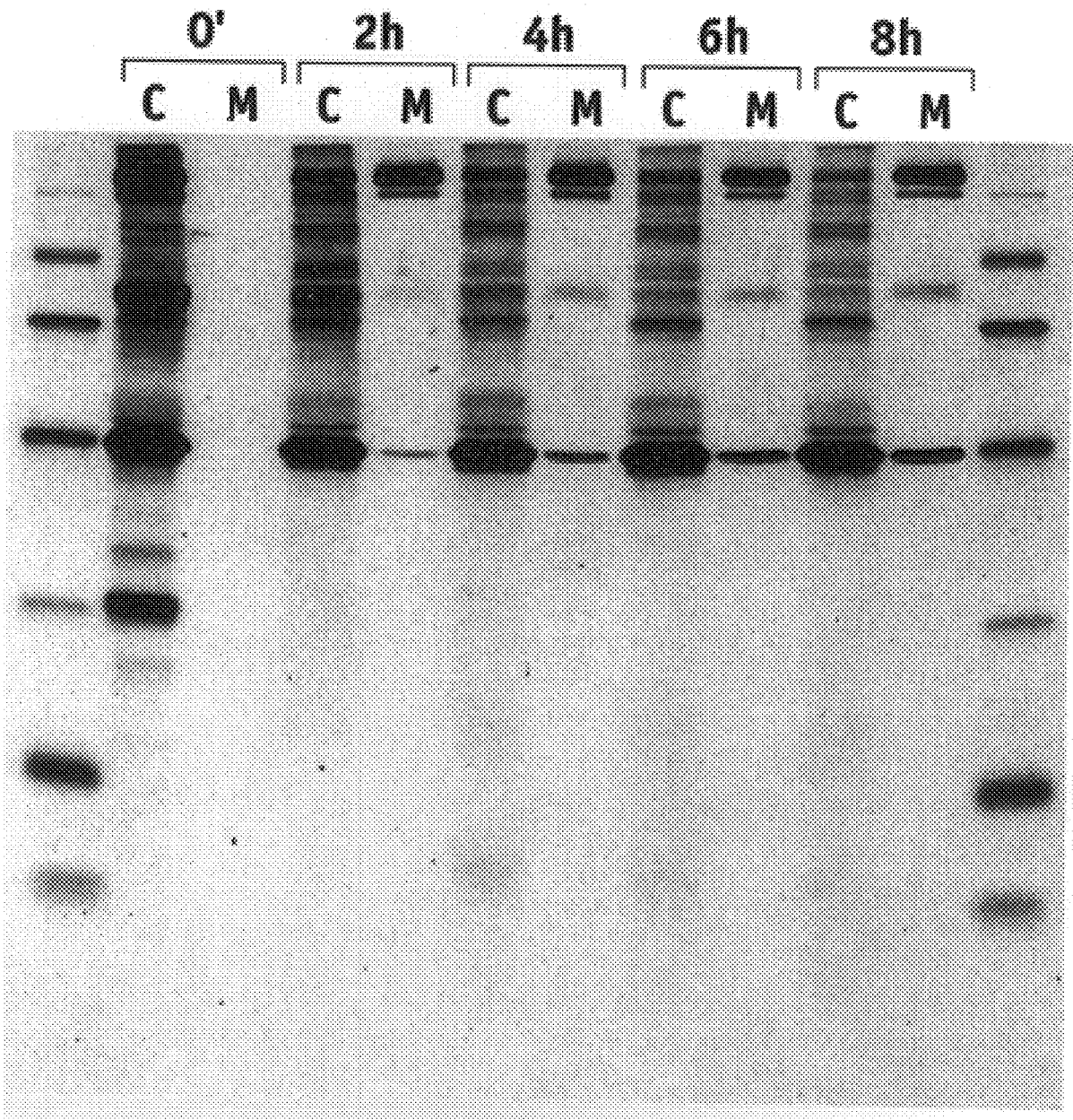

FIG. 24 is an autoradiogram of an immunoprecipitation with anti-VSV antibody following transfection of COS cells with a plasmid expressing VSV N protein and treated with ouabain.

Figure 25:
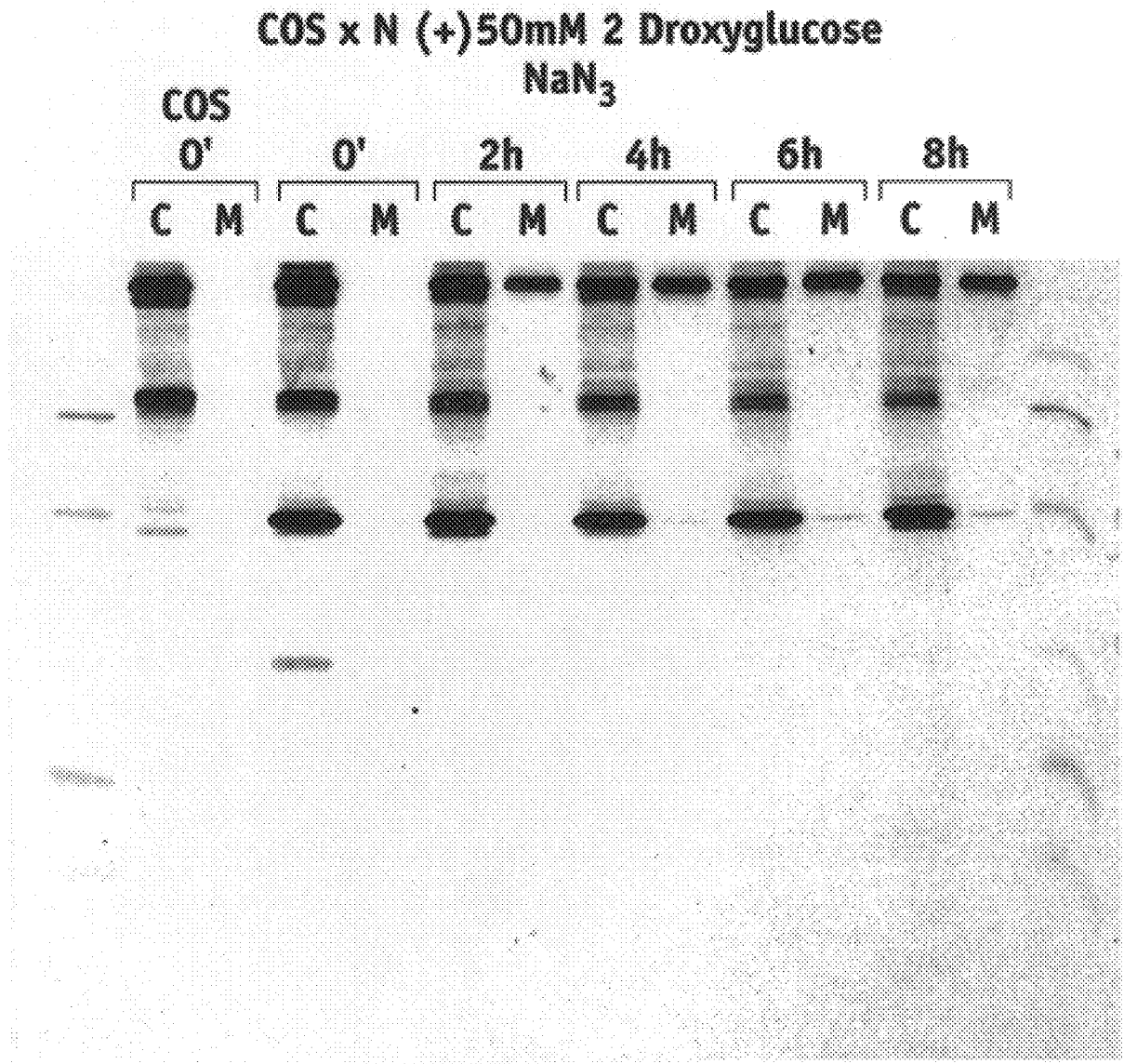

FIG. 25 is an autoradiogram of an immunoprecipitation with anti-VSV antibody following transfection of COS cells with a plasmid expressing VSV N protein and treated with 2-deoxyglucose and NaN$_3$.

Figure 26:
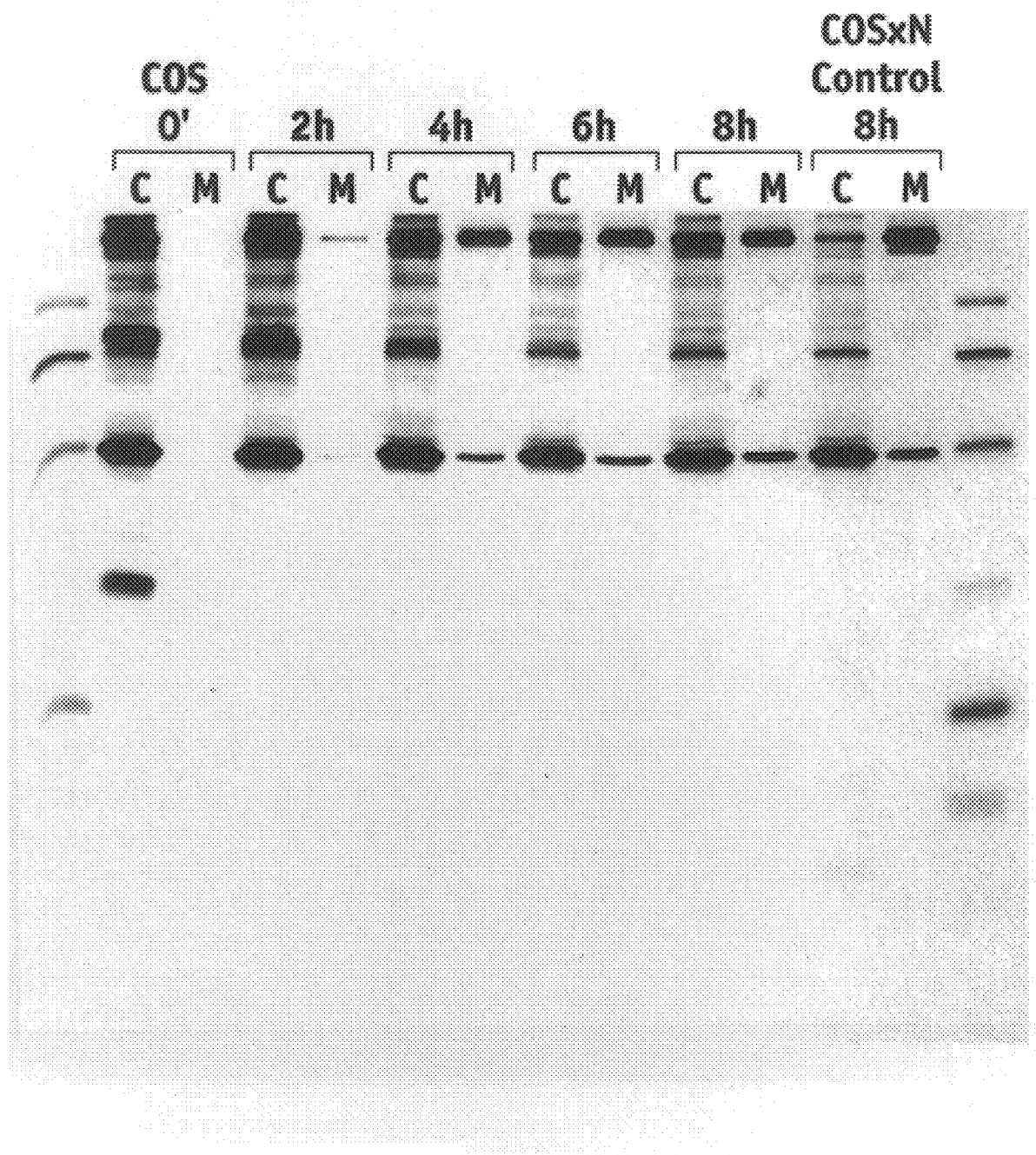

FIG. 26 is an autoradiogram of an immunoprecipitation with anti-VSV antibody following transfection of COS cells with a plasmid expressing VSV N protein and treated with brefeldin A.

Figure 27:
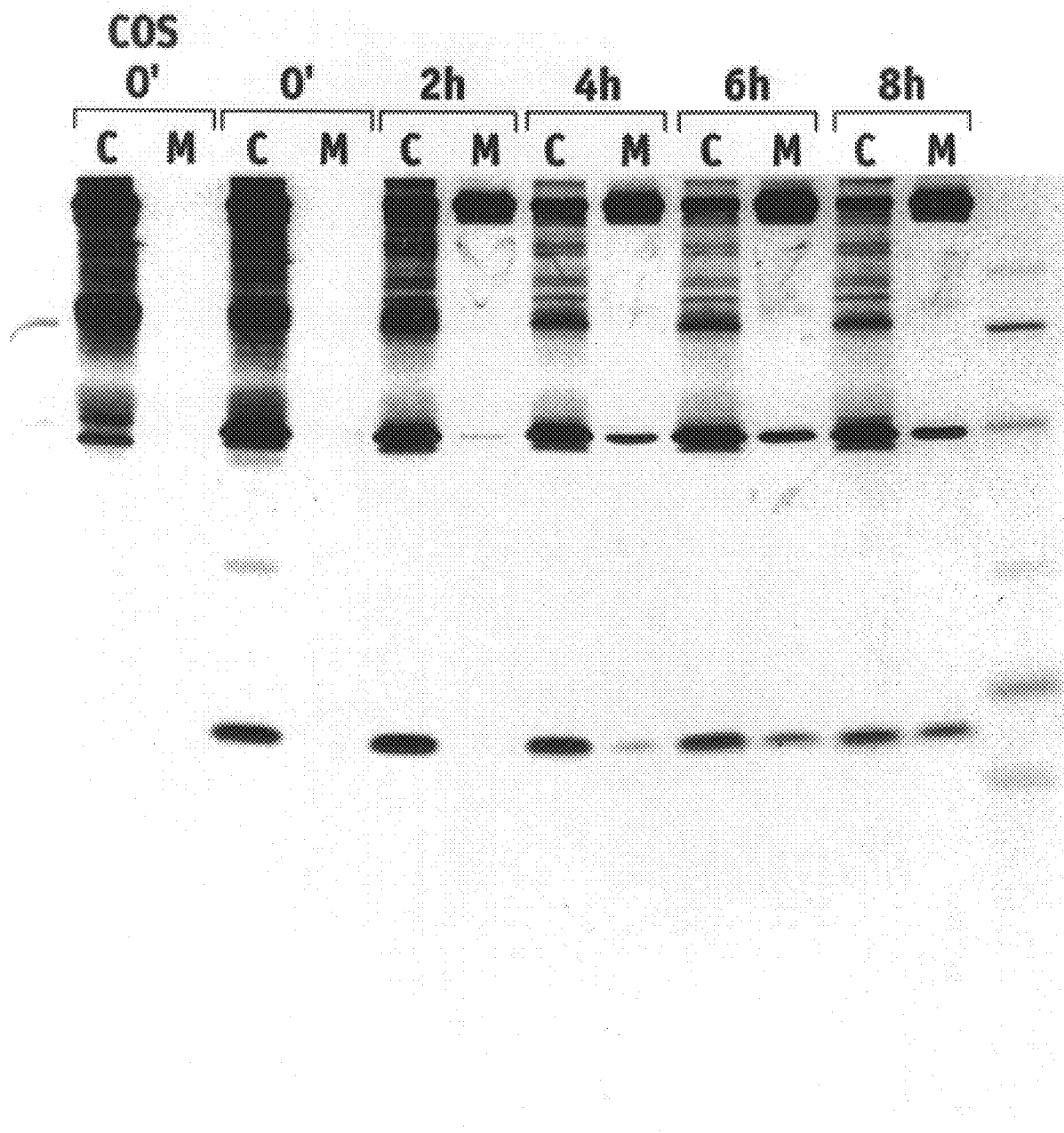

FIG. 27 is an autoradiogram of an immunoprecipitation with anti-FGF2 antibody following transfection of COS cells with plasmids expressing VSV N protein and FGF2.

Figure 28:
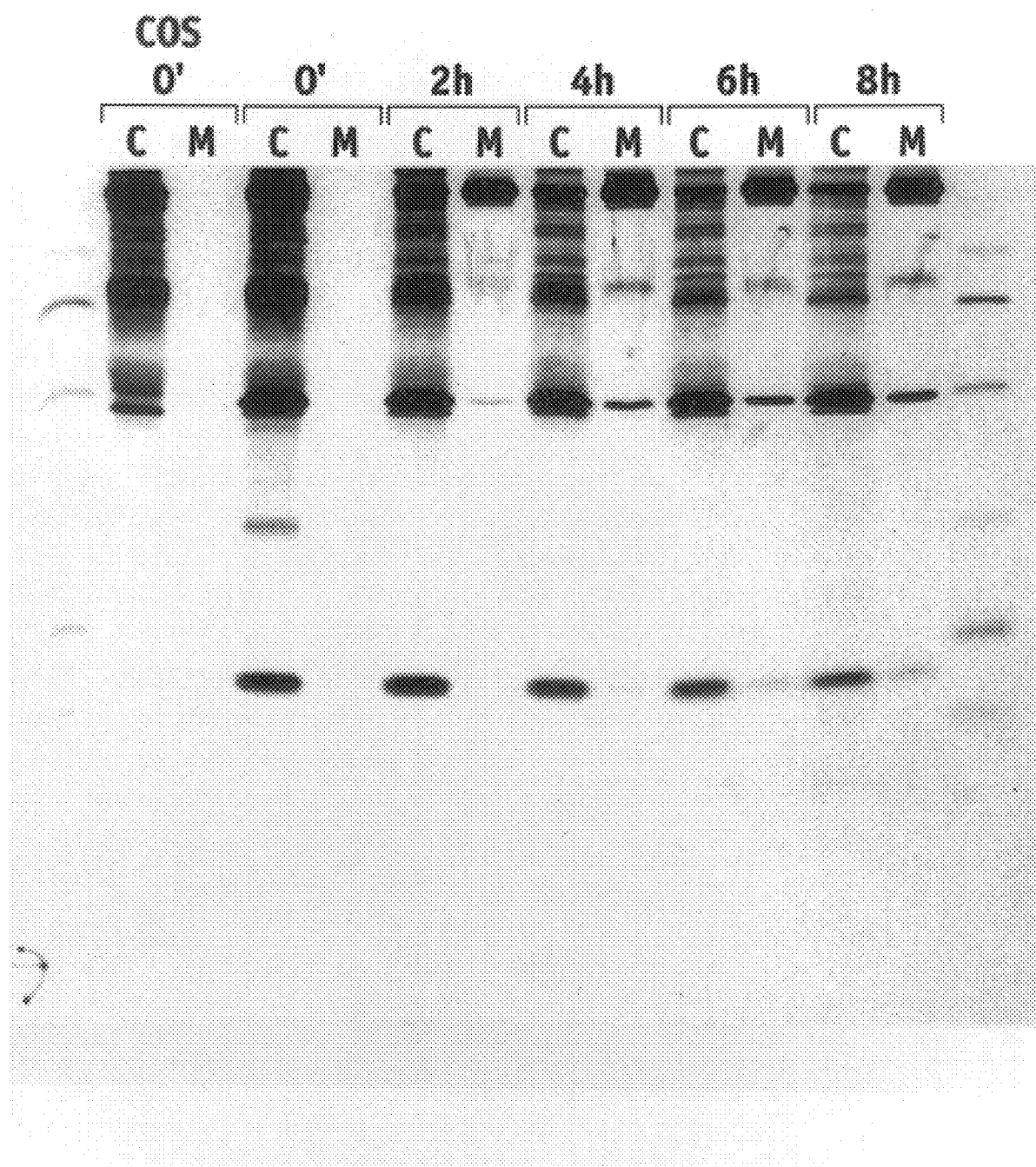

FIG. 28 is an autoradiogram of an immunoprecipitation with anti-FGF2 antibody following transfection of COS cells with plasmids expressing VSV N protein and FGF2 and treated with ouabain.

Figure 29C:
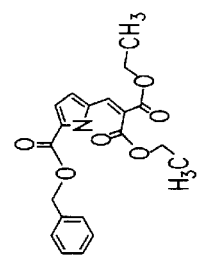

FIGS. 29A–29C present structures of small molecules that act as inhibitors of FGF-2 export.

SEQ ID NO:1 is a cDNA sequence of FGF-2.

SEQ ID NO:2 is a cDNA sequence of 18 kD form of FGF-2.

SEQ ID NO:3 is an amino acid sequence of 18 kD form of FGF-2.

SEQ ID NO:4 is a cDNA sequence of hCG.

SEQ ID NO:5 is an amino acid sequence of hCG.

SEQ ID NO:6 is a cDNA sequence of the precursor form of IL-1α.

SEQ ID NO:7 is an amino acid sequence of the precursor form of IL-1 α.

SEQ ID NO:8 is a cDNA sequence of the mature form of IL-1α.

SEQ ID NO:9 is an amino acid sequence of the mature form of IL-1α.

SEQ ID NO:10 is a cDNA sequence of the precursor form of IL-1β.

SEQ ID NO:11 is an amino acid sequence of the precursor form of IL-1β.

SEQ ID NO:12 is a cDNA sequence of the mature form of IL-1β.

SEQ ID NO:13 is an amino acid sequence of the mature form of IL-1β.

SEQ ID NO:14 is a nucleotide sequence of FGF 1.

SEQ ID NO:15 is an amino acid sequence of FGF1.

SEQ ID NO:16 is a nucleotide sequence of HIV Tat 72.

SEQ ID NO:17 is an amino acid sequence of HIV Tat 72.

SEQ ID NO:18 is a nucleotide sequence of HIV Tat 85.

SEQ ID NO:19 is an amino acid sequence of HIV Tat 85.

SEQ ID NO:20 is a forward amplification primer for the 18 kDa isoform of FGF-2.

SEQ ID NO:21 is a reverse amplification primer for the 18 kDa isoform of FGF-2.

SEQ ID NO:22 is a forward amplification primer for the wild type FGF-1.

SEQ ID NO:23 is a reverse amplification primer for the wild type FGF-1.

SEQ ID NO:24 is the N-terminal amino acid sequence recreated by the forward primer for wild type FGF-1.

SEQ ID NO:25 is a reverse amplification primer adding the HA epitope tag to FGF-1.

SEQ ID NO:26 is a reverse amplification primer adding the flg epitope tag to FGF-1.

SEQ ID NO:27 is a forward amplification primer for HIV Tat 72 or Tat 85.

SEQ ID NO:28 is a reverse amplification primer for wild type Tat 85.

SEQ ID NO:29 is a reverse primer encoding the C-terminal HA tag epitope.

SEQ ID NO:30 is a reverse primer for Tat 72.

SEQ ID NO:31 is a reverse primer encoding the C-terminal flg tag epitope.

SEQ ID NO:32 is a reverse primer for Tat 72 plus C-terminal HA-tag epitope.

SEQ ID NO:33 is a forward primer for IL-1α.

SEQ ID NO:34 is a reverse primer for IL-1α.

SEQ ID NO:35 is the flg peptide tag.

SEQ ID NO:36 is the influenza haemagglutinin peptide tag.

DETAILED DESCRIPTION OF THE INVENTION

As an aid to understanding the invention, certain definitions are provided herein.

"Leaderless protein" refers to a protein or polypeptide that is found in an extracellular environment but lacks a canonical leader sequence. A leader sequence mediates translocation into the ER and is recognized by signal recognition proteins (SRP). Proteins in the extracellular environment include secreted proteins found in extracellular spaces, as well as proteins that are membrane bound, but not as an integral membrane protein. The prototypic leader sequence has an amino-terminal positively charged region, a central hydrophobic region, and a more polar carboxy-terminal region (see, von Heijne, *J. Membrane Biol.* 115:195–201, 1990). Leaderless proteins include FGF-1, FGF-2, interleukin-1a, interleukin-1β, vas deferens protein, platelet-derived endothelial cell growth factor (PD-ECGF), ciliary neurotrophic factor (CNTF), thymosin, parathymosin, 14.5 kDa lectin (L14), transglutaminase, thioredoxin-like protein, sciatic nerve growth-promoting activity, factor XIIIa, mammary-derived growth inhibitor, galectin, rhodanase, and HIV tat. Within the context of the invention, leaderless proteins include naturally occurring proteins as well as proteins that are engineered to lack a leader sequence, but are exported. The terms "signal sequence," "leader peptide," and "leader sequence" are used interchangeably herein.

"Export" of a protein refers to a metabolically active process of transporting a translated cellular product to the extracellular spaces or to the cell membrane by a mechanism other than by a leader sequence.

Leaderless Proteins

As noted above, leaderless proteins are proteins that arrive in the extracellular environment, including at or in the cell membrane, but lack a signal. sequence, which functions to mediate translocation of a protein into the endoplasmic reticulum (ER) by SRP. Typically, these leaderless proteins are initially identified because their primary translation product lacks a canonical hydrophobic leader or signal sequence, which is usually located at the N-terminus of the primary translation product. The leader sequence is used in the transport process through the ER/Golgi. A canonical leader sequence has three distinct domains: an amino-terminal positively charged region approximately 1–5 residues long; a central, hydrophobic region approximately 7–15 residues long; and a more polar carboxy-terminal domain approximately 3–7 residues long (von Heijne, supra). The hydrophobic central region is critical.

Several leaderless proteins have been identified by virtue of their location in the extracellular environment, transport by a mechanism other than through the ER/Golgi, and lack of a leader sequence. Such proteins include IL-1α (SEQ ID NOS: 6, 7 and 8, 9; precursor, mature forms), IL-1β (SEQ ID NOS: 10, 11, 12, and 13;

precursor; mature forms), FGF-1, FGF-2 (SEQ ID NOS:1–3; cDNA, 18 kD form), HIV tat, PD-ECGF (platelet-derived endothelial cell growth factor), CNTF (ciliary neurotrophic factor), sciatic nerve growth-promoting activity, vas deferens protein, transglutaminase, L-14 lectin, factor XIIIa, thioredoxin-like protein (ADF), thymosin, parathymosin, mammary-derived growth inhibitor, galectin, HIV tat, and rhodanase.

Other leaderless proteins that are exported may be identified by a two-part assay: (1) identification of the protein in extracellular spaces, including at the membrane, and (2) brefeldin-resistant export. A preliminary assessment to identify candidate leaderless proteins may be made by inspection of the amino acid sequence of the primary translation product. Comparison of the amino-terminal sequence with other known leader sequences or identification of the prototypic pattern sequence, as described herein (von Heijne, supra), provides a means to classify potential leaderless proteins. As discussed above, leader sequences are approximately 15–25 amino acids long and contain at minimum a central region of 7–15 hydrophobic residues, such as leucine, isoleucine, valine, glycine, phenylalanine, methionine, threonine, serine, proline, cysteine, alanine, tyrosine, and tryptophan. Any primary translation sequence of a protein that lacks such a sequence is a candidate for an exported leaderless protein.

As noted above, identification of a protein as a leaderless protein rests in the two-part assay, discovery of the protein in the extracellular environment and brefeldin-resistance.

The first assay is performed to detect the protein extracellularly. For this assay, test cells expressing a leaderless protein are necessary. Either the test cells may naturally produce the protein or preferably produce it from a transfected expression vector. Test cells preferably normally express the protein, such that transfection merely increases expressed levels. Thus, for FGF-2 expression, COS cells are preferred for transfection, and for expression of IL-1, p388D1 cells are preferred. When one is assaying virally-derived proteins, such as HIV tat, if the test cells do not "naturally" produce the protein, they may readily be transfected using an appropriate vector, so that the test cells will express the desired protein, as those of skill in the art will appreciate.

Following expression, the protein is detected by any one of a variety of well known methods and procedures. Such methods include staining with antibodies ill conjunction with flow cytometry, confocal microscopy, image analysis, immunoprecipitation of cell medium, Western blot of cell medium, ELISA, 1- or 2-D gel analysis, HPLC, or bioassay. A convenient assay for initial screening is ELISA. Any candidate may be confirmed by one of the other assays, preferably by immunoprecipitation of cell medium following metabolic labeling. Briefly, cells expressing the candidate leaderless protein are pulse labeled for 15 minutes with $^{35}$S-methionine and/or $^{35}$S-cysteine in methionine and/or cysteine free medium and chased in medium supplemented with excess methionine and/or cysteine. Media fractions are collected and clarified by centrifugation, such as in a microfuge. Lysis buffer containing 1% NP-40, 0.5% deoxycholate (DOC), 20 mM Tris, pH 7.5, 5 mM EDTA, 2 mM EGTA, 10 nM PMSF, 10 ng/ml aprotinin, 10 ng/ml leupeptin, and 10 ng/ml pepstatin is added to the clarified medium. Antibody to the candidate leaderless protein is added and following incubation in the cold, a precipitating second antibody or immunoglobulin binding protein, such as protein A-Sepharose® or GammaBind™-Sepharose®, is added for further incubation. In parallel, as a control, a vector encoding a cytosolic protein is co-transfected and an antibody to the cytosolic protein is used in immunoprecipitations. Immune complexes are pelleted and washed with ice-cold lysis buffer. Complexes are further washed with ice-cold IP buffer (0.15 M NaCl, 10 mM Na-phosphate, pH 7.2, 1% DOC, 1% NP-40, 0.1% SDS). Immune complexes are eluted directly into SDS-gel sample buffer and electrophoresed in SDS-PAGE. The percentage of acrylamide will depend upon the molecular weight of the leaderless protein. The gel is processed for fluorography, dried and exposed to X-ray film. Proteins that are expressed at higher levels in medium as compared to the cytosolic protein control are also tested for brefeldin resistant export.

Brefeldin-resistance is measured in cells expressing a leaderless protein. Briefly, cells are transfected with an expression vector directing expression of the leaderless protein. Approximately 2 days later, the transfected cells are metabolically pulse-labeled for 15 minutes or longer with $^{35}$S-methionine and $^{35}$S-cysteine in methionine and cysteine free media. Label is removed, and the cells are further incubated in medium containing 5–15 µg/ml brefeldin A. For quantitation of FGF-2 export, 25 µg/ml heparin is added to the chase medium. Lack of statistically significant reduction in leaderless protein export indicates that protein export is brefeldin A resistant. Alternatively, other compounds that disrupt Golgi-mediated secretion may be used instead of brefeldin.

Novel leaderless proteins that are exported may also be identified in an expression library. In such a method, a cDNA library from a tissue or cell source is constructed in a vector such that a fusion protein is generated with a reporter protein or peptide tag. The reporter or tag can be any protein that allows convenient and sensitive measurement in conditioned media and does not interfere with the export of the fusion protein. For example, β-galactosidase and FLAG peptide may be used. Furthermore, multiple tags may be used to allow detection by a sandwich assay. In general, the vector will use a strong promoter to drive expression of the cDNA-fusion genes and an appropriate origin of replication for the host cell. The library is transfected into host cells (e.g., COS cells) by any of the methods described herein or other known methods. Any host cell that is capable of non-classical export and is compatible with the vector may be used. Host cells can include animal cells, such as COS, CHO, yeast, and others. To facilitate recovery of particular cDNAs, the library is transfected at a low multiplicity, such as 10 recombinant vectors per cell. Cell supernatant is assayed for the presence of the reporter or tag protein. In addition, brefelden-resistant export is assessed to confirm that the export is through a pathway other than Golgi/ER. Cells expressing a protein with brefeldin-resistant export are isolated, and the vector is amplified or isolated and propagated. The vector is then transfected into host cells again at low multiplicity and the selection procedure repeated. Each round of transfection and selection should enrich for an exported cDNA. The positive cDNAs may be characterized, such as for DNA sequence, tissue expression patterns, and the like.

Transport molecules

This invention provides inhibitors of leaderless protein export wherein the inhibitor interferes with the binding of a leaderless protein to a transport molecule. The transport molecule may be a single protein, a complex of proteins, or part of a larger complex. For example, as described herein, the α subunit of the multi-unit $Na^+/K^+$ ATPase is a molecule that binds to leaderless proteins.

As shown herein, the $Na^+/K^+$ ATPase mediates transport of leaderless proteins. This ATPase is an integral membrane protein of eukaryotic cells and is responsible for the transport of sodium and potassium ions across the cell membrane using ATP as the driving force. The $Na^+/K^+$ ATPase consists of an α, β, and δ subunit.

In mammals, there are at least four known isoforms of the α subunit and three known isoforms of the β subunit. The α1 subunit is fairly ubiquitously expressed, being detected in virtually all rat tissues examined (Shyjan and Levenson, Biochem. 28:4531, 1989). As shown herein, FGF-2 and IL-1 interact with the α1 subunit (see, Examples) as visualized by co-immunoprecipitation of the two proteins using anti-FGF-2 or anti-IL-1 and anti-α1 subunit antibodies. As well, export is sensitive to treatment of cardenolides, such as ouabain. Verification of the interaction is obtained by showing that co-overexpression of the α1 subunit dramatically slows the rate of FGF-2 export compared to control transfected cells. In addition, FGF-2 and IL-1 are shown by co-immunoprecipitation to interact with the α2 and α3 subunits, isoforms of the α subunit. Furthermore, overexpression of the α2 or α3 subunits also slows the rate of FGF-2 export.

Other ion channels may function as transport molecules or as part of a, transport complex. Well known ion channels include, in addition to $Na^+/K^+$ ATPase, $Ca^+$ ATPase, $H^+/K^+$ ATPase, $Na^+$ channel, $Cl^-$ channel and $K^+$ channel. The involvement of these channels in transport of leaderless proteins may be assessed by treating cells exporting one or more leaderless proteins with an inhibitor of channel activity. Some known inhibitors of these channels are listed below.

| Na$^+$/K$^+$ ATPase Inhibitors | Ca$^+$ ATPase Inhibitors | H$^+$/K$^+$ ATPase Inhibitors | Na$^+$ Channel Blockers | Cl$^-$ Channel Blockers | K$^+$ Channel Blockers |
|---|---|---|---|---|---|
| Ouabain | Cyclopiazonic Acid | Bafilomycin | Amiloride | N-Phenylanthranillic Acid | Diazoxide |
| Ouabagenin | Nifedipine | | Benzamil HCl | R (+)-IAA-94 | Gilbenclamide |
| Digoxin | Verapamil | | | 5-Nitro-2-(3-phenyl-propyl-amino-benzoic acid) | |
| Digoxigenin Digitoin Digitoxigenin | Trifluroperazine Thapsigargin | | | | |

These inhibitors may be assayed for their ability to inhibit export of any of the leaderless proteins, such as FGF-2, IL-1, and HIV tat. In an exemplary assay, a cell line that exports a leaderless protein (e.g., THP-1 cells export IL-1β) is seeded in 48 well tissue culture plates. When export of the protein is induced (e.g., by addition of LPS for IL-1β) or when the cells have recovered, a panel of ion channel inhibitors is added to individual wells for approximately 4–24 hours. At the end of this incubation period, cell supernatant is removed and assayed by any of the assays described herein for the leaderless protein. An inhibitor that decreases the amount of export identifies an ion channel as a candidate transport molecule.

Additional transport molecules of leaderless proteins may be identified by a variety of methods, including isolation after binding to a leaderless protein. Briefly, cells expressing and exporting a leaderless protein are metabolically labeled for a short period of time. The label is optionally chased and cell and media fractions ire immunoprecipitated with anti-leaderless protein antibodies. The antibodies may be monoclonal, a mixture of monoclonal antibodies, or polyclonal antibodies. Immune complexes are collected and fractionated by PAGE. Labeled proteins precipitated by anti-leaderless protein antibodies, but not by control antibodies, may be isolated and subjected to analysis and subsequent identification. In general, the protein will be subjected to partial amino acid sequence analysis and either a sequence match with a known protein is made, or a clone containing the sequence is isolated by standard recombinant DNA technologies and cloning procedures (e.g., hybridization of a degenerate probe on a library, generate antibodies and immunoscreen an expression library, or amplification of the sequence). Verification of a specific interaction may be made by one of several methods, including overexpression of the transport molecule or mutants of the molecule(s) and demonstration that export is altered, co-immunoprecipitation of the transport and leaderless protein using anti-transport molecule antibodies, in vitro interactions assayed by Western blots, ELISA, and the like, or other methods.

Alternatively, additional transport molecules may be identified by other methods, such as yeast two-hybrid system or transfection of a leaderless fusion protein followed by isolation of the fusion protein. Briefly, in a two-hybrid system, a fusion of a DNA-binding domain-leaderless protein (e.g., GAL4-FGF-2 fusion) is constructed and transfected into a cell containing a GAL4 binding site linked to a selectable marker gene. A library of cDNAs fused to the GAL4 activation domain is also constructed and co-transfected. When the cDNA in the cDNA-GAL4 activation domain fusion encodes a protein that interacts with FGF-2, the selectable marker is expressed. Cells containing the cDNA are then grown, the construct isolated and characterized. Verification of specific interaction is made as described above.

In another method to identify transport proteins, a fusion protein is constructed comprising a leaderless protein or fragment thereof and a tag peptide sequence (e.g., glutathione-S-transferase) that is bound by an antibody or other molecule (e.g., glutathione). A vector encoding the fusion protein is transformed into bacteria. The fusion protein is purified. For example, a GST (glutathione-S-transferase) FGF-2 fusion protein in pGEX-4T-3 (Pharmacia, Uppsala, Sweden) is induced by IPTG and purified using glutathione-beads (see, Kaelin et al., Cell 64:521, 1991). Cells that express transport proteins may be metabolically labeled. Extracts of the cells are incubated with GST-FGF2 charged glutathione-Sepharose beads. Alternatively, the fusion protein may be immunoprecipitated or the like. Unbound protein is washed away, and bound protein is eluted. The bound proteins may be further fractionated by gel electrophoresis, for example. The bound proteins may then be used for raising antibodies, amino acid sequence analysis, and in vitro tests as described herein. Clones encoding the bound proteins may be isolated by any one of a variety of standard methods, including immuno-screening of an expression library, probe hybridization where the probe is based on a partial amino acid sequence, and other known methods.

In another method, membrane components of the export pathway are identified. Briefly, membrane preparation are prepared according to well-known, methods (e.g., Biomembranes, *Methods in Enzymology vol 172*; Klein et al., *Growth Factors* 13:219, 1996). To reduce non-specific association of the leaderless protein with proteoglycans, cells can be grown in medium containing 25 mM sodium chlorate (Guimond et al., *J. Biol. Chem.* 268: 23906, 1993). Isolated membranes are incubated with the leaderless protein, such as FGF-2 and solubilized. Complexes of FGF-2/membrane components are presipitated with anti-FGF-2 antibodies. Optionally, prior to immune precipitation, membranes can be crosslinked, such as with a reversible crosslinking agent. Characterization of the components by SDS-PAGE analysis allows size determination. Proteins may be visualized by autoradiography (if cells or membranes are radiolabeled) or by a stain (e.g., Coomassie blue, silver stain). Isolation of protein components may be subjected to amino acid sequence analysis to facilitate molecular cloning.

Yet another method for identifying and isolating transport proteins is by virtue of homology or sequence similarity to export proteins in other organisms, such as yeast and bacteria. For example, export proteins in yeast are known (NCE2, Cleves and Kelly, *J. Cell Biol.* 133:1017, 1996, GenBank Accession No. U 41659; NCE3, Cleves and Kelly, ibid., GenBank Accession No. U 52369; and NCE1, Cleves and Kelly, ibid., GenBank Accession No. U 41658). Non-stringent hybridization of the yeast genes to mammalian cDNA libraries can be used to identify similar gene sequences (see Ausubel et al., *Current Protocols in Molecular Biology*, Greene Publishing, NY, 1995). These sequences can be shown to be homologous genes by virtue of interaction with leaderless proteins or conferring transport capability on a cell or by other methods described herein.

In addition to the yeast export proteins, a secretion system in *E. coli,* Yersinia, and Shigella transport leaderless proteins (Salmond and Reeves, *TIB* 18:7–12, 1993) may be used to screen by sequence similarity. At least seven proteins responsible for export in *E. coli* have been identified (Jarvis et al., *Proc. Natl. Acad. Sci. USA* 92:7996, 1995; Bost and Belin, *EMBO J.* 14:4412, 1995). DNA probes from the locus hybridize to genomic DNA of pathogens from other genera (McDaniel et al., *Proc. Natl. Acad. Sci. USA* 92:1664, 1995). DNA probes from these genes and from the Ysc genes of Yersinia and Mxi and Spa from Shigella may be used to detect homologues in other species, including mammalian species.

In preferred embodiments, subdomains of transport proteins are used in assays for identifying inhibitors of the interaction with a leaderless protein. For transport proteins that are transmembrane bound, both a cytosolic and an anchored subdomain are constructed. Other methods to redirect the protein to a different subcellular fraction may also be used. Merely by way of example, an $\alpha 1$ subunit lacking a transmembrane domain(s) is constructed in an expression vector. An FGF-2 construct is co-transfected and the interaction between FGF-2 and the $\alpha 1$ fragment is assessed. Alternatively, $\alpha 1$ fragments may be anchored in the membrane. Because generally $\alpha 1$ does not insert into the plasma membrane of animal (vertebrate animals) cells in the absence of a $\beta 1$ subunit, a fusion protein construct to direct $\alpha 1$ to the cell surface is made. Briefly, a fusion protein, including the transmembrane region of another protein; such as VSV-G, is fused to the N-terminus of $\alpha 1$ and various deletions and truncations of $\alpha 1$. To assist in detection of $\alpha 1$ in the membrane an extracellular region of a readily assayed protein, such as hCG (human chorionic gonadotropin), may be fused to the construct adjacent to the VSV-G transmembrane. Other reporter genes may be interchanged as long as the gene product is readily assayed (e.g., by antibody, staining, enzyme assays). hCG may be detected by antibody staining. When $\alpha 1$ is verified to be inserted into the membrane, interaction between FGF-2 and $\alpha 1$ is assessed and export of FGF-2 is assayed by methods described herein.

Inhibitors

Candidate inhibitors may be isolated or procured from a variety of sources, such as bacteria, fungi, plants, parasites, libraries of chemicals, random peptides or the like. Potential inhibitors include compounds known to inhibit angiogenesis, inflammation, or other specific functions of leaderless proteins. For example, inhibitors of angiogenesis include Adriamycin, etoposide, ansacrino, camptothecin, $\epsilon$-(4-hydroxy-1-naphthalenyl)-2-proponoic acid derivatives, 2,5-di-test-butylhydroquinone, amiloride and derivatives, aurintricarboxylic acid, captopril, dioxopiperazines, methylprednisolone, suramin, and minocycline. Inhibitors of inflammation include 8-hydroxyquinoline, choline chloride, cyclopiazonic acid, indoprofen, monensin, nicotine, Mycostatin, verapamil, and thiamine. These and other inhibitors may be pleiotropic in their action and, as such, may be tested for inhibition of export of many or all of the leaderless proteins. In addition to inhibitors with known function, other candidate inhibitors of protein export may be procured from chemical libraries, small molecule libraries, plants, fungi and the like using assay methods as described herein. For example, inhibitors identified from small molecule and chemical libraries include those identified in FIGS. 29A–29C herein, and derivatives and analogues thereof.

Inhibitors and potential inhibitors useful as disclosed herein also include derivatives, analogues and mimics of molecules and compounds with identified and potential inhibitory effects. For example, derivatives, analogues and mimics of compounds known to inhibit angiogenesis, inflammation, or other specific functions of leaderless proteins are inhibitors or potential inhibitors within the context of the present invention. To cite a more specific example, for the purpose of illustration, derivatives, analogues and mimics of Adriamycin, Mycostatin, and atebrine are inhibitors and/or potential inhibitors within the scope of the present invention.

In preferred embodiments, inhibitors interfere in the interaction of a leaderless protein and its transport protein or proteins. The inhibitor may act by preventing binding of the leaderless protein and the transport protein, cause dissociation of the bound leaderless and transport proteins, or other mechanism. The inhibitor may act directly or indirectly. For example, inhibition of the binding of $\alpha 1$, $\alpha 2$, or $\alpha 3$ with FGF-2 or IL-1 will reduce or eliminate protein export. Such an inhibitor generally acts intracellularly. In contrast, cardenolides (i.e., cardiac glycosides and aglycone derivatives) act extracellularly and inhibit export of FGF-2 but may not inhibit the interaction of FGF-2 with $\alpha 1$ subunit.

Inhibitors should have a minimum of side effects and are preferably non-toxic. For some applications, inhibitors that can penetrate cells are preferred. Inhibitors should be specific for export and not merely inhibit metabolism, such as $NaN_3$.

Assays For Detecting Inhibition of Export of Leaderless Proteins

Inhibitors of export of a leaderless protein are identified by an assay, such as the assays described herein. Briefly, in a preferred assay, a cell expressing a leaderless protein is treated with the candidate inhibitor and the amount of leaderless protein detected as an extracellular protein is compared to the amount detected without treatment.

Within the context of the present invention, an inhibitor must satisfy three criteria: (1) inhibit export of a leaderless protein; (2) not inhibit export of a secreted protein with a leader sequence; and (3) not promote expression of a cytosolic protein in the extracellular environment. Generally, test compounds will be assayed first for inhibiting export of a leaderless protein. Successful inhibitors will be further assayed for the other desired characteristics. Appropriate controls may be used to distinguish true and false positives or negatives.

In any of the assays described herein, a test cell may express the leaderless protein naturally or following introduction of a recombinant DNA molecule encoding the protein. Transfection and transformation protocols are well known in the art and include $CaPO_4$-mediated transfection, electroporation, infection with a viral vector, DEAE-dextran mediated transfection and the like. Recombinant expression of the leaderless protein is preferred. As an alternative to the leaderless proteins described above, chimeric leaderless proteins (i.e., fusion of a leaderless protein with another protein or protein fragment), or protein sequences engineered to lack a leader sequence may be used. In similar fashion, the secreted protein and cytosolic protein may be naturally expressed by the host cell or expressed following transfection of a vector encoding the protein. The host cell can also express the leaderless protein as a result of being diseased, infected with a virus, and the like. Secreted proteins that are exported by virtue of a leader sequence are well known and include, human chorionic gonadatropin (hCGα) (SEQ ID NO:3), growth hormone, hepatocyte growth factor, transferrin, nerve growth factor, vascular endothelial growth factor, ovalbumin, and insulin-like growth factor. Similarly, cytosolic proteins are well known and include. neomycin phosphotransferase, β-galactosidase, actin and other cytoskeletal proteins, and enzymes, such as protein kinase A or C. The most useful cytosolic or secreted proteins are those that are readily measured in a convenient assay, such as ELISA. The three proteins (leaderless, secreted, and cytosolic) may be co-expressed naturally, by co-transfection in the test cells, or transfected separately into separate host cells. Furthermore, for the assays described herein, cells may be stably transformed or express the protein transiently.

The leaderless protein expressed from a recombinant vector may be native protein, a variant, including an allele, or a fusion protein designed to aid detection of the protein. For example, a fusion protein of FGF-2 and a peptide tag may be constructed. The peptide tag is a short sequence, usually derived from a native protein, which is recognized by an antibody or other molecule. Such peptide tags include FLAG®, Glu-Glu tag (Chiron Corp., Emeryville, Calif.) KT3 tag (Chiron Corp.), T7 gene 10 tag (Invitrogen, La Jolla, Calif.), T7 major capsid protein tag (Novagen, Madison, Wis.), and HSV tag (Novagen). Other, similar systems may be used as long as the fusion protein containing the tag is exported. Besides tags, other types of proteins or peptides may be used. For example, glutathione-S-transferase or a sequence specifying an enzymatic activity may be fused to the leaderless protein. Such enzymes include β-galactosidase, thioredoxin, alkaline phosphatase, and the like. The activity of each of these enzymes are readily assayed, or the proteins are recognized by available antibodies.

Merely by way of example, a construct containing the 18 kD isoform of FGF-2 is described. Plasmid 18dx encodes the 18 kD isoform of FGF-2, which is derived from the wild-type human FGF-2 cDNA as previously described (Florkiewicz and Sommer, *Proc. Natl. Acad. Sci. USA* 86:3978, 1989). The FGF-2 sequence is truncated 11 bp 5' of the ATG codon for the 18 kD isoform. Thus, only the 18 kD form is expressed. A fragment containing the cDNA is inserted into pJC119, an SV40-based expression vector, which uses the SV40 late promoter to control expression of the inserted gene. (Sprague et al., *J. Virol.* 45:773, 1983.) It will be apparent that other expression vectors may be used interchangeably and that the choice of the vector will depend in part upon the host cell to be transfected. In this example, FGF-2 cDNA was expressed in COS cells using an SV40-based expression vector. COS cells are chosen because they normally express low levels of FGF-2 and, as such, possess the appropriate cellular machinery for export of this leaderless protein.

Briefly, a leaderless protein may also be fused to a tag sequence to aid in detection of export or identification of proteins that interact with the leaderless protein. The FLAG peptide is fused to HIV tat, FGF-1 and FGF-2, for example. This peptide does not interfere with export of FGF-2. GST is also fused to a leaderless protein, for example, FGF-2 and IL-1.

Other leaderless proteins described above may be used in these constructs. DNA molecules encoding these proteins may be obtained by conventional methods, such as library screening, PCR amplification, and cloning, or obtained from the ATCC/NIH repository of human and mouse DNA probes. Nucleotide sequences of these proteins are generally available from GenBank, EMBL databases, or publications.

It will be recognized that other cell types, vectors, promoters, and other elements used for expression may be readily substituted according to well-known principles. At minimum, a vector construct containing the leaderless protein must have a promoter sequence that is active in the target cell. Optionally, and preferably, the construct contains an enhancer, a transcription terminator, poly(A) signal sequence, bacterial or mammalian origins of replication, and a selectable marker. Such vectors are chosen to be suitable for the species or tissue type of the transfected cell. The cell may be mammalian, avian, or other eukaryotic cell, including yeast, or prokaryote in origin.

Mammalian cells suitable for carrying out the present invention include, amongst others, COS (ATCC No. CRL 1650), BHK (ATCC No. CRL 6281), CHO (ATCC No. CCL 61), HeLa (ATCC No. CCL2), 293 (ATCC No. 1573), NS-1 (ATCC No. T1B18), and Hep G2 (ATCC No. HB 8065).

A wide variety of promoters may be used within the context of the present invention. The choice of promoter will depend, at least in part, on the recipient cell line for transfection. By way of examples, promoters such as the SV40 promoter described above, MoMuLV LTR, RSV LTR, adenoviral promoter, and cytomegalovirus (CMV) immediate early promoter or late promoter may be used. Inducible promoters, such as the TET on/off system (Clontech Life Technologies, Palo Alto, Calif.) and metallothionein gene promoter, may be used. A tissue specific or cell-type promoter may also be used, as long as it is activated in the target cell. For example, the immunoglobulin promoter can be used to express genes in B lymphocytes. Other tissue-specific promoters include those isolated from alpha feto protein, gamma and alpha crystallin, α-actin, carcinoembryonic antigen, prostate-specific antigen, and tyrosinase promoters. Preferred promoters express the leaderless protein at high levels., Enhancers, transcription terminators and selectable markers are well known in the art. Enhancer sequences may be included as part of the promoter region used or additionally included. Enhancers from CMV-IE, RSV LTR, SV40, and others may be used. Transcription terminators are sequences that stop RNA polymerase-mediated transcription. The poly (A) signal may be contained within the termination sequence or incorporated separately. A selectable marker includes any gene that confers a phenotype on the host cell that allows transformed cells to be identified arid preferably allows a growth advantage under specified conditions. Suitable selectable markers for bacteria are well known and include resistance genes for ampicillin, kanamycin, and tetracycline. Suitable selectable markers for mammalian cells include hygromycin, neomycin, genes that complement a deficiency in the host (e.g., thymidine kinase and TK⁻ cells) and others well known in the art.

Once a test cell (or cells) has been constructed or procured, an inhibitor of export may be identified by a cell-based screening assay, or an in vitro binding assay of binding between the transport molecule and leaderless protein. It will be readily apparent that these assays are adaptable for measuring secretion of a leader sequence-containing protein and a cytosolic protein. In general, specific reagents (e.g., antibodies) for these other proteins are substituted for reagents to leaderless proteins.

Assays to detect leaderless protein, secreted protein, and cytosolic protein in a cell-based assay include immunoprecipitation of proteins labeled in a pulse-chase procedure, ELISA, 2-D gels, protein stains (e.g., Coomassie blue), HPLC, Western Blot, biological assays, and phagokinetic tracts. In all these assays, test cells expressing and exporting a leaderless protein are incubated with and without the candidate inhibitor.

Immunoprecipitation is an assay that may be used to determine inhibition. Briefly, cells expressing a leaderless protein from an introduced vector construct are labeled with $^{35}$S-methionine and/or $^{35}$S-cysteine for a brief period of time, typically 15 minutes or longer, in methionine- and/or cysteine-free cell culture medium. Following pulse-labeling, cells are washed with medium supplemented with excess unlabeled methionine and cysteine plus heparin if the leaderless protein is heparin-binding. Cells are then cultured in the same chase medium for various periods of time. Candidate inhibitors are added to cultures at various concentration. Culture supernatant is collected and clarified. Supernatants are incubated with anti-FGF-2 immune serum or a monoclonal antibody, or with anti-tag antibody if a peptide tag is present, followed by a developing reagent such as *Staphylococcus aureus* Cowan strain I, protein A-Sepharose®, or Gamma-bind™ G-Sepharose®. Immune complexes are pelleted by centrifugation, washed in a buffer containing 1% NP-40 and 0.5% deoxycholate, EGTA, PMSF, aprotinin, leupeptin, and pepstatin. Precipitates are then washed in a buffer containing sodium phosphate pH 7.2, deoxycholate, NP-40, and SDS. Immune complexes are eluted into an SDS gel sample buffer and separated by SDS-PAGE. The gel is processed for fluorography, dried, and exposed to x-ray film.

Alternatively, ELISA may be used to detect and quantify the amount of FGF-2 or other leaderless protein, secreted, and cytosolic protein, in cell supernatants. ELISA is preferred for detection in high throughput screening. Briefly, when FGF-2 is the test leaderless protein, 96-well plates are coated with an anti-FGF-2 antibody or anti-tag antibody, washed, and blocked with 2% BSA. Cell supernatant is then added to the wells. Following incubation and washing, a second antibody (e.g., to FGF-2) is added. The second antibody may be coupled to a label or detecting reagent, such as an enzyme or to biotin. Following further incubation, a developing reagent is added and the amount of FGF-2 determined using an ELISA plate reader. The developing reagent is a substrate for the enzyme coupled to the second antibody (typically an anti-isotype antibody) or for the enzyme coupled to streptavidin. Suitable enzymes are well known in the art and include horseradish peroxidase, which acts upon a substrate (e.g., ABTS) resulting in a colorimetric reaction. It will be recognized that rather than using a second antibody coupled to an enzyme, the anti-FGF-2 antibody may be directly coupled to the horseradish peroxidase, or other equivalent detection reagent. If necessary, cell supernatants may be concentrated to raise the detection level.

ELISA may also be readily adapted for screening multiple candidate inhibitors with high throughput. Briefly, such an assay is conveniently cell based and performed in 96-well plates. If test cells naturally or stably express the leaderless protein, the cells are plated at 20,000 cells/well. If the cells do not naturally express the protein, transient expression is achieved, such as by electroporation or CaPO$_4$-mediated transfection. For electroporation, 100 µl of a mixture of cells (150,000 cells/ml) and vector DNA (5 µg/ml) is dispensed into individual wells of a 96-well plate. The cells are electroporated using an apparatus with a 96-well electrode (e.g., ECM 600 Electroporation System, BTX, Genetronics, Inc.). Optimal conditions for electroporation are experimentally determined for the particular host cell type. Voltage, resistance, and pulse length are the typical parameters varied. Guidelines for optimizing electroporation may be obtained from manufacturers or found in protocol manuals, such as *Current Protocols in Molecular Biology* (Ausubel et al. (ed.), Wiley Interscience, 1987). Cells are diluted with an equal volume of medium and incubated for 48 hours. Electroporation may be performed on various cell types, including mammalian cells, yeast cells, bacteria, and the like. Following incubation, medium with or without inhibitor is added and cells are further incubated for 1–2 days. At this time, culture medium is harvested and the protein is assayed by any of the assays herein. Preferably, ELISA is used to detect the protein. An initial concentration of 50 µM is tested. If this amount gives a statistically significant reduction of export, the candidate inhibitor is further tested in a dose response.

Alternatively, concentrated supernatant may be electrophoresed on an, SDS-PAGE gel and transferred to a solid support, such as nylon or nitrocellulose. The leaderless protein is then detected by an immunoblot (see Harlow, *Antibodies: A Laboratory Manual,* Cold Spring Harbor Laboratory, 1988), using an antibody to the leaderless protein containing an isotopic or non-isotopic reporter group. These reporter groups include, but are not limited to enzymes, cofactors, dyes, radioisotopes, luminescent molecules, fluorescent molecules and biotin. Preferably, the reporter group is $^{125}$I or horseradish peroxidase, which may be detected by incubation with 2,2'-azino-di-3-ethylbenzthiazoline sulfonic acid. These detection assays described above are readily adapted for use if the leaderless protein contains a peptide tag. In such case, the antibody used will bind to the peptide tag. Other assays include size or charge-based chromatography, including HPLC, and affinity chromatography.

Alternatively, a bioassay may be used to quantify the amount of leaderless protein exported into cell medium. For example, the bioactivity of the 18 kD FGF-2 may be measured by a proliferation assay, such as the incorporation of tritiated thymidine. Briefly, cells transfected with an expression vector containing FGF-2 are cultured for approximately hours, during which time a candidate inhibitor is added. Following incubation, cells are transferred to a low serum medium for a further 16 hours of incubation. The medium is removed and clarified by centrifugation. A lysis buffer containing protease inhibitors is added. FGF-2 is enriched by binding to heparin-Sepharose® CL-6B and eluted with 1.5 M NaCl. Bioactivity of the FGF-2 is then measured by adding various amounts of the eluate to cultured quiescent 3T3 cells or endothelial cells. Tritiated thymidine is added to the medium and TCA precipitable counts are measured approximately 24 hours later. Reduction of the vital dye MTT is an alternative way to measure proliferation. For a standard, purified recombinant human FGF-2 may be used. Other angiogenic leaderless proteins (e.g., FGF-1, PD-ECGF) may be assessed in similar manner. Leaderless proteins displaying other functions may be assayed in other appropriate bioassays available in the art.

Other in vitro angiogenic assays include measuring proliferation of endothelial cells within collagen gel (Goto et al., *Lab Invest.* 69:508, 1993), co-culture of brain capillary endothelial cells on collagen gels separated by a chamber from cells exporting the leaderless protein (Okamure et al., *B.B.R.C.* 186:1471, 1992; Abe et al., *J. Clin. Invest.* 92:54, 1993), or a cell migration assay (see, Warren et al., *J. Clin. Invest.* 95:1789, 1995).

Alternatively, or as a further assessment of candidate inhibitors, inhibition assays may be performed by assaying the extent of binding between a leaderless protein and its transport protein or proteins. A host cell expressing both the leaderless protein and transport protein endogenously or following transfection are treated with candidate inhibitors. The binding may be measured by a variety of different methods. A co-precipitation assay in which antibodies to either protein are used to precipitate. The precipitates are assayed by gel electrophoresis for disruption of the interaction. The leaderless protein may be a fusion protein with a tag peptide and anti-tag peptide antibodies are used for precipitation. As described above, the membrane bound α1 subunit or fragment may be used in this assay.

An assay for identifying an inhibitor of export may be performed using isolated transport molecule(s) and the leaderless protein. Isolated components are preferably obtained by recombinant expression and purified by standard methodologies. In such an assay, the isolated components are mixed, along with any necessary cofactors, in the presence or absence of the candidate inhibitor. The extent of binding of the leaderless protein and transport molecule is measured. This assay may conveniently be performed in an ELISA or ELISA-style format. Briefly, the transport molecule is adhered to the wells of a 96-well plate. The leaderless protein with or without candidate inhibitors is added to the wells and incubated. Unbound protein is washed away, and the leaderless protein is detected by labeled antibody as described herein, for example. Variations on this assay may be used. For example, the components may be attached to Biocore chips or similar solid phase detection device.

Inhibitor activity may be measured by in vivo models of disease. A cell that exports the leaderless protein of interest to the extracellular environment is introduced into a local milieu where the activity of the protein can be measured. In the case of a cell that exports FGF-1, FGF-2, PD-ECGF, IL-1, thioredoxin, MDGI, Factor XIII, the cell will promote vascularization or angiogenesis, inflammation, clotting, or gliosis on neighboring cells. For example, in the case of a cell exporting FGF-1 that is inoculated along with tumor cells, vascularization of the tumor will ensue. Accordingly, an inhibitor of FGF-1 export will inhibit growth of the tumor. One skilled in the art will recognize that the export levels of the protein may be varied through the use of promoters of varying strength. As well, cells exporting the protein may be transformed stably or express the protein transiently. The site and route of administration depends in part upon the protein and its normal site of action.

When the transport molecule is $Na^+/K^+$ ATPase a rubidium uptake assay may be performed to confirm that the inhibitor does not affect ion transport. Briefly, cells transfected with a vector expressing $Na^+/K^+$ ATPase are grown in the absence or presence of the inhibitor. Radioactive rubidium is added for a further short incubation. Cells are washed, extracted with base, neutralized and counted. An inhibitor that allows rubidium uptake that is not reduced by a statistically significant level compared to the control is useful within the context of this invention.

For leaderless proteins that cause cell motility, such as FGF-2, a phagokinetic tract assay may be used to determine the amount of leaderless protein exported (Mignatti et al., *J. Cellular Physiol.* 151:81–93, 1992). In this assay, cells are allowed to migrate on a microscope cover slip coated with colloidal gold. Under dark field illumination, the gold particles appear as a homogenous layer of highly refringent particles on a dark background. When a cell migrates on the substrate, it pushes aside the gold particles producing a dark track. An image analyzer may be used to measure the length of the tracks. Under conditions cell motility directly correlates with the amount of FGF-2 produced by the cells. The choice of the bioassay will depend, at least in part, by the leaderless protein tested.

In vivo assays may be used to confirm that an inhibitor affects export of leaderless protein. For measuring angiogenic activity, standard assays include the chicken chorioallantoic membrane assay (Aurbach et al., *Dev. Biol.* 41:391, 1974; Taylor and Folkman, *Nature* 247:307, 1982) and inhibition of angiogenesis in tumors. For some leaderless proteins, an assay measuring inhibition of tumor growth, such as in a murine xenogeneic tumor model, may be be appropriate.

Inflammation-inducing leaderless proteins (e.g., IL-1, Dinarello, *J. Am. Soc. Hematology* 87:2095, 1996) may be measured by in vitro or in vivo assays. Briefly, an in vitro assay is performed by adding culture supernatant from cells exporting the protein to a murine T cell line, such as DIO or G4.1, and assaying cytokine, production or proliferation (Ichinose et al., *Cancer Immunol. Immunother.* 27:7, 1988). Supernatant may be added to IL-1 sensitive radiolabeled tumor cells and the release of radioactivity is determined. Alternatively, LPS can be used to induce IL-1β synthesis and release. In vivo inflammation assays include subcutaneous implants of a chamber containing cells exporting IL-1 and assessing infiltration of macrophages and fibroblasts (Hurtenbach et al., *J. Exp. Pathol.* 76:111, 1995; Giller et al., *J. Immunol.* 1:1331, 1995); Xing et al., *Am. J. Respir. Cell Mol. Biol.* 10:148, 1994; Dawson et al., *Agents Actions* 38:247, 1993). Still other assays include hepatic and pulmonary animal models of granulomatosis inflammation due to injections of agents causing chronic inflammation (Allen et al., *J. Clin. Invest.* 76:1042, 1985; Matheny et al., *Growth Factors* 4: 17, 1990, Chensue et al., *J. Immunol.* 1:148, 1992).

In any of these assays, a compound inhibits export if there is a statistically significant reduction in the amount of protein detected extracellularly in the assay performed with the inhibitor compared to the assay performed without the inhibitor. Preferably, the inhibitor reduces export of the leaderless protein by at least 50%, even more preferably 80% or greater, and also preferably, in a dose-dependent manner. In addition, there should be no statistically significant effect on the appearance of either the secreted protein or the cytosolic protein. Preferably, there is less than a 10% increase or decrease in the appearance of these two proteins.

As shown in the Examples and in FIGS. 29A–29C, a library of small molecules is screened for inhibition of FGF-2 export. A number of compounds that inhibited are retested at two different concentrations and also for inhibition of hCG secretion. Ten different compounds inhibit FGF-2, but do not markedly affect hCG secretion.

Administration

As described above, an inhibitor of the export of a leaderless protein is useful for treating tumors, inhibiting angiogenesis, inhibiting inflammation, inhibiting proliferation of cells, including smooth muscle cells that cause restenosis, and treating complications of diabetes, among other uses. In addition, inhibitors may limit viral, bacterial, or fungal infections. Treatment means that symptoms may be lessened or the progression of the disease or conditions halted or delayed. Cells to be treated are contacted with an inhibitor at a therapeutically effective dosage. Contacting may be effected by incubation of cells ex vivo or in vivo, such as by topical treatment, delivery by specific carrier, or by vascular supply.

The conjugates herein may be formulated into pharmaceutical compositions suitable for topical, local, intravenous and systemic application. Time release formulations are also desirable. Effective concentrations of one or more of the conjugates are mixed with a suitable pharmaceutical carrier or vehicle. The concentrations or amounts of the conjugates that are effective requires delivery of an amount, upon administration, that ameliorates the symptoms or treats the disease. Typically, the compositions are formulated for single dosage administration. Therapeutically effective concentrations and amounts may be determined empirically by testing the conjugates in known in vitro and in vivo systems, such as those described herein; dosages for humans or other animals may then be extrapolated therefrom.

Candidate tumors for treatment as described herein include those with receptors for FGF. Such tumors include, but are not limited to, melanomas, teratocarcinomas, ovarian carcinomas, bladder tumors, and neuroblastomas.

Other diseases, disorders, and syndromes are suitable for treatment. Diabetic complications, such as diabetic retinopathy, restenosis, polycystic kidney disease, and atherosclerosis are also candidates for such treatments. Cells in the eye, kidney and peripheral nerve, which are affected in diabetes, may be treated with the conjugates described herein. Viral, fungal, and bacterial infections may be treated.

Pharmaceutical carriers or vehicles suitable for administration of the conjugates provided herein include any such carriers known to those skilled in the art to be suitable for the particular mode of administration. In addition, the inhibitor may be formulated as the sole pharmaceutically active ingredient in the composition or may be combined with other active ingredients.

The compositions of the present invention may be prepared for administration by a variety of different routes. Local administration is preferred. The inhibitor may be mixed with suitable excipients, such as salts, buffers, stabilizers, and the like. If applied topically, such as to the skin and mucous membranes, the inhibitor may be in the form of gels, creams, and lotions. Such solutions, particularly those intended for ophthalmic use, may be formulated as 0.01%–10% isotonic solutions, pH about 5–7, with appropriate salts (see, e.g., U.S. Pat. No. 5,116,868).

Solutions or suspensions used for parenteral, intradermal, subcutaneous, or topical application can include any of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of toxicity such as sodium chloride or dextrose. Parenteral preparations can be enclosed in ampules, disposable syringes or multiple dose vials made of glass, plastic or other suitable material.

If administered intravenously, suitable carriers include physiological saline or phosphate buffered saline (PBS), and solutions containing thickening and solubilizing agents, such as glucose, polyethylene glycol, and polypropylene glycol and mixtures thereof. Liposomal suspensions may also be suitable as pharmaceutically acceptable carriers. These may be prepared according to methods known to those skilled in the art.

The inhibitor may be prepared with carriers that protect it against rapid elimination from the body, such as time release formulations or coatings. Such carriers include controlled release formulations, such as, but not limited to, implants and microencapsulated delivery systems, and biodegradable, biocompatible polymers, such as ethylene vinyl acetate, polyanhydrides, polyglycolic acid, polyorthoesters, polylactic acid and others. For example, the composition may be applied during surgery using a sponge, such as a commercially available surgical sponge (see, e.g., U.S. Pat. Nos. 3,956,044 and 4,045,238).

The inhibitors can be administered by any appropriate route, for example, orally, parenterally, intravenously, intradermally, subcutaneously, or topically, in liquid, semi-liquid or solid form and are formulated in a manner suitable for each route of administration. Preferred modes of administration depend upon the indication treated. Dermatological and ophthalmologic indications will typically be treated locally; whereas, tumors, restenosis, and infections will typically be treated by systemic, intradermal or intramuscular modes of administration.

The inhibitor is included in the pharmaceutically acceptable carrier in an amount sufficient to exert a therapeutically useful effect in the absence of undesirable side effects. It is understood that number and degree of side effects depends upon the condition for which the conjugates are administered. For example, certain toxic and undesirable side effects are tolerated when treating life-threatening illnesses, such as tumors, that would not be tolerated when treating disorders of lesser consequence. The concentration of conjugate in the composition will depend on absorption, inactivation and excretion rates thereof, the dosage schedule, and amount administered as well as other factors known to those of skill in the art.

The inhibitor may be administered one time, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

The following examples are offered by way of illustration and not by way of limitation.

EXAMPLES

Example 1

CONSTRUCTION OF PLASMIDS EXPRESSING FGF-2

The expression vector containing the 18 kD isoform of FGF-2 is constructed as follows. The sequence of the 18 kD isoform of human FGF-2 is provided by plasmid 18dx (Florkiewicz and Sommer, *Proc. Natl. Acad. Sci. USA* 86:3978–3981, 1989). This vector only expresses the 18 kD isoform because the sequences upstream of the ApaI site located 11 bp 5' of the ATG codon initiating translation of the 18 kD FGF-2 isoform are deleted. Briefly, plasmid p18dx is linearized with ApaI and an oligonucleotide adapter containing an XhoI site is ligated to the plasmid. The XhoI restriction fragment containing FGF-2 is purified and subcloned into the XhoI site of pJC119 (Sprague et al., supra).

An expression vector encoding hCG-alpha (Guan et al., *J. Biol. Chem.* 263:5306–5313, 1988) is used as a control for proteins trafficked through the ER/Golgi.

Example 2

CELL CULTURE, TRANSFECTION, AND METABOLIC LABELING

COS-1 cells obtained from the American Type Culture Collection (ATCC CRL 1650) are cultured overnight in 48 well plate in DMEM supplemented with 10% fetal bovine serum, 2 mM L-glutamine, 1 mM sodium pyruvate, 100 nM nonessential amino acids, and 50 μg/ml gentamycin. COS-1 cells are then transfected with 2 μg/ml of CsCl-purified plasmid DNA in transfection buffer (140 mM NaCl, 3 mM KCl, 1 mM CaCl$_2$, 0.5 mM MgCl$_2$, 0.9 mM Na$_2$HPO$_4$, 25 mM Tris, pH 7.4. To each well, 300 μl of the DNA in transfection buffer is added. Cells are incubated for minutes at 37° C., and the buffer is aspirated. Warm medium supplemented with 100 μm chloroquine is added for 1.5 hr. This medium is removed and the cells are washed twice with complete medium. Cells are then incubated for 40–48 hr. The plasmid 18dx is co-transfected with pMAMneo (Clontech, Palo Alto, Calif.), which contains the selectable marker neomycin phosphotransferase. When 2 μg of p18dx are co-transfected with 10 μg of pMAMneo, greater than 70% of transfected cells express both FGF-2 and neo, as determined by immunofluorescence microscopy.

When supernatant is to be immunoprecipitated, at 40 to 48 hours post-DNA transfection, COS-1 cells are metabolically pulse-labeled for 15 minutes with 100 μCi of $^{35}$S-methionine and $^{35}$S-cysteine (Trans $^{35}$S-label, ICN Biomedicals, Irvine, Calif.) in 1 ml of methionine and cysteine free DMEM. Following labeling, the cell monolayers are washed once with DMEM supplemented with excess (10 mM) unlabeled methionine and cysteine for 1–2 minutes. Cells are then cultured in 2 ml of this medium for the indicated lengths of time. For the indicated cultures, chase medium is supplemented with inhibitor at the indicated concentrations.

When supernatant is to be assayed by ELISA, at 40 to 48 hours post-transfection, medium is aspirated from the cells. Cells are washed once with 250 μl of 0.1 M Na carbonate, pH. 11.4, for 1 to 2 minutes and immediately aspirated. A high salt solution is alternative used. The carbonate buffer is removed and cells are washed with media containing 0.5% FBS plus 25 μg/ml heparin. Medium containing 0.5% FBS and 25 μg/ml heparin is added. Cells are then incubated for the indicated lengths of time. For indicated cultures, chase medium is supplemented with an inhibitor. For cells transfected with vector encoding HCG-α or other non-heparin binding protein, the carbonate wash and heparin may be omitted.

Example 3

INDUCTION OF IL-1α EXPORT

Either P388D1 or HTB9 (human bladder carcinoma) cells are seeded at 1×10$^6$ cells/48-well in 0.5 ml RPMI 1640 containing 50 μg/ml gentamycin, glutamine and 15% FBS and incubated overnight at 37° C. in a humidified CO$_2$ chamber.

Cells are induced to export IL-1α by the addition of 1 μM ionomycin or other calcium ionophores, PMA, or 10 μg/ml LPS, and the like. Medium is removed. Cells are washed with the same medium containing 0.5% FBS, with or without test inhibitors, and incubated at 37° C. in a humidified CO$_2$ chamber for the indicated length of time. At the end of the incubation period, cell medium is harvested, centrifuged, and diluted 1 :1 with (20 mL citrate, pH 6.0 containing 2% protease-free HSA, 2 mM EGTA, 0.5 μg/ml each leupeptin, pepstatin, aprotinin, 0.2 mM PMSF and 50 μM AEBSF. Medium is then either assayed immediately for IL-1α or frozen at −20° C.

Example 4

BREFELDIN-RESISTANT EXPORT OF FGF-2

Brefeldin A inhibits secretion of proteins from the ER and Golgi. In contrast, export of a leaderless protein is not inhibited by treatment with brefeldin A.

COS-1 cells are obtained from the American Type Culture Collection and cultured in Dulbecco's Modified Eagle Medium (DMEM, University of California San Diego Core Facility) supplemented with 10% fetal bovine serum (Gemini Bioproducts, Inc.), 2 mM L-glutamine, 1 mM sodium pyruvate, 0.1 mM non-essential amino acids, 100 units/ml penicillin, and 100 units/ml streptomycin. The plasmid SV-40-based expression vector containing the wild type (human) cDNA encoding multiple FGF-2 isoforms (24, 23, 22 and 18-kD) has been described previously (Florkiewicz and Sommer, supra). Approximately 3×10$^5$ COS-1 cells in a 60 mm tissue culture dish awe transfected with 10 μg of CsCl-purified plasmid DNA mixed with 1.0 ml of transfection buffer (140 mM NaCl, 3 mM KCl, 1 mM CaCl$_2$, 0.5 mM MgCl$_2$, 0.9 mM Na$_2$HPO$_4$, 25 mM Tris pH 7.4; all from Sigma Chemical Company). Under these co-transfection conditions using 2 μg of p18dx plus 10 μg pMAMneo, greater than 70% of transfected cells express both proteins, as determined by immunofluorescence microscopy. The ratio of plasmid DNA may be varied with insignificant change in results. Forty to 48 hours post-DNA transfection COS-1 cells are metabolically pulse-labeled for 15 minutes with 100 μCi of $^{35}$S-methionine and $^{35}$S-cysteine (Trans$^{35}$S-label, ICN Biomedicals, Inc.) in 1.0 ml of methionine-and cysteine-free DMEM. After pulse-labeling, the cell monolayers are washed once with DMEM supplemented with excess (10 mM) unlabeled methionine (Sigma Chemical Company) and cysteine (Sigma Chemical Company) and then cultured in 1.0 ml of the same medium (chase) for the indicated lengths of time. Cultures treated with brefeldin A include 15 μg/ml of brefeldin A in the chase medium. Chase medium is also supplemented with 25 μg/ml heparin (Sigma Chemical Company). Although heparin is not necessary to qualitatively detect FGF-2 export, it is necessary in order to quantitatively detect the export of FGF-2 in this assay.

Cell and medium fractions are prepared for immunoprecipitation essentially as described previously (Florkiewicz et al., 1991) except that 400 μl of lysis buffer without NaCl (1% NP-40, 0.5% deoxycholate, mM Tris pH 7.5, 5 mM, EDTA, 2 mM EGTA, 0.01 mM phenylmethylsufonyl fluoride, 10 ng/ml aprotinin, 10 ng/ml leupeptin, and 10 ng/ml pepstatin) is added to the medium fraction clarified by microfuge centrifugation for 15 minutes at 4° C. before adding immune serum. Both cell and medium fractions are incubated with a 1:200 dilution of guinea pig anti-FGF-2 immune serum (prepared in our laboratory) at 21° C. for 40 minutes and then GammaBind G Sepharose® (Pharmacia LKB Biotechnology) is added for an additional 30 minutes incubation. G-Sepharose-bound immune complexes are pelleted, washed three times with lysis buffer and four times with ice cold immunoprecipitation wash buffer (0.15 M NaCl, 0.01 M Na-Phosphate pH 7.2, 1% deoxycholate, 1% NP-40, 0.1% sodium dodecyl sulfate). Immune complexes are eluted directly into SDS-gel-sample buffer and separated by 12% SDS-polyacrylamide gel electrophoresis (PAGE). The gel is processed for fluorography, dried and exposed to X-ray film at −70° C. For immunoprecipitations involving neomycin phosphotransferase (NPT), rabbit anti-NPT antibody (5 Prime-3 Prime, Inc., Boulder, Colo.) was used.

As shown in Florkiewicz et al., 1995 (supra), the export of 18 kD FGF-2 is brefeldin A-resistant and is energy dependent. Sample A was chased with medium alone, sample B was chased with medium supplemented with 25 μg/ml brefeldin A and sample C was chased with medium supplemented with 50 mM 2-deoxy-D-glucose and NaN$_3$. FGF-2 is exported to the medium by 2 hours. Brefeldin A had no substantial effect on this export. However, when NaN₃, a metabolic inhibitor, is present, export is substantially reduced. In contrast, hCG-α, is secreted into the medium by 4 hours and is brefeldin sensitive and energy dependent. hCG-α (SEQ ID NOS: 4, 5) contains a hydrophobic leader (signal) sequence and as a consequence is secreted via the ER and Golgi.

Example 5

IMMUNOPRECIPITATION AND WESTERN BLOT ANALYSIS

Cell and conditioned medium fractions are prepared for immunoprecipitation essentially as described previously (Florkiewicz et al., *Growth Factors* 4:265–275, 1991; Florkiewicz et al., *Ann. N.Y Acad. Sci.* 638:109–126) except that 400 μl of lysis buffer (1% NP-40, 0.5% deoxycholate, mM Tris pH 7.5, 5 mM EDTA, 2 mM EGTA, 0.01 mM phenylmethylsufonyl fluoride, 10 ng/ml aprotinin, 10 ng/ml leupeptin, 10 ng/ml peptstatin) is added to the medium fraction after clarification by centrifugation in a microfuge for 15 minutes. Cell or medium fractions are incubated with guinea pig anti-FGF-2 immune serum (1:200) at 21° C. for 40 minutes. GammaBind™ G Sepharose® (Pharmacia LKB Biotechnology, Uppsala, Sweden) was added for an additional 30 minutes incubation. Immune complexes are pelleted by microfuge centrifugation, washed three times with lysis buffer and four times with ice cold Immunoprecipitation wash buffer (0.15 M NaCl, 0,01 M Na-phosphate pH 7.2, 1% deoxycholate, 1% NP-40, 0.1% sodium dodecyl sulfate). Immune complexes are eluted into SDS gel sample buffer 125 mM Tres, pH 6.8, 4% SDS, 10% glycerol, 0.004% bromphenol blue, 2 mM EGTA and separated by 12% SDS-PAGE. The gel is processed for fluorography, dried, and exposed to X-ray film at –70° C. When neomycin phosphotransferase is immunoprecipitated, a rabbit anti-NPT antibody (5Prime-3Prime, Boulder, Colo.) was used.

For Western blot analysis, proteins are transferred from the 12% SDS-PAGE gel to a nitrocellulose membrane (pore size 0.45 μm in cold buffer containing 25 mM 3-[dimethyl (hydroxymethyl)methylamino]-2-hydroxypropane-sulfonic acid, pH 9.5, 20% methanol for 90 minutes at 0.4 amps. Membranes are blocked in 10 mM Tris, pH 7.5, 150 mM NaCl, 5 mM NaN₃, 0.35% polyoxyethylene-sorbitan monolaurate, and 5% nonfat dry milk (Carnation Co., Los Angeles, Calif.) for 1 hr at room temperature. Membranes are incubated with a monoclonal or polyclonal anti-FGF-2 antibody (Transduction Laboratories, Lexington, Ky.) at 0.3 μg/ml in blocking buffer at 4° C. for 16 hr. Following incubation, membranes are washed at room temperature with 10 changes of buffer containing 150 mM NaCl, 500 mM sodium phosphate pH 7.4, 5 mM. NaN₃, and 0.05% polyoxyethylene-sorbitan monolaurate. Membranes are then incubated in blocking buffer containing 1 μg/ml rabbit anti-mouse IgG (H+L, affinipure, Jackson Immuno Research Laboratories, West Grove, Pa.) for 30 minutes at room temperature. Membranes are subsequently washed in 1 L of buffer described above, and incubated for 1 hr in 100 ml of blocking buffer containing 15 μCi ¹²⁵I-protein A (ICN Biochemicals, Costa Mesa, Calif.), and washed with 1 L of buffer. The radiosignal is visualized by autoradiography.

Example 6

FGF-2 BIOASSAY

The bioactivity of FGF-2 may be measured in a thymidine incorporation assay. Cells transfected with FGF-2 as described above are incubated for 30 hr. At this time, the culture medium is replaced with 6 ml of DMEM containing 0.5% FBS (low serum medium) for 16 hr. The medium is removed, clarified by centrifugation in a microfuge for 15 minutes at 4° C. An equal volume of lysis buffer and heparin-Sepharose® CL-6B is added and the mixture incubated with rocking for 2 hr at 4° C. The Sepharose is pelleted and washed three times with lysis buffer followed by three washes with HS-wash buffer (20 mM Tris, pH 7.4, 5 mM EDTA, 2 mM EGTA, plus protease inhibitors, 0.5 M NaCl) and washed three times with HS-wash buffer containing 1 M NaCl. Proteins that remained bound to the Sepharose were eluted into HS wash buffer containing 3 M NaCl.

The stimulation of DNA synthesis was measured in quiescent Swiss 3T3 cells (clone NR-6) as previously described (Witte et al., *J. Cell Physiol.* 137:86–94, 1988; Florkiewicz and Sommer, *Proc. Natl. Acad. Sci. USA* 86:3978–3981, 1989). Briefly, cells were plated at low density and growth arrested by culturing for 72 hr in 1 ml of media containing 0.1% FBS. Various amounts of the 3 M NaCl HS-eluate are added directly to the culture medium and the level of [³H]-thymidine incorporation into TCA precipitable counts was measured 20–24 hr later. As a control, 1 pg to 1 ng of recombinant human FGF-2 was added to the cells in a similar manner.

Example 7

HIGH THROUGHPUT SCREENING ASSAY FOR INHIBITORS

A high throughput screening assay is performed in a 48-well format. In this example, COS cells expressing FGF-2 are screened with export inhibitors.

On the day of transfection, subconfluent to confluent COS cells are removed from a flask by the treatment with 0.25% trypsin for 5 to 10 minutes at 37° C. Detached cells are collected by centrifugation and washed once with PBS. COS cells are resuspended to 150,000 cells/ml in DMEM medium. Plasmid DNA (p18dxFGF) in a DEAE-dextran solution is added to the cells to a final concentration of 5 μg/ml. This amount is determined from optimization experiments usingl standard procedures. A solution containing FGF-2 DNA/DEAE-dextran is added, and the cells are incubated for 30 minutes at 37° C. The cells are then centrifuged and media containing 100 μM chloroquine is added. Chloroquine is subsequently removed, and the cells are plated at 20,000 cells per well in a 48-well tissue culture plate (Corning). The cells are incubated for 48 hours at which time the media is removed and a 100 mM sodium carbonate solution is added for approximately one minute. The sodium carbonate solution is removed, and the cells are washed with media containing 0.5% FGS and 25 μg/ml heparin. Media supplemented with Ouabain or other test compounds are added to the wells at the indicated concentrations and the cells are incubated for 20–24 hours.

Approximately 20 to 24 hours following the addition of ouabain or other test compounds, cell supernatant is assayed for the presence of FGF-2 using a standard ELISA based assay. Briefly, 96-well half area (COSTAR #369096) ELISA plates are coated with an anti-FGF2 monoclonal antibody at a concentration of 3 μg/ml for two hours at 37° C. Culture supernate samples are diluted in an equal volume of buffer containing protease inhibitors and added to the ELISA plate for an overnight incubation at 2–6° C. The wells are then washed, a biotinylated anti-FGF2 polyclonal antibody (R&D Systems) is added followed by Strepavidin-HRP and a chromogenic substrate. The amount of FGF2 is calculated by interpolation from an FGF2 standard curve.

As shown in FIGS. 29A–29C, ten different small molecules inhibits FGF-2 export from 55–74% at an approximately 10–15 μM concentration.

Example 8

DETECTION OF SECRETED OR CYTOSOLIC PROTEIN AFTER TREATMENT WITH INHIBITOR

COS cells are co-transfected as described above with plasmids expressing FGF-2, hCG-α or neomycin phosphotransferase. Metabolic labeling is performed as described above, except that during the chase period, inhibitor is added at 10 nM to 1 mM in log increments. At the end of the chase, cells and cell media are harvested and processed for immune precipitations as described above.

Ouabain and digoxin inhibit the export of FGF-2, but not hCG-α. Ouabain inhibits 50% of export at approximately 0.1 μM and digoxin at approximately 5 μM. Further experiments with ouabain demonstrate that inhibition is time-dependent, does not affect secretion of hCG-a and inhibits export of FGF-2 in a dose-dependent manner.

Ten small molecules that inhibit FGF-2 export are tested for inhibition of hCG secretion. None dramatically inhibit hCG secretion (FIGS. 29A–29C).

Example 9

ASSOCIATION OF FGF-2 WITH $Na^+/K^+$ ATPASE

Co-transfecting COS cells with two plasmid expression vectors, one encoding 18 kDa FGF-2 and the other encoding the rat $Na^+/K^+$ ATPase α1 isoform, distinguishes whether the ATPase is a component of the transport apparatus. The plasmid (pCMV/ouabain) encoding rat $Na^+/K^+$ ATPase α1 may be purchased from PharMingen Inc. (cat # 40002P). Forty eight hours post transfection, cells are metabolically pulse-labeled with $^{35}$S-methionine (Met) plus cysteine (Cys) for 15 minutes, washed with media containing excess (10 mM) unlabeled Cys and Met, then, incubated for various lengths of time. Cell and corresponding media fractions are immunoprecipitated with guinea pig polyclonal anti-FGF-2 immune serum. Immune complexes are eluted directly into Laemmli gel sample buffer and fractionated by 12% PAGE.

Figure 1A:
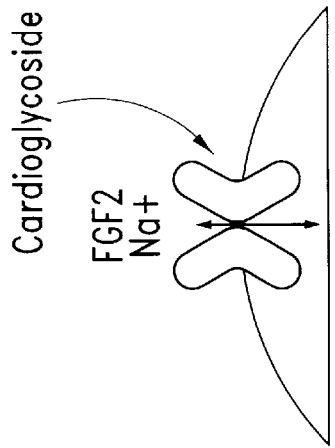
Figure 1B:
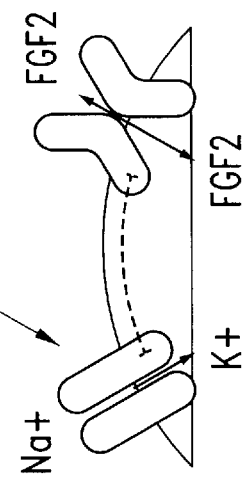
Figure 1C:
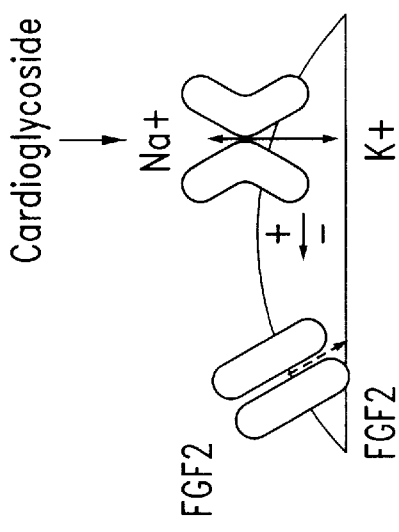
Figure 1D:
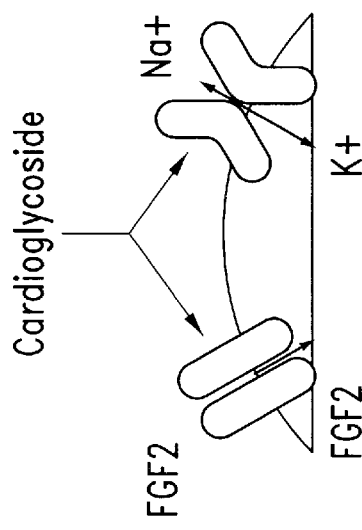
Figure 2A:
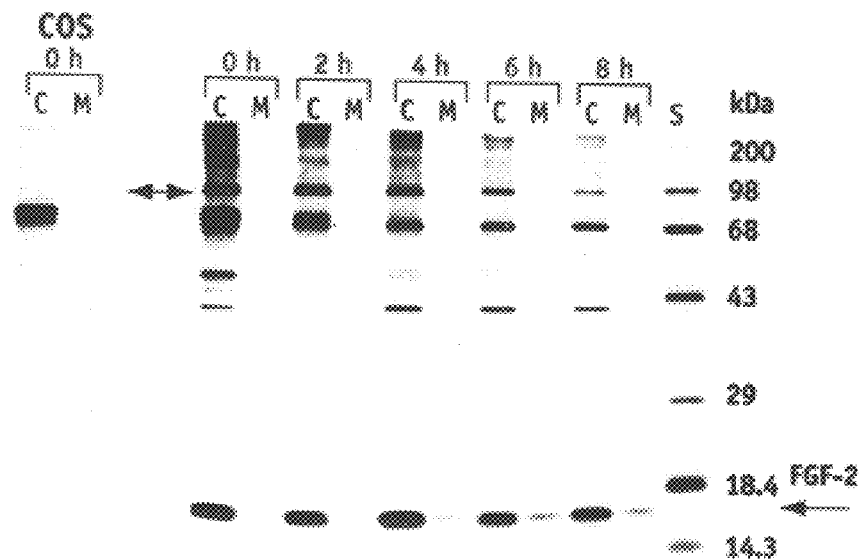
Figure 2B:
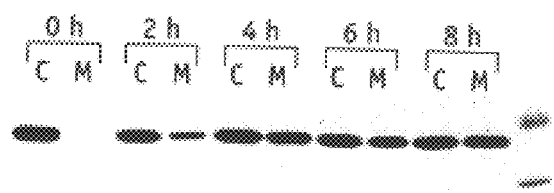

As shown, co-overexpression of rat $Na^+/K^+$ ATPase α1 along with 18 kDa FGF-2 interferes with FGF-2 export (FIG. 2). Compare FGF-2 (arrow) in panel A to panel B. Coexpression of the α1 subunit of rat $Na^+/K^+$ ATPase dramatically slows the rate of FGF-2 export (panel A) compared to control transfected cells (panel B). For reference, the rightmost lane (S) in panel A shows the location of $^{14}$C-labeled protein molecular weight standards, their molecular weights (kDa) are listed.

Figure 3A:
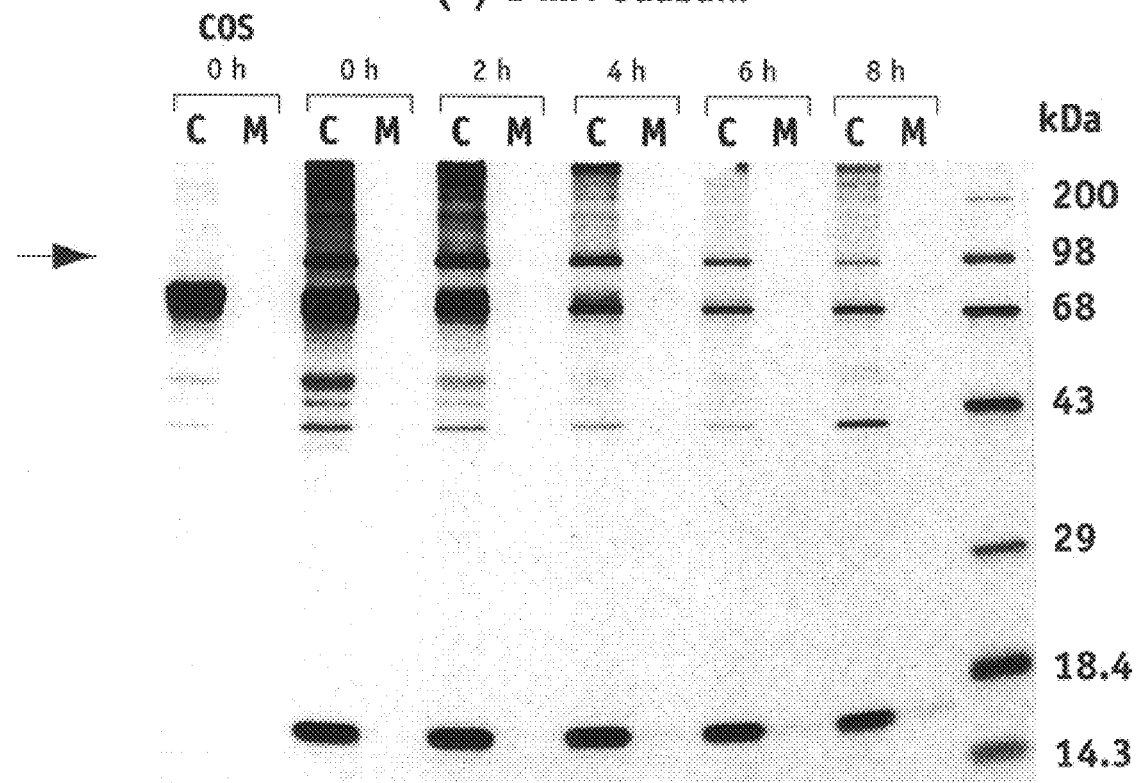
Figure 3B:
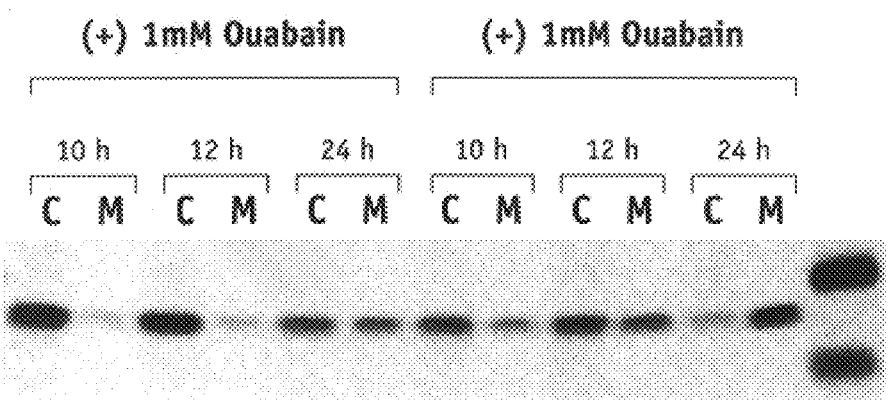

However, export of FGF-2 is not completely inhibited (FIG. 3). It requires greater than 12 hours for metabolically pulse labeled FGF-2 to become equally distributed between cell and media fractions (panel B). By twenty-four hours labeling export is essentially quantitative. Although 1 mM ouabain would completely inhibit export from FGF-2 only transfected COS cells, significant amounts of FGF-2 can be detected in media of $Na^+/K^+$ ATPase α1 co-transfected cells twenty-four hours post labeling. Since the rat $Na^+/K^+$ ATPase α1 isoform is 100 times more resistant to ouabain inhibition, these data further implicate $Na^+/K^+$ ATPase in export. These data also suggest that ouabain is not binding to a previously unidentified cell surface protein that functions as the FGF-2 exporter. If it were, then co-overexpression would have had no effect on FGF-2 export and/or the sensitivity to ouabain would have been the same.

Figure 4:
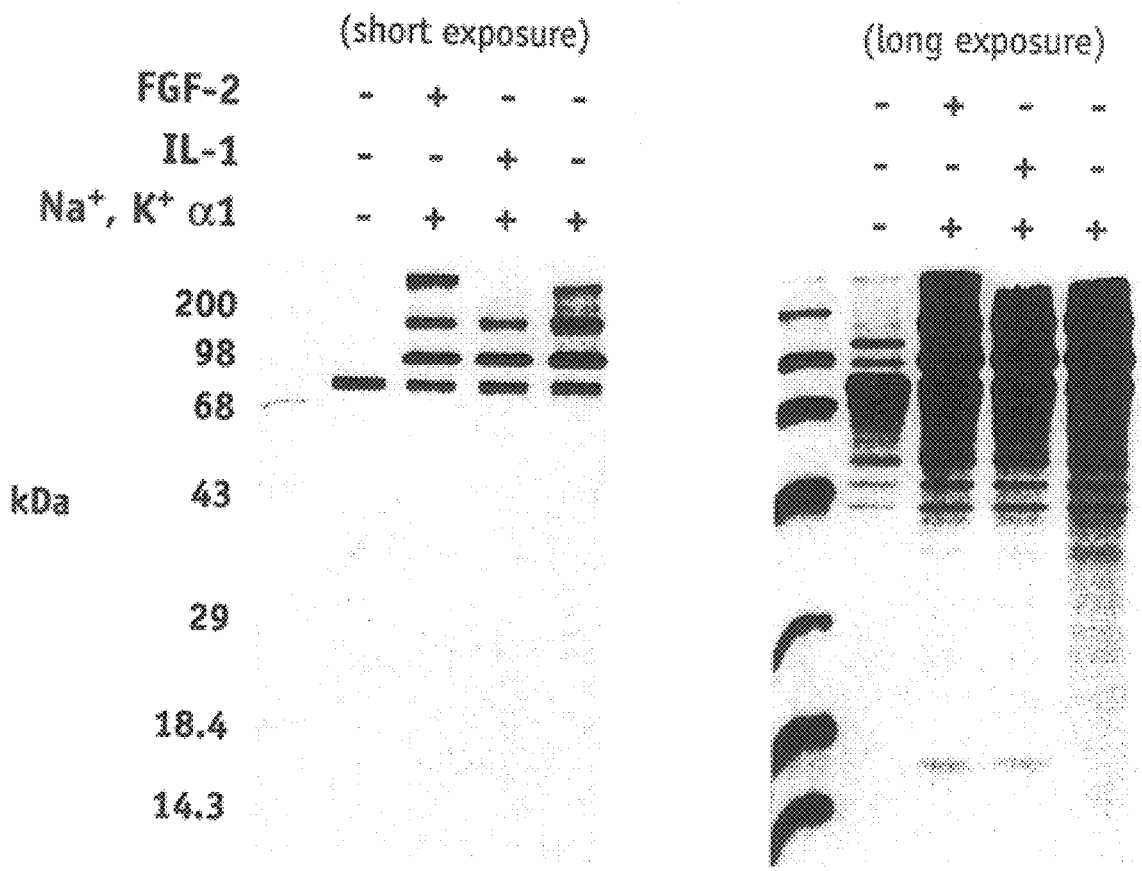
FIG. 4 is an autoradiogram of an immunoprecipitation with anti-Na$^{30}$/K$^{30}$ ATPase α1 antibody following transfection into COS cells. The table at the top indication the transfected genes.

The approximately 110 kDa protein band (FIG. 2, double arrow in panel A) is co-immunoprecipitated with FGF-2 using FGF-2 immune serum. This band is not detected in singly transfected or control non-transfected COS cells and is the correct size to be rat $Na^+/K^+$ ATPase α1. Immunoprecipitation of metabolically labeled COS cell extracts with monoclonal anti-rat $Na^+/K^+$ ATPase α1 antibody, purchased from Upstate Biotechnology Inc. (cat # 05-369), detects the same 110 kDa band plus an additional band, approximately 150 kDa (FIG. 4, panel A). When this gel is exposed to X-ray film for a longer period of time, an 18-kDa FGF-2 band can also be detected (FIG. 4, panel B). IL-1α can also be co-immunoprecipitated with rat $Na^+/K^+$ ATPase α1 from similarly co-transfected COS cells (FIG. 4, panel B). However, the 150 kDa band was not detected when immune complexes were prepared from co-expressing COS cells using anti-FGF immune serum. This suggests that the 150-kDa band is either a modified $Na^+/K^+$ ATPase α1 or represents a protein complex that includes $Na^+/K^+$ ATPase α1. Taken together, co-immunoprecipitation shows that FGF-2 directly interacts with $Na^+/K^+$ ATPase α1. This interaction is specific and not a consequence of our detergent lysis procedure, because complexes are not detected when singly transfected COS cell extracts are mixed, incubated for 4 hours and then immune precipitated.

Figure 5:
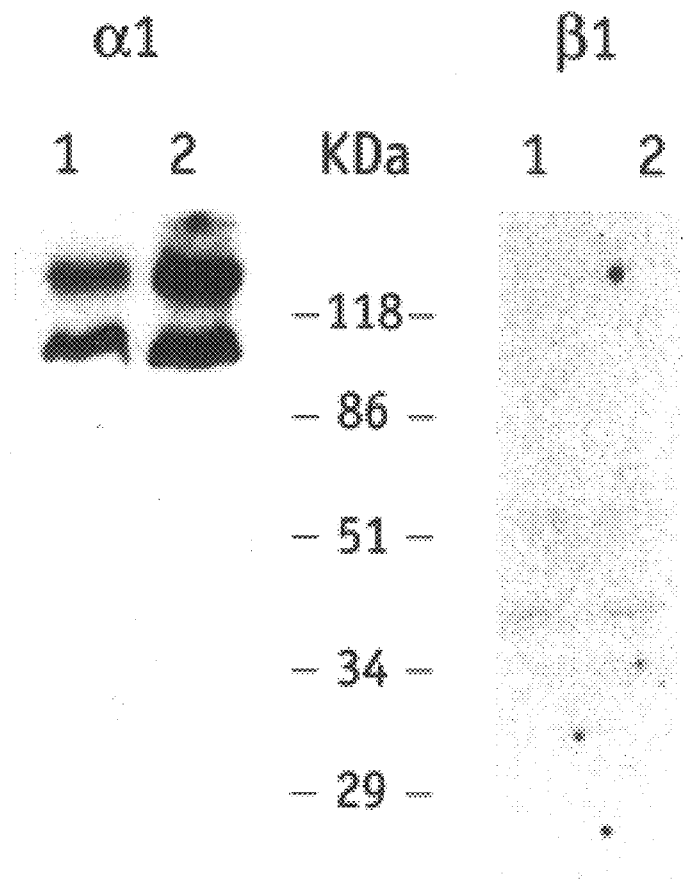
FIG. 5 is a Western blot of total COS cell extracts from nontransfected (lane 1) and pCMV/ouabain transfected (lane 2) cells. The antibody used for the left panel is an anti-Na$^+$/K$^+$ ATPase α1 antibody and for the right panel is an anti-Na$^+$/K$^+$ ATPase β1 antibody.
Figure 6:
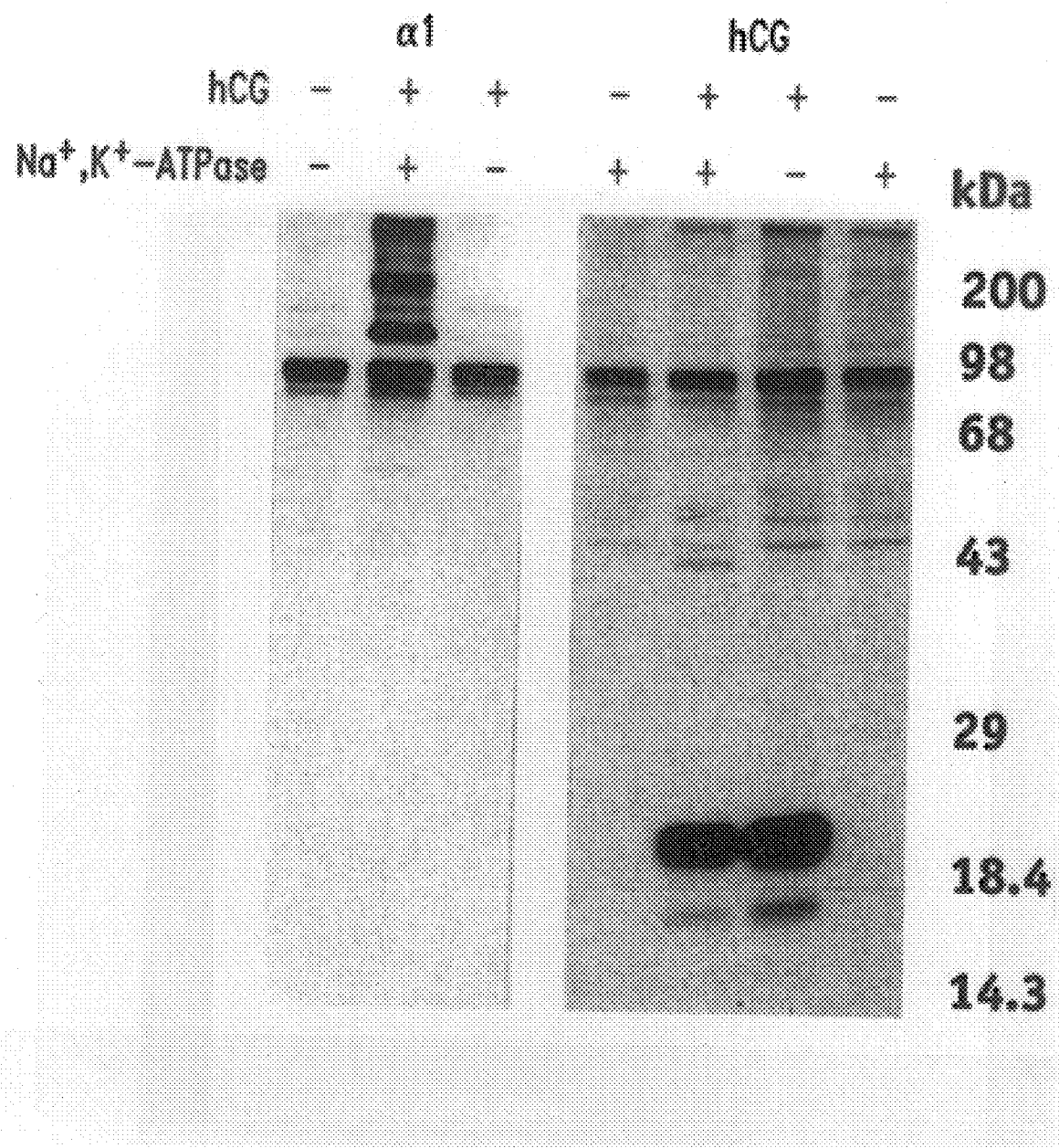
FIG. 6 is an autoradiogram of an immunoprecipitation with either anti-Na$^{30}$/K$^{30}$ ATPase α1 or anti-hCG antibody. The table at the top indicates the transfected genes.

Western blot analysis was used to confirm the identity of the 110 kDa band as rat $Na^+/K^+$ ATPase α1 (FIG. 5). Total cell extracts in 100 μl of standard detergent lysis buffer are prepared from 60 mm plates of non-transfected (lane 1) as well as pCMV ouabain transfected COS cells (lane 2). 60 μl of this extract is mixed with 20 μl of 4× concentrated Laemmli gel sample buffer and heated at 65° C. for 20 minutes. Samples are fractionated by 12% PAGE and transferred to nitrocellulose membrane supports. The probe was the same monoclonal anti-rat $Na^+/K^+$ ATPase α1 antibody used for the immunoprecipitation experiments described above. However, in this case, steady state levels of endogenous gene expression are detected as well as expression from the transfected gene, both non-transfected and pCMV ouabain transfected COS cells contain an approximately 110 kDa immunoreactive band. A significant increase in this band is detected in pCMV ouabain transfected COS cells, i.e., from those cells expressing rat $Na^+/K^+$ ATPase α1.

Co-immunoprecipitation of rat $Na^+/K^+$ ATPase α1 from co-transfected COS cells is specific for FGF-2. Results from a series of control experiments using overexpressing transiently transfected COS cells are shown in FIGS. 6–10. For example, using a plasmid expression vector encoding human chorionic gonadotropin-α (hCGα), ER/Golgi-dependent secretion of hCG is clearly distinguished from FGF-2 export. Moreover, hCG does not co-immunoprecipitate with $Na^+/K^+$ ATPase α1 (FIG. 6) even though $Na^+/K^+$ ATPase α1 subunit and hCG are in close proximity during transport through ER and Golgi apparatus, and they both possess signal sequences.

A number of cytosolic proteins other than FGF-2 have been overexpressed in transiently transfected COS cells and remain cell associated in metabolic labeling pulse chase experiments. These include neomycin phosphotransferase (NPT) and beta galactosidase (β-gal). However, the exported phenotype can be conferred to both proteins when expressed as chimeras with 18 kDa FGF-2. The FGF-2 NPT chimeric protein is termed FPT and the FGF-2 β-gal chimeric protein F-gal. Export of both FPT and F-gal chimeric proteins can be inhibited by ouabain, in a manner paralleling that for FGF-2. Therefore, the FPT chimeric protein was tested in more detail for its ability to be co-immunoprecipitated with $Na^+/K^+$ ATPase α1 from co-transfected COS cells (FIGS. 7–9). The data indicate that FPT interacts with $Na^+/K^+$ ATPase α1 and is co-immunoprecipitated. In contrast, authentic NPT does not co-immunoprecipitate with $Na^+/K^+$ ATPase α1 regardless of which antibody or immune serum was employed. The same results are achieved with the F-gal chimeric protein. In FIGS. 10 and 11, COS cells are co-transfected with plasmids encoding the α subunit of $Na^+/K^+$ ATPase and FGF-2 or with the FGF-2 plus VSVG chimeric protein.

In addition to interaction of α1 subunit with FGF-2, both α2 and α3 isoforms also bind to FGF-2. The isoforms α2 and α3 are co-expressed at a 4:1 ratio with FGF-2 in transfected COS cells as described above. As seen in FIGS. 13–16, α2 and α3 interfere with the export of FGF-2. As well, a protein of approximately 110 kDA is also detected; this is the size expected for the α2 and α3 subunits.

Immune complexes prepared from metabolically labeled co-transfected COS cells using anti-α2 or anti-α3 antibody show a protein band the size of FGF-2 (FIG. 16).

Example 10

OUABAIN SENSITIVITY OF IL-1 EXPORT

A vector containing an IL-1α gene is transfected into COS cells. Cells are metabolically labeled and protein precipitated with anti-IL-1α antibody. As seen in FIGS. 12, 17, 19 and 21, IL-1α is exported into the media fraction (M). This export is inhibited by incubation with 5 mM ouabain (FIGS. 18, 20 and 21). In contrast to the export of FGF-2, the rate of IL-1 export is slower, having a $T_{1/2}$ of greater than 24 hrs. However, like FGF-2, the export is sensitive to ouabain. In addition, IL-1α can be immunoprecipitated from co-transfected COS cells (transfected with IL-1α and α1 subunit of Na/K ATPase) using anti-α1 subunit antibody (FIG. 4).

Example 11

RUBIDIUM UPTAKE ASSAY TO MEASURE ION TRANSPORT ABILITY OF $NA^+/K^+$ ATPASE

The ion transport activity of $Na^+/K^+$ ATPase may be measured in the presence and absence of inhibitor by a rubidium uptake assay.

In this assay, cells that express the $Na^+/K^+$ ATPase are grown in the presence of inhibitor. The mutated rat α2 isoform, referred to as rat α2*, is modified by the substitutions L111R and N122D at the borders of the first intracellular domain.

This makes rat α2* resistant to ouabain ($IC_{50}$ approximately 50 μM). Site-directed mutagenesis is used to make further mutations at position 327.

Wild type COS cells, HeLa cells and HeLa cells transfected with the rat α2* mutants are maintained in DMEM with 10% calf serum, 100 units/ml penicillin, 0.1 mg/ml streptomycin, 250 ng/ml amphotericin B, at 37° C. in a 5% $CO_2$ atmosphere. $^{86}Rb$ is obtained from DuPont-New England Nuclear. The specific radioactivity varies from approximately 2–10 mCi/mg. Ouabain and furosemide are obtained from Calbiochem or Sigma.

Native HeLa or cells transfected with rat α2* are plated at $3 \times 10^4$ cells per ml in 24 well tissue culture plates (1 ml per well). The rat α2* transfected cells are grown in the absence or presence of 1 μM inhibitor to examine ouabain dose response in cells that display both endogenous and transfected ion transport activities or with cells that display the transfected activity alone. Cells are incubated until about 80% confluent, then rinsed with PBS (135 mM NaCl, 3.5 mM KCl, 0.5 mM $CaCl_2$, 0.5 mN $MgCl_2$, 5 mM glucose, 6.5 mM $Na_2HPO_4$, 1.5 mM $KH_2PO_4$,) and further incubated with PBS containing the indicated inhibitor concentrations for 30 min at 37° C. $^{86}Rb$ is their added at approximately 2 μCi per ml for 10 min at 37° C. The concentration of $^{86}Rb$ typically ranges from 2–15 μM. The incubation is stopped by submerging the plate in an ice cold solution of 0.9% NaCl and 5 mM HEPES, pH 7.4. Wells are then rinsed 8 times in this solution. Total rinse time is less than 1 minute. Cells are extracted with 0.5 ml 0.2 N NaOH for 1 hour, then neutralized with HCl before counting. Samples are counted in a Packard Tricarb Liquid Scintillation Analyzer, Model 2000CA, which has an efficiency for $^{86}Rb$ of 97%.

Example 12

CONSTRUCTION OF A GST-FGF2 FUSION PROTEIN AND IDENTIFICATION OF INTERACTING PROTEINS

In this example, a fusion gene of glutathione S-transferase (GST) with FGF-2 is constructed. The fusion protein is then used in affinity column chromatography to identify proteins or protein complexes that interact with FGF-2.

An expression vector encoding the 18 kDa isoform of FGF-2 (pGEXF18) is prepared. The plasmid pGEXF18 is constructed by amplifying a sequence encoding the 18 kDa FGF-2 and inserting the amplified fragment into the NotI site of pGEX-4T-3 (Pharmacia, Uppsala, Sweden). The template for amplification is p18dx (see Example 1), which encodes only the 18 kDa isoform of FGF-2. The forward amplification primer (SEQ ID NO: 20) is 5'-AAGGACAGAAGCGGCCGCGGGACCATGGCAG-3',
and the reverse amplification primer (SEQ ID NO: 21) is

5'-AAGGACAGAAGCGGCCGCTCAGCTCTTAGC AGCCATTGG-3'.

The amplification conditions are 2 cycles of 94° C. for 5 min, 45° C. for 5 min, 72° C. for 1 min; 4 cycles of 94° C. for 1 min, 45° for 1 min, 72° C. for 1 min; 25 cycles of 94° C. for 1 min, 55° C. for 1 min, 72° C. for 1 min; and 1 cycle of 72° C. for 10 min.

Bacteria (for example, DH5α or BL21) containing the GST-FGF-2 expression plasmid are induced with IPTG (0.2 mM) for 3 hours. Extracts are prepared and the GST-FGF-2 fusion protein purified using glutathione-Sepharose as described by the manufacturer. Purified fusion protein is eluted from glutathione beads by 10 mM glutathione.

COS cells (100 mm plates 80% confluent) are metabolically labeled for 4 hours in cysteine/methionine-free DMEM supplemented with 100 μCi/ml of $^{35}$S-trans label (ICN, Irvine, Calif.). After labeling, cell monolayers are washed with buffer containing 25 mM Tris, pH 8.0, 150 mM NaCl. Cells are lysed with 2.0 ml NETN buffer (20 mM Tris pH 8.0, 100 mM NaCl, 1 mM EDTA, 0.5% NP40) as described (Kaelin et al., Cell 64:521–532, 1991). This cell extract is clarified of insoluble material by microcentrifugation at 4° C. for 15 minutes. Other cell types can be substituted for COS cells, as well as other wild type and mutant GST fusion proteins may be used.

Glutathione-Sepharose beads (100 μl) are charged with purified GST-FGF fusion protein (25 μg) in buffer containing NETN plus 0.5% powdered milk while rocking for 30 minutes at 4° C. The metabolically labeled COS cell extract (0.5 ml) is incubated with 25 μl of the charged beads for 1 hour at 4° C. Sepharose beads with bound proteins are then pelleted by centrifugation and washed 4 times with cold NETN buffer. Bound proteins are eluted in SDS-Laemmli gel sample buffer and incubated at 70° C. for minutes. Eluted proteins are fractionated on 12%-PAGE (FIG. 22). Non-specific background is detected in lanes corresponding to metabolically labeled COS cell protein bands binding control GST alone (GST 4T) and a control unrelated GST fusion protein (GST R2). However, at least 4 distinct COS cell proteins appear to bind specifically to GST FGF-2. Protein bands identified could represent direct interactions or interactive protein-complexes. COS cell protein bands detected using GST 18 kDa FGF-2 are approximately 35, 45/50 and 70 kDa. The pattern of protein bands detected in all cases is reproducible. Additional very large proteins or protein complexes are not identified at this time.

Example 13

CONSTRUCTION OF AN FGF1 FUSION PROTEIN

Several fusion proteins are constructed in which FGF 1, either full-length or a fragment, is fused at the N-terminus to GST or at the C-terminus to a peptide tag.

The FGF-1 designer gene clone, BBG21 (R&D Systems, Minneapolis, Minn.), does not encode a full-length wild type protein. It lacks 14 amino acids at the N-terminus of the wild type primary translation product. A full length wild type FGF-1 is prepared from the plasmid BBG21 (R&D Systems). Based on that sequence the forward amplification primer (SEQ ID NO: 22) is 5'-CTAGGGATCCACCATGGCCGAGGGCGAAAT TACAACA-TTCACCGCCCTCACCGAAAAGTTT AATCTGCCTCCCGG-3' and the reverse amplification primer for wild type FGF-1 (SEQ ID NO: 23) is

5'-GATCGAATTCTCAATCAGAAGAAGCTGGCAG-3'.

The forward primer recreates the following N-terminal amino acids: AEGEITTFTALTEK (SEQ ID NO: 24). This primer set is designed for insertion into the BamHI/EcoRI sites of pcDNAIII (Invitrogen, La Jolla, Calif.). This vector allows expression in mammalian cells, including transient over-expression in COS cells. The amplified product is designed to have a preferred sequence context for translation initiation. In addition the same amplified product and restriction sites allow an inframe N-terminal fusion with GST (pGEX-4T-3). Amplification conditions consist of 1 cycle 1 of 94° C. for 1 min; 8 cycles of 94° C. for 45 sec, 48° C. for 45 sec, and 72° C. for 1 min; 25 cycles of 94° C. for 45 sec, 65° C. for 45 sec, and 72° C. for 1 min; and 1 cycle of 72° C. for 5 min.

In order to have additional antibodies to choose from for immunoprecipitation of a full-length and/or N-terminal truncated FGF-1, FGF1 is also fused to C-terminal sequences that encode peptide tags recognized by antibodies that are commercially available. The C-terminal epitope tags include the flg peptide DYKDDDDK (SEQ ID NO: 35) and influenza haemagglutinin (HA) peptide YPYDVPDYA (SEQ ID NO: 36). The reverse amplification primer sequence adding the HA epitope tag to FGF-l (SEQ ID NO: 25) is:

5'-CTAGTCTAGATCAGGCGTAGTCGGGCACG-TCGTATGGGTAATCAGAAGAGACTGGCAGG-3'.

The reverse primer adding the flg epitope tag to FGF-1 (SEQ ID NO: 26) is

5'-GATCGAATTCTCACTTGTCATCGTCGTCCTT-GTAGTCACGCGTATCAGAAGAGACTGGCAG-3'.

In both cases, the forward primer is as described above. Amplification conditions are 1 cycle of 94° C. for 1 min; 8 cycles of 94° C. for 45 sec, 48° C. for 45 sec, 72° C. for 1 min; 25 cycles of 94° C. for 45 sec, 65° C. for 45 sec, and 72° C. for 1 min; and 1 cycle of 72° C. for 5 min.

Example 14

CONSTRUCTION OF HIV TAT FUSION PROTEINS

Both an 85 amino acid and a 72 amino acid tat gene product is constructed as a fusion with C-terminal epitope tag sequences. The template for Tat85 is BBG34 (R&D Systems; Minneapolis, Minn.) and for Tat72 is pSV2tat72. For subcloning HIV Tat 72 or TAT 85, the forward amplification primer (SEQ ID NO: 27) is

5'-CTAGGGATCCACCATGGAACCAGTCGACC-3'

The reverse primer for wild type Tat 85 (SEQ ID NO: 28) is

5'-GATCGAATTCTCATTCCTTAGGACCTGTCGG-3' and the reverse primer encoding the C-terminal HA-tag epitope (SEQ ID NO: 29) is

5'-CTAGTCTAGATCAGGCGTAGTCGGGCACG-TCGTATGGGTATTCCTTAGGACCTGTCGG-3'.

The reverse primer for Tat 72 (SEQ ID NO: 30) is

5'-CTAGGAATTCAGATCACTGTTTAGACAGAG-3' and the reverse primer encoding the C-terminal fig tag (SEQ ID NO: 31) is

5'-CTGAGAATTCTCACTTGTCATCGTCGTC-CTTGTAGTCCTGTTTAGACAGAGAAACC-3'.

The reverse primer for Tat72 plus C-terminal HA-tag (SEQ ID NO: 32) is

5'-CTGAGAATTCTCAGGCGTAGTCGGGCACGT-CGTATGGGTACTGTTTAGACAGAGAAACCTG-3'.

Reaction conditions for amplification of wild type Tat 85 and Tat85HA-tag are: 1 cycle of 94° C. for 1 min; 8 cycles of 94° C. for 45 sec, 52° C. for 45 sec, and 72° C. for 1 min; 25 cycles of 94° C. for 45 sec, 65° C. for 45 sec, and 72° C. for 1 min; and 1 cycle of 72° C. for 5 min. Reaction conditions for amplification of Tat72 using the above primers are: 1 cycle of 94° C. for 1 min; 8 cycles of 94° C. for 45 sec, 52° C. for 45 sec, and 72° C. for 1 min; 25 cycles of 94° C. for 45 sec, 65° C. for 45 sec, and 72° C. for 1 min; and 1 cycle of 72° C. for 5 min Amplification conditions for Tat72 plus flg-tag are: 1 cycle of 94° C. for 1 min; 8 cycles of 94° C. for 45 sec, 50° C. for 45 sec, and 72° C. for 1 min; 28 cycles of 94° C. for 45 sec, 65° C. for 45 sec, and 72° C. for 1 min; and 1 cycle of 72° C. for 5 min. Conditions for amplification of Tat72 HA-tag are: 1 cycle of 94° C. for 1 min; 8 cycles of 94° C. for 45 sec, 55° C. for 45 sec, and 72° C. for 1 min; 28 cycles of 94° C. for 45 sec, 70° C. for 45 sec, and 72° C. for 1 min; and 1 cycle of 72° C. for 5 min.

Example 15

CONSTRUCTION OF IL-1α FUSION PROTEINS

A vector encoding mature human IL-1α is used to transfect COS cells. As described above, a subclone in pGEX4T-3 is prepared to detect cell associated protein(s) that bind with mature IL-1α. The forward PCR primer (SEQ ID NO: 33) is

5'-CTAGGGATCCACCAT-GAGGATCATCAAATACGAATTC-3' and the reverse PCR primer (SEQ ID NO: 34) is

5'-GCACTTCTCGAGCTACGCCTGGTTTTCCAGT ATC3'.

The PCR amplification conditions are: 1 cycle of 94° C. for 1 min; :3 15 cycles of 94° C. for 45 sec, 60° C. for 45 sec, and 72° C. for 1 min; 25 cycles of 94° C. for 45 sec, 70° C. for 45 sec, and 72° C. for 1 min; and 1 cycle of 72° C. for 5 min.

Both IL-α and FGF-2 are exported from transfected COS cells in a ouabain sensitive manner. Therefore, the profile of binding proteins for each leaderless protein that is present in COS cells is compared to determine if there are common and/or distinct binding proteins. In addition, IL-1α will be expressed in the rodent macrophage cell line P388D1. A similar strategy can be used for IL-1β.

Example 16

CONSTRUCTION OF VSV N GENE PRODUCT FUSION PROTEINS

A GST-VSV N gene product fusion is prepared in pGEX4T-3 vector.

The data presented in FIGS. 23–28 show that VSV N protein expressed in transiently transfected COS cells can be detected in conditioned media. The N protein does not contain a hydrophobic signal peptide sequence and is therefore predicted to reside in the cytosol. Polyclonal rabbit anti-VSV antibody is used to precipitate the N protein from metabolically labeled cells. As shown herein, the N protein is detected extracellularly in a time dependent manner (FIG. 23) that is resistant to ouabain (FIGS. 24, 27), ATP-dependent (FIG. 25) and ER/Golgi-independent (FIG. 26).

Example 17

CONSTRUCTION OF FGF-2 MUTAGENS

Dissection of the contact sites of FGF-2 with the α subunit of $Na^+/K^+$ ATPase is pursued by constructing muteins of FGF-2 and assessing the effect of the mutation on export of FGF2.

The initial construct, called pBSSK+FGF-2, is generated by ligating the XhoI fragment containing FGF-2 from p18dx into the XhoI site of pBSSK+. Mutagenesis is accomplished using a kit (Chameleon™ Double-Stranded Site-Directed Mutagenesis Kit; Stratagene Cloning Systems, San Diego, Calif.). Briefly, the mutagenic and selection primers are designed to be (a) 25–45 bases long with 10–15 bases on either side of the mutation, (b) have at least a 40% G+C content, and (c) terminate in 1 or more Gs or Cs. Primers are phosphorylated and annealed at a 100:1 molar ratio with template DNA by boiling for 5 min, quenching on ice, then incubating at room temperature for 30 min. The primers are extended and ligated using T7 DNA polymerase, T4 DNA ligase and single stranded binding protein. The ligase is heat inactivated and the reaction mix is digested with a restriction enzyme that cuts parental plasmid only (the mutant containing plasmid has abolished the restriction site with the selection primer). The mutant plasmids are transformed into XLmutS competent cells. Transformed cells are grown in liquid culture. DNA from the transformants is recovered and digested again with the selection restriction enzyme. The uncut plasmid is used to transform XL1-Blue competent cells. Approximately 70% or greater colonies contain mutagenized plasmids. Individual colonies are picked, and plasmid DNA isolated. Mutants are verified by restriction digestion and DNA sequence analysis.

The following FGF-2 mutants are constructed:

| | | |
|---|---|---|
| Ser5 → Val | Glu108 → Pro, Ala | Ser122 → Trp |
| Tyr33 → Ala, Leu | Tyr112 → Ala | Lys128 → Asp, Pro |
| Arg53 → Trp, Ile | Tyr115 → Ala | Arg129 → Glu, Leu |
| Ser73 → Trp, Val, Thr | Ser117 → Ala | Lys134 → Thr |
| Cys78 → Ser | Arg118 → Ile | Lys144 → Val |
| Cys96 → Ser | Tyr120 → Ala | Met151 → Arg |
| Glu105 → Pro, Lys | Thr121 → Pro | Ser152 → Val, Trp |

A positive clone for each mutant is subcloned back into p18dx via the Xho I site. These clones are expressed in COS cells and assayed by metabolic labeling using Tran$^{35}$S Label (ICN, Irvine Calif.) as described herein. Results for some of these muteins are presented below.

| Mutation | Changes | Effect of Mutation on Export | Effect of Ouabain on Export |
|---|---|---|---|
| Arg53Trp | CGG/TGG | decrease at 7 hr | decrease |
| Ser73Trp | TCT/TGG | decrease | N.D. |
| Tyr112Ala | TAC/GCC | unstable protein | protein unstable at 7 hr |
| Arg118Ile | AGG/ATC | decrease at 7 hr | decrease |
| Thr121Pro | ACC/CCG | unstable protein | |
| Lys134Thr | AAA/ACC | large decrease at 7 hr | |
| Lys144Val | AAA/GTA | decrease | decrease |
| Cys78Ser | | decrease | N.D. |
| Cys96Ser | | decrease | N.D. |
| Cys78Ser + Cys96Ser | | small increase | decrease |

N.D., not done

In addition, the relative amounts of wild-type FGF-2 and some of the muteins that are compartamentalized intracellularly and are exported are presented below. At 7 hours, export of all FGFs is inhibited by ouabain.

| | 7 hr (−) Ouabain | | 7 hr (+) Ouabain | | ratio 7 hr/0 hr |
|---|---|---|---|---|---|
| Mutant | Cells | Media | Cells | Media | Cells |
| 18dx (wt) | 46% | 54% | 82% | 18% | 1.48 |
| Y112/115A | Unstable | | Unstable | | 0 |
| R118I | 47% | 53% | 79% | 21% | 0.45 |
| K144V | 50% | 50% | 70% | 30% | 0.41 |
| 18dx (wt) | 39% | 61% | 50% | 50% | 0.36 |
| R53W | 40% | 60% | 70% | 30% | 0.25 |
| K134T | 53% | 47% | 70% | 30% | 0.26 |
| C78, 96S | 42% | 58% | 62% | 38% | 0.68 |

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. A method for detecting a transport molecule involved in non-ER/Golgi leaderless protein export, comprising:

(a) contacting cell extracts or cell membranes suspected of containing a transport molecule involved in non-ER/Golgi protein export with a fusion protein of a leaderless protein and a tag to form a complex of the fusion protein bound to the transport molecule, said leaderless protein selected from the group consisting of a protein found in the extracellular environment that lacks a canonical leader sequence, interleukin-1α, interleukin-1β, Fibroblast growth factor-1 (FGF-1), Fibroblast growth factor-2 (FGF-2), HIV tat, platelet-derived endothelial cell growth factor (PD-ECGF), ciliary neurotrophic factor (CNTF), sciatic nerve growth-promoting activity, vas deferens protein, transglutaminase, L-14 lectin, factor XIIIa, thioredoxin--like protein (ADF), thymosin, parathymosin, mammary-derived growth inhibitor, galectin, and rhodanase;

(b) isolating the complex; and (c) detecting the transport molecule in the complex.

2. The method of claim 1, wherein said tag is glutathione-S-transferase or a fragment thereof that binds glutathione.

3. The method of claim 1, wherein said detecting step is denaturing gel electrophoresis.

4. The method of claim 1, wherein said fusion protein is bound to a solid support.

5. The method of claim 4, wherein said solid support is a sepharose column.

6. The method of claim 5, wherein said sepharose column is a glutathione-sepharose column.

* * * * *

SEQUENCE LISTING (1) GENERAL INFORMATION:

(iii) NUMBER OF SEQUENCES: 36

(2) INFORMATION FOR SEQ ID NO:1:

(i) SEQUENCE CHARACTERISTICS:
       (A) LENGTH: 1120 base pairs
       (B) TYPE: nucleic acid
       (C) STRANDEDNESS: single
       (D) TOPOLOGY: linear (xi) SEQUENCE DESCRIPTION: SEQ ID NO:1:

```
CCCGCCGCGG CCCGGCGGGT GCCAGATTAG CGGACGCGTG CCCGCGGTTG CAACGGGATC      60

CCGGGCGCTG CAGCTTGGGA GGCGGCTCTC CCCAGGCGGC GTCCGCGGAG ACACCCATCC     120

GTGAACCCCA GGTCCCGGGC CGCCGGCTCG CCGCGCACCC AGGGGCCGGC GGACAGAAGA     180

GCGGCCGAGC GGCTCGAGGC TGGGGGACCG CGGGCGCGGC CGCGCGCTGC CGGGCGGGAG     240

GGCTGGGGGG CCGGGGCCGG GGCCGTGCCC CGGAGCGGGT CGGAGGCCGG GGCCGGGGCC     300

GGGGACGGC GGCTCCCCGC GGCGGCTCCA GCGGCTCGGG GATCCCGGCC GGGCCCCGCA     360

GGGACCATGG CAGCCGGGAG CATCACCACG CTGCCCGCCT TGGCCCGAGG ATGGCGGCAG     420

CGGCGGCTTC CCGCCCGGCC ACTTCAAGGA CCCCAAGCGG CTGTACTGCA AAAACGGGGG     480

CTTTCTTCCT GCGCATCCAC CCCGACGGCC GAGTTGACGG GGTCCGGGAG AAGAGCGACC     540

CTCACATCAA GCTACAACTT CAAGGCAGAA GAGAGAGGAG TTGTGTCTAT CAAAGGAGTG     600

TGTGCTAACC GTTACCTGGC TATGAAGGAA GATGGAAGAT TACTGGGCTT CTAAATGTGT     660

TACGGATGAG TGTTTCTTTT TTGAACGATT GGAATCTAAT AACTACAATA CTTACCGGTC     720

AAGGAAAATA CACCAGTTGG TATGTGGCAC TGAAACGAAC TGGGCAGTAT AAACTTGGAT     780

CCAAAACAGG ACCTGGGCAG AAAGCTAATA CTTTTTCTTC CAATGTCTGC TAAGAGCTGA     840

TTTTAATGGC CACATCTAAT CTCATTTCAC ATGAAAGAAG AAGTATATTT TTAGAAATTT     900

GTTAATGAGA GTAAAAGAAA ATAAATGTGT ATAGCTCAGT TTGGATAATT GGTCAAACAA     960

TTTTTTATCC CAGTAGTAAA ATATGTAACC ATTGTCCCAG TAAAGAAAAA TAACAAAAGT    1020

TGTAAAATGT ATATTCTCCC TTTTATATTG GCATCTGCTG TTACCCAGTG AAGCTTACCT    1080

AGAGCATGAT CTTTTCACGC ATTTGCTTAT CGAAAGAGCT                          1120
```

(2) INFORMATION FOR SEQ ID NO:2:

(i) SEQUENCE CHARACTERISTICS:
       (A) LENGTH: 477 base pairs
       (B) TYPE: nucleic acid
       (C) STRANDEDNESS: single
       (D) TOPOLOGY: linear (ix) FEATURE:
       (A) NAME/KEY: CDS
       (B) LOCATION: 10..474

(xi) SEQUENCE DESCRIPTION: SEQ ID NO:2:

```
CGCAGGACC ATG GCA GCC GGG AGC ATC ACC ACG CTG CCC GCC TTG CCC         48
           Met Ala Ala Gly Ser Ile Thr Thr Leu Pro Ala Leu Pro
             1               5                  10

GAG GAT GGC GGC AGC GGC GCC TTC CCG CCC GGC CAC TTC AAG GAC CCC        96
Glu Asp Gly Gly Ser Gly Ala Phe Pro Pro Gly His Phe Lys Asp Pro
 15                  20                  25
```

```
AAG CGG CTG TAC TGC AAA AAC GGG GGC TTC TTC CTG CGC ATC CAC CCC    144
Lys Arg Leu Tyr Cys Lys Asn Gly Gly Phe Phe Leu Arg Ile His Pro
 30              35                  40                  45

GAC GGC CGA GTT GAC GGG GTC CGG GAG AAG AGC GAC CCT CAC ATC AAG    192
Asp Gly Arg Val Asp Gly Val Arg Glu Lys Ser Asp Pro His Ile Lys
                 50                  55                  60

CTA CAA CTT CAA GCA GAA GAG AGA GGA GTT GTG TCT ATC AAA GGA GTG    240
Leu Gln Leu Gln Ala Glu Glu Arg Gly Val Val Ser Ile Lys Gly Val
             65                  70                  75

TGT GCT AAC CGT TAC CTG GCT ATG AAG GAA GAT GGA AGA TTA CTG GCT    288
Cys Ala Asn Arg Tyr Leu Ala Met Lys Glu Asp Gly Arg Leu Leu Ala
         80                  85                  90

TCT AAA TGT GTT ACG GAT GAG TGT TTC TTT TTT GAA CGA TTG GAA TCT    336
Ser Lys Cys Val Thr Asp Glu Cys Phe Phe Phe Glu Arg Leu Glu Ser
     95                 100                 105

AAT AAC TAC AAT ACT TAC CGG TCA AGG AAA TAC ACC AGT TGG TAT GTG    384
Asn Asn Tyr Asn Thr Tyr Arg Ser Arg Lys Tyr Thr Ser Trp Tyr Val
110                 115                 120                 125

GCA CTG AAA CGA ACT GGG CAG TAT AAA CTT GGA TCC AAA ACA GGA CCT    432
Ala Leu Lys Arg Thr Gly Gln Tyr Lys Leu Gly Ser Lys Thr Gly Pro
                130                 135                 140

GGG CAG AAA GCT ATA CTT TTT CTT CCA ATG TCT GCT AAG AGC            474
Gly Gln Lys Ala Ile Leu Phe Leu Pro Met Ser Ala Lys Ser
                145                 150                 155

TGA                                                                477
```

(2) INFORMATION FOR SEQ ID NO:3:

(i) SEQUENCE CHARACTERISTICS:
        (A) LENGTH: 155 amino acids
        (B) TYPE: amino acid
        (D) TOPOLOGY: linear (ii) MOLECULE TYPE: protein (xi) SEQUENCE DESCRIPTION: SEQ ID NO:3:

```
Met Ala Ala Gly Ser Ile Thr Thr Leu Pro Ala Leu Pro Glu Asp Gly
 1               5                  10                  15

Gly Ser Gly Ala Phe Pro Pro Gly His Phe Lys Asp Pro Lys Arg Leu
                 20                  25                  30

Tyr Cys Lys Asn Gly Gly Phe Phe Leu Arg Ile His Pro Asp Gly Arg
             35                  40                  45

Val Asp Gly Val Arg Glu Lys Ser Asp Pro His Ile Lys Leu Gln Leu
         50                  55                  60

Gln Ala Glu Glu Arg Gly Val Val Ser Ile Lys Gly Val Cys Ala Asn
 65                  70                  75                  80

Arg Tyr Leu Ala Met Lys Glu Asp Gly Arg Leu Leu Ala Ser Lys Cys
                 85                  90                  95

Val Thr Asp Glu Cys Phe Phe Phe Glu Arg Leu Glu Ser Asn Asn Tyr
                100                 105                 110

Asn Thr Tyr Arg Ser Arg Lys Tyr Thr Ser Trp Tyr Val Ala Leu Lys
             115                 120                 125

Arg Thr Gly Gln Tyr Lys Leu Gly Ser Lys Thr Gly Pro Gly Gln Lys
        130                  135                 140

Ala Ile Leu Phe Leu Pro Met Ser Ala Lys Ser
145                 150                 155
```

(2) INFORMATION FOR SEQ ID NO:4:

```
    (i) SEQUENCE CHARACTERISTICS:
        (A) LENGTH: 351 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..348

(xi) SEQUENCE DESCRIPTION: SEQ ID NO:4:

ATG GAT TAC TAC AGA AAA TAT GCA GCT ATC TTT CTG GTC ACA TTG TCG       48
Met Asp Tyr Tyr Arg Lys Tyr Ala Ala Ile Phe Leu Val Thr Leu Ser
  1               5                  10                  15

GTG TTT CTG CAT GTT CTC CAT TCC GCT CCT GAT GTG CAG GAT TGC CCA       96
Val Phe Leu His Val Leu His Ser Ala Pro Asp Val Gln Asp Cys Pro
             20                  25                  30

GAA TGC ACG CTA CAG GAA AAC CCA TTC TTC TCC CAG CCG GGT GCC CCA      144
Glu Cys Thr Leu Gln Glu Asn Pro Phe Phe Ser Gln Pro Gly Ala Pro
         35                  40                  45

ATA CTT CAG TGC ATG GGC TGC TGC TTC TCT AGA GCA TAT CCC ACT CCA      192
Ile Leu Gln Cys Met Gly Cys Cys Phe Ser Arg Ala Tyr Pro Thr Pro
     50                  55                  60

CTA AGG TCC AAG AAG ACG ATG TTG GTC CAA AAG AAC GTC ACC TCA GAG      240
Leu Arg Ser Lys Lys Thr Met Leu Val Gln Lys Asn Val Thr Ser Glu
 65                  70                  75                  80

TCC ACT TGC TGT GTA GCT AAA TCA TAT AAC AGG GTC ACA GTA ATG GGG      288
Ser Thr Cys Cys Val Ala Lys Ser Tyr Asn Arg Val Thr Val Met Gly
                 85                  90                  95

GGT TTC AAA GTG GAG AAC CAC ACG GCG TGC CAC TGC AGT ACT TGT TAT      336
Gly Phe Lys Val Glu Asn His Thr Ala Cys His Cys Ser Thr Cys Tyr
            100                 105                 110

TAT CAC AAA TCT TAA                                                  351
Tyr His Lys Ser
        115

(2) INFORMATION FOR SEQ ID NO:5:

(i) SEQUENCE CHARACTERISTICS:
        (A) LENGTH: 116 amino acids
        (B) TYPE: amino acid
        (D) TOPOLOGY: linear (ii) MOLECULE TYPE: protein (xi) SEQUENCE DESCRIPTION: SEQ ID NO:5:

Met Asp Tyr Tyr Arg Lys Tyr Ala Ala Ile Phe Leu Val Thr Leu Ser
  1               5                  10                  15

Val Phe Leu His Val Leu His Ser Ala Pro Asp Val Gln Asp Cys Pro
             20                  25                  30

Glu Cys Thr Leu Gln Glu Asn Pro Phe Phe Ser Gln Pro Gly Ala Pro
         35                  40                  45

Ile Leu Gln Cys Met Gly Cys Cys Phe Ser Arg Ala Tyr Pro Thr Pro
     50                  55                  60

Leu Arg Ser Lys Lys Thr Met Leu Val Gln Lys Asn Val Thr Ser Glu
 65                  70                  75                  80

Ser Thr Cys Cys Val Ala Lys Ser Tyr Asn Arg Val Thr Val Met Gly
                 85                  90                  95

Gly Phe Lys Val Glu Asn His Thr Ala Cys His Cys Ser Thr Cys Tyr
            100                 105                 110

Tyr His Lys Ser
        115
```

(2) INFORMATION FOR SEQ ID NO:6:

(i) SEQUENCE CHARACTERISTICS:
        (A) LENGTH: 816 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..813

(xi) SEQUENCE DESCRIPTION: SEQ ID NO:6:

```
ATG GCC AAA GTT CCA GAC ATG TTT GAA GAC CTG AAG AAC TGT TAC AGT      48
Met Ala Lys Val Pro Asp Met Phe Glu Asp Leu Lys Asn Cys Tyr Ser
 1               5                  10                  15

GAA AAT GAA GAA GAC AGT TCC TCC ATT GAT CAT CTG TCT CTG AAT CAG      96
Glu Asn Glu Glu Asp Ser Ser Ser Ile Asp His Leu Ser Leu Asn Gln
             20                  25                  30

AAA TCC TTC TAT CAT GTA AGC TAT GGC CCA CTC CAT GAA GGC TGC ATG     144
Lys Ser Phe Tyr His Val Ser Tyr Gly Pro Leu His Glu Gly Cys Met
         35                  40                  45

GAT CAA TCT GTG TCT CTG AGT ATC TCT GAA ACC TCT AAA ACA TCC AAG     192
Asp Gln Ser Val Ser Leu Ser Ile Ser Glu Thr Ser Lys Thr Ser Lys
     50                  55                  60

CTT ACC TTC AAG GAG AGC ATG GTG GTA GTA GCA ACC AAC GGG AAG GTT     240
Leu Thr Phe Lys Glu Ser Met Val Val Val Ala Thr Asn Gly Lys Val
 65                  70                  75                  80

CTG AAG AAG AGA CGG TTG AGT TTA AGC CAA TCC ATC ACT GAT GAT GAC     288
Leu Lys Lys Arg Arg Leu Ser Leu Ser Gln Ser Ile Thr Asp Asp Asp
                 85                  90                  95

CTG GAG GCC ATC GCC AAT GAC TCA GAG GAA GAA ATC ATC AAG CCT AGG     336
Leu Glu Ala Ile Ala Asn Asp Ser Glu Glu Glu Ile Ile Lys Pro Arg
            100                 105                 110

TCA GCA CCT TTT AGC TTC CTG AGC AAT GTG AAA TAC AAC TTT ATG AGG     384
Ser Ala Pro Phe Ser Phe Leu Ser Asn Val Lys Tyr Asn Phe Met Arg
        115                 120                 125

ATC ATC AAA TAC GAA TTC ATC CTG AAT GAC GCC CTC AAT CAA AGT ATA     432
Ile Ile Lys Tyr Glu Phe Ile Leu Asn Asp Ala Leu Asn Gln Ser Ile
    130                 135                 140

ATT CGA GCC AAT GAT CAG TAC CTC ACG GCT GCT GCA TTA CAT AAT CTG     480
Ile Arg Ala Asn Asp Gln Tyr Leu Thr Ala Ala Ala Leu His Asn Leu
145                 150                 155                 160

GAT GAA GCA GTG AAA TTT GAC ATG GGT GCT TAT AAG TCA TCA AAG GAT     528
Asp Glu Ala Val Lys Phe Asp Met Gly Ala Tyr Lys Ser Ser Lys Asp
                165                 170                 175

GAT GCT AAA ATT ACC GTG ATT CTA AGA ATC TCA AAA ACT CAA TTG TAT     576
Asp Ala Lys Ile Thr Val Ile Leu Arg Ile Ser Lys Thr Gln Leu Tyr
            180                 185                 190

GTG ACT GCC CAA GAT GAA GAC CAA CCA GTG CTG CTG AAG GAG ATG CCT     624
Val Thr Ala Gln Asp Glu Asp Gln Pro Val Leu Leu Lys Glu Met Pro
        195                 200                 205

GAG ATA CCC AAA ACC ATC ACA GGT AGT GAG ACC AAC CTC CTC TTC TTC     672
Glu Ile Pro Lys Thr Ile Thr Gly Ser Glu Thr Asn Leu Leu Phe Phe
    210                 215                 220

TGG GAA ACT CAC GGC ACT AAG AAC TAT TTC ACA TCA GTT GCC CAT CCA     720
Trp Glu Thr His Gly Thr Lys Asn Tyr Phe Thr Ser Val Ala His Pro
225                 230                 235                 240

AAC TTG TTT ATT GCC ACA AAG CAA GAC TAC TGG GTG TGC TTG GCA GGG     768
Asn Leu Phe Ile Ala Thr Lys Gln Asp Tyr Trp Val Cys Leu Ala Gly
                245                 250                 255
```

```
GGG CCA CCC TCT ATC ACT GAC TTT CAG ATA CTG GAA AAC CAG GCG        813
Gly Pro Pro Ser Ile Thr Asp Phe Gln Ile Leu Glu Asn Gln Ala
            260             265             270

TAG                                                                816
```

(2) INFORMATION FOR SEQ ID NO:7:

(i) SEQUENCE CHARACTERISTICS:
        (A) LENGTH: 271 amino acids
        (B) TYPE: amino acid
        (D) TOPOLOGY: linear (ii) MOLECULE TYPE: protein (xi) SEQUENCE DESCRIPTION: SEQ ID NO:7:

```
Met Ala Lys Val Pro Asp Met Phe Glu Asp Leu Lys Asn Cys Tyr Ser
 1               5                  10                  15

Glu Asn Glu Glu Asp Ser Ser Ile Asp His Leu Ser Leu Asn Gln
            20                  25                  30

Lys Ser Phe Tyr His Val Ser Tyr Gly Pro Leu His Glu Gly Cys Met
            35                  40                  45

Asp Gln Ser Val Ser Leu Ser Ile Ser Glu Thr Ser Lys Thr Ser Lys
        50                  55                  60

Leu Thr Phe Lys Glu Ser Met Val Val Ala Thr Asn Gly Lys Val
65                  70                  75                  80

Leu Lys Lys Arg Arg Leu Ser Leu Ser Gln Ser Ile Thr Asp Asp
                85                  90                  95

Leu Glu Ala Ile Ala Asn Asp Ser Glu Glu Ile Ile Lys Pro Arg
            100                 105                 110

Ser Ala Pro Phe Ser Phe Leu Ser Asn Val Lys Tyr Asn Phe Met Arg
            115                 120                 125

Ile Ile Lys Tyr Glu Phe Ile Leu Asn Asp Ala Leu Asn Gln Ser Ile
            130                 135                 140

Ile Arg Ala Asn Asp Gln Tyr Leu Thr Ala Ala Leu His Asn Leu
145                 150                 155                 160

Asp Glu Ala Val Lys Phe Asp Met Gly Ala Tyr Lys Ser Ser Lys Asp
                165                 170                 175

Asp Ala Lys Ile Thr Val Ile Leu Arg Ile Ser Lys Thr Gln Leu Tyr
                180                 185                 190

Val Thr Ala Gln Asp Glu Asp Gln Pro Val Leu Leu Lys Glu Met Pro
            195                 200                 205

Glu Ile Pro Lys Thr Ile Thr Gly Ser Glu Thr Asn Leu Leu Phe Phe
            210                 215                 220

Trp Glu Thr His Gly Thr Lys Asn Tyr Phe Thr Ser Val Ala His Pro
225                 230                 235                 240

Asn Leu Phe Ile Ala Thr Lys Gln Asp Tyr Trp Val Cys Leu Ala Gly
                245                 250                 255

Gly Pro Pro Ser Ile Thr Asp Phe Gln Ile Leu Glu Asn Gln Ala
            260                 265                 270
```

(2) INFORMATION FOR SEQ ID NO:8:

(i) SEQUENCE CHARACTERISTICS:
        (A) LENGTH: 480 base pairs
        (B) TYPE: nucleic acid
        (C) STRANDEDNESS: single
        (D) TOPOLOGY: linear (ix) FEATURE:
    (A) NAME/KEY: CDS
    (B) LOCATION: 43..477

(xi) SEQUENCE DESCRIPTION: SEQ ID NO:8:

```
TCAGCACCTT TTAGCTTCCT GAGCAATGTG AAATACAACT TT ATG AGG ATC ATC          54
                                                Met Arg Ile Ile
                                                 1

AAA TAC GAA TTC ATC CTG AAT GAC GCC CTC AAT CAA AGT ATA ATT CGA        102
Lys Tyr Glu Phe Ile Leu Asn Asp Ala Leu Asn Gln Ser Ile Ile Arg
 5              10                  15                  20

GCC AAT GAT CAG TAC CTC ACG GCT GCT GCA TTA CAT AAT CTG GAT GAA        150
Ala Asn Asp Gln Tyr Leu Thr Ala Ala Ala Leu His Asn Leu Asp Glu
                25                  30                  35

GCA GTG AAA TTT GAC ATG GGT GCT TAT AAG TCA TCA AAG GAT GAT GCT        198
Ala Val Lys Phe Asp Met Gly Ala Tyr Lys Ser Ser Lys Asp Asp Ala
            40                  45                  50

AAA ATT ACC GTG ATT CTA AGA ATC TCA AAA ACT CAA TTG TAT GTG ACT        246
Lys Ile Thr Val Ile Leu Arg Ile Ser Lys Thr Gln Leu Tyr Val Thr
        55                  60                  65

GCC CAA GAT GAA GAC CAA CCA GTG CTG CTG AAG GAG ATG CCT GAG ATA        294
Ala Gln Asp Glu Asp Gln Pro Val Leu Leu Lys Glu Met Pro Glu Ile
    70                  75                  80

CCC AAA ACC ATC ACA GGT AGT GAG ACC AAC CTC CTC TTC TTC TGG GAA        342
Pro Lys Thr Ile Thr Gly Ser Glu Thr Asn Leu Leu Phe Phe Trp Glu
85                  90                  95                 100

ACT CAC GGC ACT AAG AAC TAT TTC ACA TCA GTT GCC CAT CCA AAC TTG        390
Thr His Gly Thr Lys Asn Tyr Phe Thr Ser Val Ala His Pro Asn Leu
                105                 110                 115

TTT ATT GCC ACA AAG CAA GAC TAC TGG GTG TGC TTG GCA GGG GGG CCA        438
Phe Ile Ala Thr Lys Gln Asp Tyr Trp Val Cys Leu Ala Gly Gly Pro
            120                 125                 130

CCC TCT ATC ACT GAC TTT CAG ATA CTG GAA AAC CAG GCG TAG               480
Pro Ser Ile Thr Asp Phe Gln Ile Leu Glu Asn Gln Ala
        135                 140                 145
```

(2) INFORMATION FOR SEQ ID NO:9:

(i) SEQUENCE CHARACTERISTICS:
        (A) LENGTH: 145 amino acids
        (B) TYPE: amino acid
        (D) TOPOLOGY: linear (ii) MOLECULE TYPE: protein (xi) SEQUENCE DESCRIPTION: SEQ ID NO:9:

```
Met Arg Ile Ile Lys Tyr Glu Phe Ile Leu Asn Asp Ala Leu Asn Gln
 1               5                  10                  15

Ser Ile Ile Arg Ala Asn Asp Gln Tyr Leu Thr Ala Ala Ala Leu His
                20                  25                  30

Asn Leu Asp Glu Ala Val Lys Phe Asp Met Gly Ala Tyr Lys Ser Ser
            35                  40                  45

Lys Asp Asp Ala Lys Ile Thr Val Ile Leu Arg Ile Ser Lys Thr Gln
        50                  55                  60

Leu Tyr Val Thr Ala Gln Asp Glu Asp Gln Pro Val Leu Leu Lys Glu
65                  70                  75                  80

Met Pro Glu Ile Pro Lys Thr Ile Thr Gly Ser Glu Thr Asn Leu Leu
                85                  90                  95

Phe Phe Trp Glu Thr His Gly Thr Lys Asn Tyr Phe Thr Ser Val Ala
            100                 105                 110
```

```
His Pro Asn Leu Phe Ile Ala Thr Lys Gln Asp Tyr Trp Val Cys Leu
            115                 120                 125

Ala Gly Gly Pro Pro Ser Ile Thr Asp Phe Gln Ile Leu Glu Asn Gln
130                 135                 140

Ala
145

(2) INFORMATION FOR SEQ ID NO:10:

(i) SEQUENCE CHARACTERISTICS:
        (A) LENGTH: 810 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..807

(xi) SEQUENCE DESCRIPTION: SEQ ID NO:10:

ATG GCA GAA GTA CCT GAG CTC GCC AGT GAA ATG ATG GCT TAT TAC AGT      48
Met Ala Glu Val Pro Glu Leu Ala Ser Glu Met Met Ala Tyr Tyr Ser
 1               5                  10                  15

GGC AAT GAG GAT GAC TTG TTC TTT GAA GCT GAT GGC CCT AAA CAG ATG      96
Gly Asn Glu Asp Asp Leu Phe Phe Glu Ala Asp Gly Pro Lys Gln Met
             20                  25                  30

AAG TGC TCC TTC CAG GAC CTG GAC CTC TGC CCT CTG GAT GGC GGC ATC     144
Lys Cys Ser Phe Gln Asp Leu Asp Leu Cys Pro Leu Asp Gly Gly Ile
         35                  40                  45

CAG CTA CGA ATC TCC GAC CAC CAC TAC AGC AAG GGC TTC AGG CAG GCC     192
Gln Leu Arg Ile Ser Asp His His Tyr Ser Lys Gly Phe Arg Gln Ala
     50                  55                  60

GCG TCA GTT GTT GTG GCC ATG GAC AAG CTG AGG AAG ATG CTG GTT CCC     240
Ala Ser Val Val Val Ala Met Asp Lys Leu Arg Lys Met Leu Val Pro
 65                  70                  75                  80

TGC CCA CAG ACC TTC CAG GAG AAT GAC CTG AGC ACC TTC TTT CCC TTC     288
Cys Pro Gln Thr Phe Gln Glu Asn Asp Leu Ser Thr Phe Phe Pro Phe
                 85                  90                  95

ATC TTT GAA GAA GAA CCT ATC TTC TTT GAC ACA TGG GAT AAC GAG GCT     336
Ile Phe Glu Glu Glu Pro Ile Phe Phe Asp Thr Trp Asp Asn Glu Ala
            100                 105                 110

TAT GTG CAC GAT GCA CCT GTA CGA TCA CTG AAC TGC ACG CTC CGG GAC     384
Tyr Val His Asp Ala Pro Val Arg Ser Leu Asn Cys Thr Leu Arg Asp
        115                 120                 125

TCA CAG CAA AAA AGC TTG GTG ATG TCT GGT CCA TAT GAA CTG AAA GCT     432
Ser Gln Gln Lys Ser Leu Val Met Ser Gly Pro Tyr Glu Leu Lys Ala
    130                 135                 140

CTC CAC CTC CAG GGA CAG GAT ATG GAG CAA CAA GTG GTG TTC TCC ATG     480
Leu His Leu Gln Gly Gln Asp Met Glu Gln Gln Val Val Phe Ser Met
145                 150                 155                 160

TCC TTT GTA CAA GGA GAA GAA AGT AAT GAC AAA ATA CCT GTG GCC TTG     528
Ser Phe Val Gln Gly Glu Glu Ser Asn Asp Lys Ile Pro Val Ala Leu
                165                 170                 175

GGC CTC AAG GAA AAG AAT CTG TAC CTG TCC TGC GTG TTG AAA GAT GAT     576
Gly Leu Lys Glu Lys Asn Leu Tyr Leu Ser Cys Val Leu Lys Asp Asp
            180                 185                 190

AAG CCC ACT CTA CAG CTG GAG AGT GTA GAT CCC AAA AAT TAC CCA AAG     624
Lys Pro Thr Leu Gln Leu Glu Ser Val Asp Pro Lys Asn Tyr Pro Lys
        195                 200                 205

AAG AAG ATG GAA AAG CGA TTT GTC TTC AAC AAG ATA GAA ATC AAT AAC     672
Lys Lys Met Glu Lys Arg Phe Val Phe Asn Lys Ile Glu Ile Asn Asn
    210                 215                 220
```

```
AAG CTG GAA TTT GAG TCT GCC CAG TTC CCC AAC TGG TAC ATC AGC ACC       720
Lys Leu Glu Phe Glu Ser Ala Gln Phe Pro Asn Trp Tyr Ile Ser Thr
225                 230                 235                 240

TCT CAA GCA GAA AAC ATG CCC GTC TTC CTG GGA GGG ACC AAA GGC GGC       768
Ser Gln Ala Glu Asn Met Pro Val Phe Leu Gly Gly Thr Lys Gly Gly
                245                 250                 255

CAG GAT ATA ACT GAC TTC ACC ATG CAA TTT GTG TCT TCC TAA               810
Gln Asp Ile Thr Asp Phe Thr Met Gln Phe Val Ser Ser
                260                 265
```

(2) INFORMATION FOR SEQ ID NO:11:

(i) SEQUENCE CHARACTERISTICS:
        (A) LENGTH: 269 amino acids
        (B) TYPE: amino acid
        (D) TOPOLOGY: linear (ii) MOLECULE TYPE: protein (xi) SEQUENCE DESCRIPTION: SEQ ID NO:11:

```
Met Ala Glu Val Pro Glu Leu Ala Ser Glu Met Met Ala Tyr Tyr Ser
 1               5                  10                  15

Gly Asn Glu Asp Asp Leu Phe Phe Glu Ala Asp Gly Pro Lys Gln Met
                20                  25                  30

Lys Cys Ser Phe Gln Asp Leu Asp Leu Cys Pro Leu Asp Gly Gly Ile
            35                  40                  45

Gln Leu Arg Ile Ser Asp His His Tyr Ser Lys Gly Phe Arg Gln Ala
        50                  55                  60

Ala Ser Val Val Val Ala Met Asp Lys Leu Arg Lys Met Leu Val Pro
65                  70                  75                  80

Cys Pro Gln Thr Phe Gln Glu Asn Asp Leu Ser Thr Phe Phe Pro Phe
                85                  90                  95

Ile Phe Glu Glu Glu Pro Ile Phe Phe Asp Thr Trp Asp Asn Glu Ala
                100                 105                 110

Tyr Val His Asp Ala Pro Val Arg Ser Leu Asn Cys Thr Leu Arg Asp
            115                 120                 125

Ser Gln Gln Lys Ser Leu Val Met Ser Gly Pro Tyr Glu Leu Lys Ala
        130                 135                 140

Leu His Leu Gln Gly Gln Asp Met Glu Gln Gln Val Val Phe Ser Met
145                 150                 155                 160

Ser Phe Val Gln Gly Glu Glu Ser Asn Asp Lys Ile Pro Val Ala Leu
                165                 170                 175

Gly Leu Lys Glu Lys Asn Leu Tyr Leu Ser Cys Val Leu Lys Asp Asp
                180                 185                 190

Lys Pro Thr Leu Gln Leu Glu Ser Val Asp Pro Lys Asn Tyr Pro Lys
            195                 200                 205

Lys Lys Met Glu Lys Arg Phe Val Phe Asn Lys Ile Glu Ile Asn Asn
        210                 215                 220

Lys Leu Glu Phe Glu Ser Ala Gln Phe Pro Asn Trp Tyr Ile Ser Thr
225                 230                 235                 240

Ser Gln Ala Glu Asn Met Pro Val Phe Leu Gly Gly Thr Lys Gly Gly
                245                 250                 255

Gln Asp Ile Thr Asp Phe Thr Met Gln Phe Val Ser Ser
                260                 265
```

(2) INFORMATION FOR SEQ ID NO:12:

(i) SEQUENCE CHARACTERISTICS:
    (A) LENGTH: 462 base pairs
    (B) TYPE: nucleic acid
    (C) STRANDEDNESS: single
    (D) TOPOLOGY: linear (ix) FEATURE:
    (A) NAME/KEY: CDS
    (B) LOCATION: 1..459

(xi) SEQUENCE DESCRIPTION: SEQ ID NO:12:

```
GCA CCT GTA CGA TCA CTG AAC TGC ACG CTC CGG GAC TCA CAG CAA AAA      48
Ala Pro Val Arg Ser Leu Asn Cys Thr Leu Arg Asp Ser Gln Gln Lys
 1               5                  10                  15

AGC TTG GTG ATG TCT GGT CCA TAT GAA CTG AAA GCT CTC CAC CTC CAG      96
Ser Leu Val Met Ser Gly Pro Tyr Glu Leu Lys Ala Leu His Leu Gln
             20                  25                  30

GGA CAG GAT ATG GAG CAA CAA GTG GTG TTC TCC ATG TCC TTT GTA CAA     144
Gly Gln Asp Met Glu Gln Gln Val Val Phe Ser Met Ser Phe Val Gln
         35                  40                  45

GGA GAA GAA AGT AAT GAC AAA ATA CCT GTG GCC TTG GGC CTC AAG GAA     192
Gly Glu Glu Ser Asn Asp Lys Ile Pro Val Ala Leu Gly Leu Lys Glu
 50                  55                  60

AAG AAT CTG TAC CTG TCC TGC GTG TTG AAA GAT GAT AAG CCC ACT CTA     240
Lys Asn Leu Tyr Leu Ser Cys Val Leu Lys Asp Asp Lys Pro Thr Leu
 65                  70                  75                  80

CAG CTG GAG AGT GTA GAT CCC AAA AAT TAC CCA AAG AAG AAG ATG GAA     288
Gln Leu Glu Ser Val Asp Pro Lys Asn Tyr Pro Lys Lys Lys Met Glu
             85                  90                  95

AAG CGA TTT GTC TTC AAC AAG ATA GAA ATC AAT AAC AAG CTG GAA TTT     336
Lys Arg Phe Val Phe Asn Lys Ile Glu Ile Asn Asn Lys Leu Glu Phe
         100                 105                 110

GAG TCT GCC CAG TTC CCC AAC TGG TAC ATC AGC ACC TCT CAA GCA GAA     384
Glu Ser Ala Gln Phe Pro Asn Trp Tyr Ile Ser Thr Ser Gln Ala Glu
     115                 120                 125

AAC ATG CCC GTC TTC CTG GGA GGG ACC AAA GGC GGC CAG GAT ATA ACT     432
Asn Met Pro Val Phe Leu Gly Gly Thr Lys Gly Gly Gln Asp Ile Thr
 130                 135                 140

GAC TTC ACC ATG CAA TTT GTG TCT TCC TAA                             462
Asp Phe Thr Met Gln Phe Val Ser Ser
145                 150
```

(2) INFORMATION FOR SEQ ID NO:13:

(i) SEQUENCE CHARACTERISTICS:
        (A) LENGTH: 153 amino acids
        (B) TYPE: amino acid
        (D) TOPOLOGY: linear (ii) MOLECULE TYPE: protein (xi) SEQUENCE DESCRIPTION: SEQ ID NO:13:

```
Ala Pro Val Arg Ser Leu Asn Cys Thr Leu Arg Asp Ser Gln Gln Lys
 1               5                  10                  15

Ser Leu Val Met Ser Gly Pro Tyr Glu Leu Lys Ala Leu His Leu Gln
             20                  25                  30

Gly Gln Asp Met Glu Gln Gln Val Val Phe Ser Met Ser Phe Val Gln
         35                  40                  45

Gly Glu Glu Ser Asn Asp Lys Ile Pro Val Ala Leu Gly Leu Lys Glu
     50                  55                  60

Lys Asn Leu Tyr Leu Ser Cys Val Leu Lys Asp Asp Lys Pro Thr Leu
 65                  70                  75                  80
```

```
Gln Leu Glu Ser Val Asp Pro Lys Asn Tyr Pro Lys Lys Met Glu
                85                  90                  95

Lys Arg Phe Val Phe Asn Lys Ile Glu Ile Asn Asn Lys Leu Glu Phe
            100                 105                 110

Glu Ser Ala Gln Phe Pro Asn Trp Tyr Ile Ser Thr Ser Gln Ala Glu
            115                 120                 125

Asn Met Pro Val Phe Leu Gly Gly Thr Lys Gly Gly Gln Asp Ile Thr
    130                 135                 140

Asp Phe Thr Met Gln Phe Val Ser Ser
145                 150
```

(2) INFORMATION FOR SEQ ID NO:14:

(i) SEQUENCE CHARACTERISTICS:
        (A) LENGTH: 454 base pairs
        (B) TYPE: nucleic acid
        (C) STRANDEDNESS: single
        (D) TOPOLOGY: linear (xi) SEQUENCE DESCRIPTION: SEQ ID NO:14:

```
ATGGCCGAGG GCGAAATTAC AACATTCACC GCCCTCACCG AAAAGTTTAA TCTGCCTCCC    60

GGGAATTACA AGAAGCCCAA ACTCCTCTAC TGCAGCAACG GGGGCCACTT CCTGAGGATT   120

CTTCCGGATG GCACAGTGGA TGGGACAAGG GACAGGAGCC GACCAGCACA TTCAGCTGCA   180

ACTCAGTGCG GAAAGCGTGG GGGAGGTGTA TATAAAGAGT ACCGAGACTG GCCAGTACTT   240

TGGCAATGGA CACCGACGGG CTTTTATACG GCTCACAGAC ACCAAATGAG GAATGTTTGT   300

TCCTGGAAAG GCTGGAGGAG AAACCATTAC AACACCTATA TATCCAAGAA GCATGCAGAG   360

AAGAATTGGT TTGTTGGCCT CAAGCGGTCC TCGGACTCAC TATGGCCAGA AAGCAATCTT   420

GTTTCTCCCC CTGCCAGTCT CTTCTGATTA ATAA                                454
```

(2) INFORMATION FOR SEQ ID NO:15:

(i) SEQUENCE CHARACTERISTICS:
        (A) LENGTH: 156 amino acids
        (B) TYPE: amino acid
        (C) STRANDEDNESS:
        (D) TOPOLOGY: linear (xi) SEQUENCE DESCRIPTION: SEQ ID NO:15:

```
Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
                20                  25                  30

Asn Gly Gly His Phe Leu Arg Ile Leu Pro Asp Gly Thr Val Asp Gly
            35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Tyr
65                  70                  75                  80

Leu Ala Met Asp Thr Asp Gly Leu Leu Tyr Gly Ser Gln Thr Pro Asn
                85                  90                  95

Glu Glu Cys Leu Phe Leu Glu Arg Leu Glu Glu Asn His Tyr Asn Thr
            100                 105                 110

Tyr Ile Ser Lys Lys His Ala Glu Lys Asn Trp Phe Val Gly Leu Lys
            115                 120                 125

Lys Asn Gly Ser Cys Lys Arg Gly Pro Arg Thr His Tyr Gly Gln Lys
    130                 135                 140
```

Ala Ile Leu Phe Leu Pro Leu Pro Val Ser Ser Asp
145                 150                 155

(2) INFORMATION FOR SEQ ID NO:16:

(i) SEQUENCE CHARACTERISTICS:
        (A) LENGTH: 221 base pairs
        (B) TYPE: nucleic acid
        (C) STRANDEDNESS: single
        (D) TOPOLOGY: linear (xi) SEQUENCE DESCRIPTION: SEQ ID NO:16:

ATGGAACCGG TCGACCCGCG TCTGGAACCA TGGAAACACC CCGGGTCCCA GCCGAAAACC      60

GCGTGCACCA ACTGCTACTT GCAAAAAATG CTGCTTCCAC TGCCAGGTTT GCTTCATCAC     120

CAAAGCCCTA GGTATCTCTT ACGGCCGTAA AAAACGTCGT TCAGCGACGT CGTCCGCCGC     180

AGGGATCCCA GACCCACCAG GTTTCTCTGT CTAAACAGTG A                        221

(2) INFORMATION FOR SEQ ID NO:17:

(i) SEQUENCE CHARACTERISTICS:
        (A) LENGTH: 72 amino acids
        (B) TYPE: amino acid
        (C) STRANDEDNESS:
        (D) TOPOLOGY: linear (xi) SEQUENCE DESCRIPTION: SEQ ID NO:17:

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
                20                  25                  30

His Cys Gln Val Cys Phe Ile Thr Lys Ala Leu Gly Ile Ser Tyr Gly
            35                  40                  45

Arg Lys Lys Arg Arg Gln Arg Arg Pro Pro Gln Gly Ser Gln Thr
        50                  55                  60

His Gln Val Ser Leu Ser Lys Gln
65                  70

(2) INFORMATION FOR SEQ ID NO:18:

(i) SEQUENCE CHARACTERISTICS:
        (A) LENGTH: 263 base pairs
        (B) TYPE: nucleic acid
        (C) STRANDEDNESS: single
        (D) TOPOLOGY: linear (xi) SEQUENCE DESCRIPTION: SEQ ID NO:18:

ATGGAACCAG TCGACCCTAG ACTGGAACCG TGGAAACACC CGGGTTCCCA GCCGAAAACT      60

GCATGCACCA ACTGTTACTG TAAAAAGTGT TGCTTCCACT GTCAAGTTTG TTTCATCACC     120

AAGGCTTTGG GTATCTCCTA CGGTCGTAAG AAACGTAGAA CAGCGCAGAC GTCCACCGCA     180

AGGTTCTCAG ACTCATCAAG TTTCCTTGTC CAAGCAACCG ACCTCCCAAT CTCGCGGTGA     240

ACCCGACAGG TCCTAAGGAA TAG                                            263

(2) INFORMATION FOR SEQ ID NO:19:

(i) SEQUENCE CHARACTERISTICS:
        (A) LENGTH: 86 amino acids
        (B) TYPE: amino acid
        (C) STRANDEDNESS:
        (D) TOPOLOGY: linear (xi) SEQUENCE DESCRIPTION: SEQ ID NO:19:

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
                20                  25                  30

His Cys Gln Val Cys Phe Ile Thr Lys Ala Leu Gly Ile Ser Tyr Gly
            35                  40                  45

Arg Lys Lys Arg Arg Gln Arg Arg Pro Pro Gln Gly Ser Gln Thr
        50                  55                  60

His Gln Val Ser Leu Ser Lys Gln Pro Thr Ser Gln Ser Arg Gly Asp
65                  70                  75                  80

Pro Thr Gly Pro Lys Glu
                85

(2) INFORMATION FOR SEQ ID NO:20:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:20:

AAGGACAGAA GCGGCCGCGG GACCATGGCA G                                31

(2) INFORMATION FOR SEQ ID NO:21:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:21:

AAGGACAGAA GCGGCCGCTC AGCTCTTAGC AGCCATTGG                        39

(2) INFORMATION FOR SEQ ID NO:22:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (xi) SEQUENCE DESCRIPTION: SEQ ID NO:22:

CTAGGGATCC ACCATGGCCG AGGGCGAAAT TACAACATTC ACCGCCCTCA CCGAAAAGTT    60

TAATCTGCCT CCCGG                                                    75

(2) INFORMATION FOR SEQ ID NO:23:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:23:

GATCGAATTC TCAATCAGAA GAAGCTGGCA G                                 31

(2) INFORMATION FOR SEQ ID NO:24:

(i) SEQUENCE CHARACTERISTICS:
        (A) LENGTH: 14 amino acids (B) TYPE: amino acid
            (C) STRANDEDNESS:
            (D) TOPOLOGY: linear (xi) SEQUENCE DESCRIPTION: SEQ ID NO:24:

Ala Glu Gly Glu Ile Thr Thr Phe Thr Ala Leu Thr Glu Lys
1               5                   10

(2) INFORMATION FOR SEQ ID NO:25:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (xi) SEQUENCE DESCRIPTION: SEQ ID NO:25:

CTAGTCTAGA TCAGGCGTAG TCGGGCACGT CGTATGGGTA ATCAGAAGAG ACTGGCAGG          59

(2) INFORMATION FOR SEQ ID NO:26:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (xi) SEQUENCE DESCRIPTION: SEQ ID NO:26:

GATCGAATTC TCACTTGTCA TCGTCGTCCT TGTCGTCACG CGTATCAGAA GAGACTGGCA         60
G                                                                       61

(2) INFORMATION FOR SEQ ID NO:27:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:27:

CTAGGGATCC ACCATGGAAC CAGTCGACC                                          29

(2) INFORMATION FOR SEQ ID NO:28:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:28:

GATCGAATTC TCATTCCTTA GGACCTGTCG G                                       31

(2) INFORMATION FOR SEQ ID NO:29:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (xi) SEQUENCE DESCRIPTION: SEQ ID NO:29:

CTAGTCTAGA TCAGGCGTAG TCGGGCACGT CGTATGGGTA TTCCTTAGGA CCTGTCGG           58

(2) INFORMATION FOR SEQ ID NO:30:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (xi) SEQUENCE DESCRIPTION: SEQ ID NO:30:

CTAGGAATTC AGATCACTGT TTAGACAGAG                                      30

(2) INFORMATION FOR SEQ ID NO:31:

(i) SEQUENCE CHARACTERISTICS:
            (A) LENGTH: 56 base pairs
            (B) TYPE: nucleic acid
            (C) STRANDEDNESS: single
            (D) TOPOLOGY: linear (xi) SEQUENCE DESCRIPTION: SEQ ID NO:31:

CTGAGAATTC TCACTTGTCA TCGTCGTCCT TGTAGTCCTG TTTAGACAGA GAAACC         56

(2) INFORMATION FOR SEQ ID NO:32:

(i) SEQUENCE CHARACTERISTICS:
            (A) LENGTH: 61 base pairs
            (B) TYPE: nucleic acid
            (C) STRANDEDNESS: single
            (D) TOPOLOGY: linear (xi) SEQUENCE DESCRIPTION: SEQ ID NO:32:

CTGAGAATTC TCAGGCGTAG TCGGGCACGT CGTATGGGTA CTGTTTAGAC AGAGAAACCT     60
G                                                                     61

(2) INFORMATION FOR SEQ ID NO:33:

(i) SEQUENCE CHARACTERISTICS:
            (A) LENGTH: 37 base pairs
            (B) TYPE: nucleic acid
            (C) STRANDEDNESS: single
            (D) TOPOLOGY: linear (xi) SEQUENCE DESCRIPTION: SEQ ID NO:33:

CTAGGGATCC ACCATGAGGA TCATCAAATA CGAATTC                              37

(2) INFORMATION FOR SEQ ID NO:34:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (xi) SEQUENCE DESCRIPTION: SEQ ID NO:34:

GCACTTCTCG AGCTACGCCT GGTTTTCCAG TATC                                 34

(2) INFORMATION FOR SEQ ID NO:35:

(i) SEQUENCE CHARACTERISTICS:
            (A) LENGTH: 8 amino acids
            (B) TYPE: amino acid
            (C) STRANDEDNESS:
            (D) TOPOLOGY: linear (xi) SEQUENCE DESCRIPTION: SEQ ID NO:35:

Asp Tyr Lys Asp Asp Asp Asp Lys
1               5

-continued (2) INFORMATION FOR SEQ ID NO:36:

(i) SEQUENCE CHARACTERISTICS:
(A) LENGTH: 9 amino acids
(B) TYPE: amino acid
(C) STRANDEDNESS:
(D) TOPOLOGY: linear (xi) SEQUENCE DESCRIPTION: SEQ ID NO:36:

Tyr Pro Tyr Asp Val Pro Asp Tyr Ala
1               5